(12) United States Patent
Schuchman et al.

(10) Patent No.: US 9,114,139 B2
(45) Date of Patent: *Aug. 25, 2015

(54) DOSE ESCALATION ENZYME REPLACEMENT THERAPY FOR TREATING ACID SPHINGOMYELINASE DEFICIENCY

(71) Applicants: Icahn School of Medicine at Mount Sinai, New York, NY (US); Genzyme Corporation, Cambridge, MA (US)

(72) Inventors: Edward H. Schuchman, Haworth, NJ (US); Robert J. Desnick, New York, NY (US); Gerald F. Cox, Needham, MA (US); Laura P. Andrews, Bolton, MA (US); James M. Murray, Shrewsbury, MA (US)

(73) Assignees: Icahn School of Medicine at Mount Sinai, New York, NY (US); Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/156,894

(22) Filed: Jan. 16, 2014

(65) Prior Publication Data

US 2014/0335070 A1 Nov. 13, 2014

Related U.S. Application Data

(60) Continuation of application No. 13/679,623, filed on Nov. 16, 2012, now Pat. No. 8,709,408, which is a division of application No. 12/870,790, filed on Aug. 28, 2010, now Pat. No. 8,349,319.

(60) Provisional application No. 61/238,113, filed on Aug. 28, 2009.

(51) Int. Cl.
*A61K 38/46* (2006.01)

(52) U.S. Cl.
CPC ....... *A61K 38/465* (2013.01); *C12Y 301/04012* (2013.01)

(58) Field of Classification Search
USPC ............................................. 434/94.6, 94.61
See application file for complete search history.

(56) References Cited

U.S. PATENT DOCUMENTS

| 4,039,388 A | 8/1977 | Gal et al. |
| 4,082,781 A | 4/1978 | Gal |
| 4,683,195 A | 7/1987 | Mullis et al. |
| 5,641,670 A | 6/1997 | Treco et al. |
| 5,686,240 A | 11/1997 | Schuchman et al. |
| 5,773,278 A | 6/1998 | Schuchman et al. |
| 6,541,218 B1 | 4/2003 | Schuchman et al. |
| 6,670,165 B2 | 12/2003 | Canfield et al. |
| 7,001,994 B2 | 2/2006 | Zhu et al. |
| 7,442,372 B2 | 10/2008 | Kakkis et al. |
| 7,527,956 B2 | 5/2009 | Van Patten et al. |
| 7,563,591 B2 | 7/2009 | Chamoles et al. |
| 7,658,916 B2 | 2/2010 | Zhu et al. |
| 7,750,050 B2 | 7/2010 | Schuchman et al. |
| 7,858,576 B2 | 12/2010 | LeBowitz et al. |
| 7,910,545 B2 | 3/2011 | Meeker et al. |
| 8,349,319 B2 * | 1/2013 | Schuchman et al. ......... 424/94.6 |
| 8,658,162 B2 * | 2/2014 | Schuchman et al. ......... 424/94.6 |
| 8,709,408 B2 * | 4/2014 | Schuchman et al. ......... 424/94.6 |
| 2002/0137125 A1 | 9/2002 | Zhu |
| 2002/0150981 A1 | 10/2002 | Canfield |
| 2003/0153739 A1 | 8/2003 | Schuchman et al. |
| 2005/0048047 A1 | 3/2005 | Kakkis et al. |
| 2005/0058634 A1 | 3/2005 | Zhu |
| 2006/0281145 A1 | 12/2006 | Zhu |
| 2007/0280925 A1 | 12/2007 | Meeker et al. |
| 2009/0022702 A1 | 1/2009 | Zhu |
| 2009/0029467 A1 | 1/2009 | LeBowitz et al. |
| 2009/0123451 A1 | 5/2009 | Dodge et al. |
| 2009/0130079 A1 | 5/2009 | Dodge et al. |
| 2010/0143297 A1 | 6/2010 | Zhu et al. |

FOREIGN PATENT DOCUMENTS

| DE | 69231701.5 | 9/2001 |
| EP | 0 161 788 | 11/1995 |
| EP | 0 520 843 | 2/2001 |
| WO | WO 2004/045574 | 6/2004 |
| WO | WO 2006/058385 | 6/2006 |
| WO | WO 2007/078806 | 7/2007 |
| WO | WO 2007/084737 | 7/2007 |
| WO | WO 2008/136451 | 11/2008 |
| WO | WO 2010/015816 | 2/2010 |
| WO | WO 2010/075010 | 7/2010 |

OTHER PUBLICATIONS

Akeboshi et al., 2009, "Production of human β-hexosaminidase A with higly phosphorylated N-glycans by the overxpression of the *Ogataea minuta* MNN4 gene." Glycobiol. 19(9):1002-1009.

Barbon, 2005, "AAV8-mediated hepatic expression of acid sphingomyelinase corrects the metabolic defect in the visceral organs of a mouse model of Niemann-Pick disease," Mol. Ther. 12(3):431-40.

Barton and Neufeld, 1971, "The Hurler corrective factor. Purification and some properties", J. Biol. Chern. 246:7773-7779.

Bernardo et al., 1995, "Purification, characterization, and biosynthesis of human acid ceramidase", J ,Biol. Chem. 270(19):11098-102.

Besley & Elleder, 1986, "Enzyme activities and phospholipid storage patterns in brain and spleen samples from Niemann-pick disease variants: a comparison of neuropathic and non-neuropathic forms." J. Inher. Metab. Dis. 9:59-71.

Besley et al., 1980, "Somatic cell hybridization studies showing different gene mutations in Niemann-Pick variants." Hum. Genet. 54:409-412.

Beutler et al., 1977, "Enzyme replacement therapy in Gaucher's disease: preliminary clinical trial of a new enzyme preparation", Proc. Natl. Acad. Sci. USA 74:4620-4623.

(Continued)

*Primary Examiner* — Ralph Gitomer
(74) *Attorney, Agent, or Firm* — Jones Day

(57) ABSTRACT

The invention relates to dose escalation enzyme replacement therapy using acid sphingomyelinase (ASM) for the treatment of human subjects having acid sphingomyelinase deficiency (ASMD), and, in particular, patients with non-neurological manifestations of Niemann-Pick Disease (NPD), and in certain embodiments, NPD type B.

18 Claims, 15 Drawing Sheets

(56) References Cited

OTHER PUBLICATIONS

Brady et al., 1966, "The metabolism of sphingomyelin II. Evidence of an enzymatic deficiency in Niemann-Pick disease." Proc. Natl. Acad. Sci. USA 55:366-369.
Brady et al., 1972, "Enzyme Defects in the Sphingolipidoses and their application to Diagnosis." Annals of Clin. Lab. Sci. 2(4): 285-294.
Buccinna et al., 2009, "Alterations of myelin-specific proteins and sphingolipids characterize the brains of acid sphingomyelinase-deficient mice, an animal model of Niemann-Pick disease type A." J. Neurochem. 109:105-115.
Callahan et al., 1985, "cDNA clones for Human sphingomyelinase Isolated Using the Lambda GT11 System." Pediatric Res. 19:244a.
Calogera et al., 2002, "The demographics and distribution of type B Niemann-Pick disease: novel mutations lead to new genotype/phenotype correlations," American Journal of Human Genetics 71(6):1413-1419.
Da Veiga Pereira et al., 1991, "Regional assignment of the human acid sphingomyelinase gene (SMPD1) by PCR analysis of somatic cell hybrids and in situ hybridization to 11." Genomics, vol. 9(2), pp. 229-234.
Dean et al., 1979, "Enzyme Replacement Therapy by Fibroblast Transplantation: Long-term Biochemical Study in Three cases of Hunter's Syndrome." J. Clin. Invest. 63: 138-145.
Desnick et al., 1979, "Enzyme therapy in Fabry disease: differential in-vivo plasma clearance and metabolic effectiveness of plasma and splenic alpha-galactosidase A isozymes", Proc Natl Acad Sci 76(10):5326-30.
Dhami et al., 2001, "Analysis of the lung pathology and alveolar macrophage function in the acid sphingomyelinase—deficient mouse model of Niemann-Pick disease." Lab. Invest. 81: 987-999.
Dixit et al., 1991, "Construction and expression of a recombinant adeno-associated virus that harbors a human β-globin-encoding DNA." Gene 104(2): 253-257.
Dodge et al., 2009, "Intracerebroventricular infusion of acid sphingomyelinase corrects CNS manifestations in a mouse model of Niemann-Pick A disease." Experimental Neurology 215: 349-357.
Dodge, 2005, "Gene transfer of human acid sphingomyelinase corrects neuropathology and motor deficits in a mouse model of Niemann-Pick type A disease," PNAS 102(49):17822-7.
Elleder, 1989, "Niemann-Pick Disease." Pathol. Res. Pract. 185:293-328.
Ferlinz et al., 1991,"Molecular Basis of Acid Sphingomyelinase Deficiency in a Patient With Niemann-Pick Disease Type A." Biochem. Biophys. Res. Comm 179:1187-1191.
Fischer et al., 1980, "Phosphomannosyl-enzyme receptors in rat liver", J. Biol. Chem. 255:9608-9615.
Flotte et al., 1995, "Adeno-associated virus vectors for gene therapy," Gene Ther. 2(6):357-62.
Furbish et al., 1977, "Enzyme replacement therapy in Gaucher's disease: large-scale purification of glucocerebrosidase suitable for human administration", Proc. Natl. Acad. Sci. USA 74:3560-3563.
Gardlik et al., 2005, "Vectors and delivery systems in gene therapy," Med. Sci. Monit. 11(4):RA110-21.
Garnacho et al., 2008, "Delivery of acid sphingomyelinase in normal and niemann-pick disease mice using intercellular adhesion molecule-1-targeted polymer nanocarriers." J. Pharmacol. Exp. Ther. 325:400-408.
Goncalves, 2005, "Adeno-associated virus: from defective virus to effective vector," Virology 2:1-17.
Grobhans, 2000, "Gene therapy—when a simple concept meets a complex reality: Review on gene therapy," Functional and Integrative Genomics 1:142-145.
He et al., 1999, "Characterization of human acid sphingomyelinase purified from the media of overexpressing Chinese hamster ovary cells." Biochimica et Biophsyica Acta 1432: 251-264.
He et al., 2003, "A fluorescence-based, high-performance liquid chromatographic assay to determine acid sphingomyelinase activity and diagnose types A and B Niemann-Pick disease." Analytical Biochemistry 314: 116-120.

Jane et al., 1998, "Vector development: a major obstacle in human gene therapy," Ann Med. 30(5):413-5.
Jones et al., 2008, "Characterization of common SMPD1 mutations causing types A and B Niemann-Pick disease and generation of mutation-specific mouse models." Molec Gen. and Metabolism 95:152-162.
Jung et al., 2001, "Adeno-associated viral vector-mediated gene transfer results in long-term enzymatic and functional correction in multiple organs of Fabry mice," Proc Natl Acad Sci U S A. 98(5):2676-81.
Kaleko et al., 1991, "Persistent Gene Expression After Retroviral Gene Transfer into Liver Cells In Vivo." Human Gene Therapy 2:27-32.
Kaufman and Sharp, 1982, "Construction of a modular dihydrofolate reductase cDNA gene: analysis of signals utilized for efficient expression." Mol. Cell. Biol. 2:1304-1319.
Klar et al., 1988, "Synthesis of Pyrenesillfonylamido-sphingomyelin and Its Use as Substrate for Determining Sphingomyelinase Activity and Diagnosing Niemann-Pick Disease". Clin. Chim. Acta 176:259-268.
Koch et al., 1996, "Molecular cloning and characterization of a full-length complementary DNA encoding human acid ceramidase", J. Biol. Chem. 271:33110-33115.
Krivit et al., 1973, "Prospectus", Birth Defects: Original Article Series IX:232-233.
Ledley, 1991, "Clinical considerations in the design of protocols for somatic gene therapy," Hum Gene Ther. 2(1):77-83.
Levade et al., 1986, "Sphingomyelinases and Niemann-Pick disease" J. Clin. Chem. Clin. Biochem. 24:205-220.
Levran et al., 1991, "Niemann-Pick Disease: A Frequent Missense Mutation in the Acid Sphingomyelinase Gene of Ashkenazi Jewish Type A and B Patients." Proc. Natl. Acad. Sci. USA 88:3748-3752.
Levran et al., 1991, "Niemann-Pick Type B Disease. Identification of a Single Codon Deletion in the Acid Sphingomyelinase Gene and Genotype/Phenotype Correlations in Type A and B Patients." J. Clin, Invest. 88:806-810.
Levran et al., 1992, "Identification and Expression of a Common Missense Mutation (L302P) in the Acid Sphingomyelinase Gene of Ashkenazi Jewish Type A Niemann-Pick Disease Patients". Blood 80:2081-2087.
Levran et al., 1993, "Type A Niemann-Pick Disease: a Frameshift Mutation in the Acid Sphingomyelinase Gene (fsP330) Occurs in Ashkenazi Jewish Patients". Human Mutation 2:317-319.
Li et al. 2007, "Inhibition of sphingomyelin synthase (SMS) affects intracellular sphingomyelin accumulation and plasma membrane lipid organization." Biochim Biophys Act 1771(9):1186-1194.
Marshall, 1995, "Gene therapy's growing pains," Science 269(5227):1050-1055.
Matsuoka et al., 2010, "Introduction of N-Glycan Sequon into Hexa Enhances Human β-Hexosaminidase Cellular Uptake in a Model of Sandhoff Disease." Molec Therap. 18(8):1519-1526.
McGovern et al, 2009, "A Phase 1 Trial of Recombinant Human Acid Sphingomyelinase (rhASM) Enzyme Replacement Therapy in Adults with ASM Deficiency (ASMD)" Abstract for International Congress on Inborn Errors of Metabolism poster session, Aug. 27, 2009.
McGovern et al, 2009, "A Phase 1 Trial of Recombinant Human Acid Sphingomyelinase (rhASM) Enzyme Replacement Therapy in Adults with ASM Deficiency (ASMD)" Poster Presentation at International Congress on Inborn Errors of Metabolism, Aug. 31, 2009.
McGovern et al., 2004, "Lipid abnormalities in children with types A and B Niemann Pick disease." J Pediatr. 145(1):77-81.
McGovern et al., 2008, "A prospective, cross-sectional survey study of the natural history of Niemann-Pick disease type B." Pediatr 122(2):e341-9.
McGovern et al., 2009, "A Phase 1 Trial of Recombinant Human Acid Sphingomyelinase (rhASM) Enzyme Replacement Therapy in Adults with ASM Deficiency" American Society of Human Genetics Presentation, Oct. 20-24, 2009.
McGovern, 2009, "A Phase 1 trial of recombinant human acid sphingomyelinase (rhASM) enzyme replacement therapy in adults with ASM deficiency (ASMD)." American Society of Human Genetics, abstract for presentation, Sep. 1, 2009.

(56) References Cited

OTHER PUBLICATIONS

McGovern, 2010, "A Phase 1 trial of recombinant human acid sphingomyelinase (rhASM) enzyme replacement therapy in adults with non-neuronopathic ASM deficiency (ASMD; Niemann-Pick B)." Lysosomal Disease Network World Symposium, Abstract, Sep. 10, 2010.
McVie-Wylie et al., 2008, "Biochemical and Pharmacological Characterization of Different Recombinant Acid α-Glucosidase Preparations Evaluated for the Treatment of Pompe Disase." Mol. Genet metab 94(4):448-455.
Merril et all, 1979, "Trace polypeptides in cellular extracts and human body fluids detected by two-dimensional electrophoresis and a highly sensitive silver strain." Proc. Natl. Acad Sci. 76:4335-4339.
Miekle et al., 1999, "Prevalence of lysosomal storage disorders." JAMA 281(3): 249-254.
Milhas et al., 2010, "Sphingomyelin metabolism at the plasma membrane: implications for bioactive sphingolipids." FEBS Letters 584: 1887-1894.
Miranda et al., 2000, "Infusion of recombinant human acid sphingomyelinase into Niemann-Pick disease mice leads to visceral, but not neurological, correction of the pathophysiology", The FASEB Journal 14(13):1988-1995.
Murray et al., 2006, "Elevations of Pro-Inflammatory Cytokines and Decreases in Cardiovascular Hemodynamics Following Intravenous Administration of Recombinant Human Acid Sphingomyelinase (rhASM) to Acid Sphingomyelinase Knock-out (ASMKO) Mice" Poster Presentation at the Society of Toxicology, Mar. 5-9, 2006.
Murray et al., 2006, "Elevations of Pro-Inflammatory Cytokines and Decreases in Cardiovascular Hemodynamics Following Intravenous Administration of Recombinant Human Acid Sphingomyelinase (rhASM) to Acid Sphingomyelinase Knock-out (ASMKO) Mice" Abstract for Poster Presentation at the Society of Toxicology, Feb. 13, 2006.
Muzyczka, 1994, "Adeno-associated virus (AAV) vectors: will they work?" J. Clin. Invest. 94(4):1351.
Navon et al., 1989, "The Mutations in Ashkenazi Jews with Adult GMZ Gangliosidosis, the Adult Form of Tay-Sachs Disease." Science 243:1471-1474.
Nickerson et al., 2005, "Dose Responsive Toxicological Findings Following Intravenous Administration of Recombinant Human Acid Sphingomyelinase (rhASM) to Acid Sphingomyelinase Knock-out (ASMKO) Mice." Abstract for Poster Presentation at the American Society of Human Genetics, Oct. 25-29, 2005.
Nickerson et al.., 2005, "Dose Responsive Toxicological Findings Following Intravenous Administration of Recombinant Human Acid Sphingomyelinase (rhASM) to Acid Sphingomyelinase Knock-out (ASMKO) Mice." Poster Presentation at the American Society of Human Genetics, Oct. 25-29, 2005.
Notice of Allowance and Fees Due of U.S. Appl. No. 12/870,790, dated Oct. 26, 2012.
Office Action of U.S. Appl. No. 12/870,790, dated May 24, 2012.
Office Action of U.S. Appl. No. 12/870,790, dated Sep. 4, 2012.
Orkin, 1995, Report and Recommendations of the Panel to Asses the NIH Investment in Research on Gene Therapy.
Osborne et al., 1991, "Retrovirus-mediated gene expression in mammalian cells," Curr Opin Biotechnol. 2(5):708-12.
Passini et al., 2005, "AAV vector-mediated correction of brain pathology in a mouse model of Niemann-Pick A disease," Mol. Ther. 11(5):754-62.
Patat et al., 2000, "Designing and interpreting the results of first-time-to-man studies", Dialogues in Clinical Neuroscience; 2(3):203-212.
Pentchev, 1977, "Enzyme replacement therapy in Gaucher's and Fabry's disease", Ann. Clin. Lab. Sci. 7:251-253.
Pinto et al., 2004, "Prevalence of lysosomal storage diseases in Portugal", Euro. J. Hum. Gene. 12:87-92.
Poorthuis et al., 1999, "The frequency of lysosomal storage diseases in The Netherlands." Hum Genet 105:151-156.
Poulos et al., 1984, "Studies on the activation of sphingomyelinase activity in Niemann-Pick type A, B. and C fibroblasts: enzvmological differentiation of types A and a" Pediat. Res. 18:1088-1093.
Qiu et al., 2003, "Activation of human acid sphingomyelinase through modification or deletion of C-terminal cysteine." J. Biol. Chem. 278(35): 32744-32752.
Quintern et al., 1987, "Acid sphingomyelinase form human urine: purification and characterization." Biochim. Biophys. Acta 922:323-336.
Quintern et al., 1989, "Isolation of cDNA clones encoding human acid sphingomyelinase: occurrence of alternatively processed transcripts." EMBO J. 8:2469-2473.
Samulski et al., 1991, "Targeted integration of adeno-associated virus (AAV) into human chromosome 19." The EMBO J. 10(12):3941-3950.
Sando and Neufeld, 1977,"Recognition and receptor-mediated uptake of a lysosomal enzyme, alpha-I-iduronidase, by cultured human fibroblasts", Cell. 12(3):619-27.
Scaggiante et al., 1987, "Successful Therapy of Niemann-Pick Disease by Implantation of Human Amniotic Membrane." Transplantation 44(1): 59-61.
Scharfmann et al., 1991, "Long-term in-vivo expression of retrovirus-mediated gene transfer in mouse fibroblast implants." Proc. Natl. Acad. Sci. USA 88:4626-4630.
Schissel et al., 1998, "Secretory sphingomyelinase, a product of the acid sphingomyelinase gene, can hydrolyze atherogenic lipoproteins at neutral pH. Implications for atherosclerotic lesion development." J. Biol. Chem. 273: 2738-2746.
Schissel et al., 1998, "The cellular trafficking and zinc dependence of secretory and lysosomal sphingomyelinase, two products of the acid sphingomyelinase gene." J. Biol. Chem 273: 18250-18259.
Schneider and Kennedy, 1967, "Sphingomyelinase in normal human spleens and in spleens from subjects with Niemann-Pick disease", J. Lipid Res. 8:202-209.
Schuchman et al., 1989, "Isolation of a full-length cDNA encoding human acid sphingomyelinase: evidence for alternative splicing", Am. J. Hum. Genet. 4~(suppl. 4):A217.
Schuchman et al., 1991, "An MspI polymorphism in the human acid sphingomyelinase gene (SMPD1)." Nucleic Acids Research 19(11): 3160.
Schuchman et al., 1991, "Human acid sphingomyelinase. Isolation, nucleotide sequence and expression of the full-length and alternatively spliced cDNAs." J. Biol. Chem. 266: 8531-8539.
Silvia, 2000, "Infusion of recombinant human acid sphingomyelinase into Niemann-Pick disease mice leads to visceral, but not neurological, correction of the pathophysiology." Faseb J. 14:1988-1995.
Simonaro et al., 2002, "The demographics and distribution of type B Niemann-Pick disease: novel mutations lead to new genotype/phenotype correlations." Am. J. Hum. Genet. 71: 1413-1419.
Sly et al., 1981, "Role of the 6-phosphomannosyl-enzyme receptor in intracellular transport and adsorptive pinocytosis of lysosomal enzymes" Methods Cell Biol. 23:191-214.
Sly, 1981, "Prospects for enzyme replacement for lysosomal storage diseases", Birth Defects Orig Artic Ser. 17(1):201-13.
Smith and Schuchman, 2008, "The unexpected role of acid sphingomyelinase in cell death and the pathophysiology of common diseases." FASEB 22: 3419-3431.
Suchi et al., 1992, "Retroviral-mediated transfer of the human acid sphingomyelinase cDNA: correction of the metabolic defect in cultured Niemann-Pick disease cells," Proc. Natl. Acad. Sci. 89(8):3227-31.
Switzer et al., 1979, "A highly sensitive silver strain for detecting proteins and peptides in polyacrylamide gels." Anal. Biochem. 98:231-237.
Takahashi et al., 1992, "Identification and Expression of Five Mutations in the Human Acid Sphingomyelinase Gene Causing Type A and B Niemann-Pick Disease". J. Biol. Chern. 267:12552-12558.
Triggs-Raine et al., 1990, , "Screening for Carriers of Tay-Sachs Disease Among Ashkenazi Jews. A Comparison of DNA-Based and Enzyme-Based Tests." New Engl. J. Med. 323:6-12.

(56) References Cited

OTHER PUBLICATIONS

Urlaub et al., 1986, "Effect of gamma rays at the dihydrofolate reductase locus: deletions and inversions." Somat. Cell Genet., vol. 12, pp. 555-566.
Van Der Ploeg at al., 1988, "Prospect for enzyme therapy in glycogenosis II variants: a study on cultured muscle cells", J. Neurol. 235:392-396.
Van Der Ploeg et al., 1987, "Breakdown of lysosomal glycogen in cultured fibroblasts from glycogenosis type II patients after uptake of acid a-Qlucosidase", J. Neuroqical Sci. 79:327-336.
Van Der Ploeg et al., 1988, "Receptor-mediated uptake of acid alpha-glucosidase corrects lysosomal glycoqen storage in cultured skeletal muscle", Pediatr Res. Jul;24(1 ):90-4.
Vanier et al., 1993,"Deletion of Arginine (608) in Acid Sphingomyelinase is the Prevalent Mutation Among Niemann-Pick Disease Type B Patients From Northern Africa". Human Genetics 92:325-330.
Vellodi et al., 1987, "Treatment of Niemann-Pick Disease type B by allogeneic bone marrow transplantation." British Medical Journal 295:1375-1376.
Verma et al., 1991, "Human Gene Therapy." Curr. Opin in Genet & Dev. 1:54-59.
Verma, 1997, "Gene therapy—promises, problems, and prospects" Nature 389:239-242.
Wan and Schuchman, 1995, "A novel polymorphism in the human acid sphingomyelinase gene due to size variation of the signal peptide region", Biochim Biophys Acta. 1270(2-3):207-10.

Wasserstein, et al., 2010, "A Phase 1 Trial of Recombinant Human Acid Sphingomyelinase (rhASM) Enzyme Replacement Therapy in Adults with ASM Deficiency" NNPPF presentation.
Watson et al., 1992, Recombinant DNA $2^{nd}$ Edition, WH Freeman and Company, NY Chapter 12:213-234.
Watson et al., 1992, Recombinant DNA $2^{nd}$ Edition, WH Freeman and Company, NY Chapter 28:567-581.
Weiler et al., 1988, "A complementation Approach to cloning the Gene for Acid Sphingomyelinase." J cell Biol. 107:303A.
Yang et al., 2007, "Intraparenchymal injections of acid sphingomyelinase results in regional correction of lysosomal storage pathology in the Niemann-Pick A mouse" Experimental Neurology 207: 258-266.
Zhu et al., 2005, "Carboyhydrate-remodelled acid $\alpha$-glucosidase with higher affinity for the cation-independent mannose 6-phosphate receptor demonstrates improved delivery to muscles of Pompe Mice." Biochem J. 389:619-628.
Zhu et al., 2009, "Glycoengineered Acid $\alpha$-Glucosidase with Improved Efficacy at Correcting the Metabolic Aberrations an Motor Function Deficits in a mouse Model of Pompe Disease." Molec. Therap. 17(6):954-963.
Ziegler et al., 2009, "Pulmonary delivery of recombinant acid sphingomyelinase improves clearance of lysosomal sphingomyelin from the lungs of a murine model of Niemann-Pick disease." Molecular Genetics and Metabolism 97: 35-42.

* cited by examiner

Demography and Baseline Characteristics

| Cohort Number | Dose (mg/kg) | Patient ID | Age at Infusion (yr) | Gender | Age at Symptom Onset (yr) | Age at Diagnosis (yr) | Spleen Volume (X norm) | ASM Activity (% norm) |
|---|---|---|---|---|---|---|---|---|
| 1 | 0.03 | 10202 | 23 | F | 2.2 | 2.2 | 12.5 | 14 |
| | | 10401 | 21 | M | 0.5 | 8.1 | 15.1 | 25 |
| | | 10503 | 19 | M | 5.9 | 5.9 | 16.1 | 15 |
| 2 | 0.1 | 10304 | 45 | F | 38.7 | 38.7 | 4.8 | 14 |
| | | 10605 | 26 | F | 2.9 | 3.3 | 12.3 | 17 |
| | | 10906 | 41 | F | 9.6 | 9.6 | 8.7 | 29 |
| 3 | 0.3 | 10807 | 24 | M | 1.0 | 3.0 | 9.5 | 18 |
| | | 11509 | 54 | F | 53.3 | 53.3 | 6.1 | 24 |
| 4 | 0.6 | 12010 | 18 | M | Unknown | 13.9 | 8.7 | 12 |
| | | 12313 | 18 | M | 1.4 | 3.0 | 10.1 | 6 |
| 5 | 1.0 | 12112 | 46 | M | 3.5 | 3.5 | 14.5 | 6 |

Fig. 2

Treatment Emergent Adverse Events Considered Related (Possibly, Probably, or Definitely) to Treatment

| Dose (mg/kg) | Patient No. | Adverse Event | Start Day[a] | Severity | Action Taken |
|---|---|---|---|---|---|
| 0.3 | 11509 | Fever | 2 | Moderate | None |
| | | Myalgia | 2 | Moderate | None |
| | | Nausea | 2 | Moderate | None |
| | | Acute phase reaction | 2 | Moderate | None |
| 0.6 | 12010 | Leg pain | 1 | Moderate | None |
| | | Abdominal pain | 2 | Mild | None |
| | | Hip pain | 2 | Moderate | None |
| | | Acute phase reaction | 3 | Moderate | None |
| 0.6 | 12313 | Acute phase reaction | 2 | Moderate | None |
| | | Elevated bilirubin | 2 | Moderate | None |
| | | Lymphocytic infiltrate/ hepatocellular degeneration (liver biopsy) | 14 | Moderate | None |
| | | Nausea/vomiting | 1 | Moderate | Medication |
| | | Elevated bilirubin | 3 | Severe | None |
| 1.0 | 12112 | Fever | 2 | Moderate | Medication |
| | | Fatigue | 2 | Moderate | None |
| | | Acute phase reaction | 2 | Moderate | None |
| | | Urobilinogen in urine | 3 | Moderate | None |
| | | Scleral icterus | 3 | Moderate | None |
| | | Increased fibrin D-dimer | 29 | Moderate | None |

Fig. 6

DOSE ESCALATION ENZYME REPLACEMENT THERAPY FOR TREATING ACID SPHINGOMYELINASE DEFICIENCY

This application is a continuation of U.S. patent application Ser. No. 13/679,623, filed Nov. 16, 2012, now U.S. Pat. No. 8,709,408, issued Apr. 29, 2014, which is a divisional application of U.S. patent application Ser. No. 12/870,790, filed Aug. 28, 2010, now U.S. Pat. No. 8,349,319, issued Jan. 8, 2013, which claims priority to U.S. Provisional Patent Application No. 61/238,113, filed Aug. 28, 2009, the disclosures of each of which are incorporated herein by reference in their entireties.

1. INTRODUCTION

The invention relates to dose escalation enzyme replacement therapy using acid sphingomyelinase (ASM) for the treatment of human subjects having acid sphingomyelinase deficiency (ASMD), and, in particular, the non-neurological manifestations of Niemann Pick Disease (NPD), and in certain embodiments, NPD type B.

2. BACKGROUND

Acid sphingomyelinase, E.C. 3.1.4.12, (ASM) is a lysosomal phosphodiesterase enzyme that hydrolyzes sphingomyelin, a phospholipid storage substance found in the brain, liver, lungs, spleen and lymph nodes, to ceramide and phosphorylcholine. Deficiencies in ASM activity result in the inability of the body to break down sphingomyelin, causing a form of the lysosomal storage disease termed Niemann-Pick disease.

Niemann-Pick disease is an inherited autosomal recessive lipid storage disorder characterized by excessive accumulation of sphingomyelin in the lysosomes of cells such as macrophages and neurons, which impairs normal cellular function. Niemann-Pick Type A is a rapidly progressive neurodegenerative disease in infants and typically results in death within two to three years of age. Niemann-Pick Type B results in the enlargement of the liver and spleen, and respiratory distress with death generally ensuing by early adulthood. These two forms of Niemann-Pick disease which are both associated with ASM deficiencies are referred to collectively herein as Niemann-Pick disease, or ASM deficiency (ASMD). Other types of Niemann-Pick disease, e.g., Type C, do not involve mutations in the ASM gene and are not directly attributable to the function of ASM. The nature of the biochemical and molecular defects that underlie the remarkable clinical heterogeneity of the A and B subtypes remains unknown. Although patients with both subtypes have residual ASM activity (about 1 to 10% of normal), biochemical analysis cannot reliably distinguish the two phenotypes. Moreover, the clinical course of Type B NPD is highly variable, and it is not presently possible to correlate disease severity with the level of residual ASM activity.

NPD occurs more frequently among individuals of Ashkenazi Jewish ancestry than in the general population. It is estimated that the incidence of the type A disease among Ashkenazi Jews is about 1 in 40,000, a gene frequency (q) of about 1 in 200, and a heterozygote carrier frequency (2 pq) of 1 in 100 (Goodman, 1979, in "Genetic Disorders Among The Jewish People", John Hopkins Univ. Press, Baltimore, pp. 96-100). The heterozygote carrier incidence of type B NPD in the Ashkenazi Jewish population is less frequent (Goodman, supra). The combined heterozygote carrier frequency for types A and B NPD has been estimated to be about 1 in 70 among individuals of Ashkenazi Jewish decent. Although the enzymatic diagnosis of affected patients with either type A or B NPD can be made reliably (Spence and Callahan, supra), the enzymatic detection of obligate heterozygotes has proven problematic, particularly using peripheral leukocytes as the enzyme source. Presumably, the occurrence of neutral sphingomyelinases in some sources and/or the presence of residual ASM activity resulting from the mutant allele have contributed to the inability to reliably discriminate carriers for either disease subtype. Even the use of cultured skin fibroblasts, which do not express the neutral sphingomyelinase, has not provided unambiguous results with heterozygotes. In epidemiologic studies conducted in individual countries, the combined incidence of Niemann-Pick A and B disease in several countries in the world is estimated to range from 1 in 167,000 to 1 in 250,000 newborns (Miekle et al., 1999 JAMA 281(3): 249-254; Poorthuis et al., 1999 Hum Genet 105:151-156: Pinto et al., 2004 Euro. J. Hum. Gene. 12:87-92). The heterozygote carrier rate is believed to range from 1 in 200 to 1 in 250 individuals.

Enzyme replacement therapy has been used for other lysosomal storage diseases. Enzyme replacement therapy attempts to supplement the deficient enzyme activity with exogenously supplied enzyme. In the case of enzyme replacement therapy for Niemann-Pick disease, the goal would be to enable the affected individual to process sphingomyelin and avoid its buildup within the lysosomes. To be effective, such therapy initially would require a sufficiently large amount of the replacement enzyme to break down the accumulated sphingomyelin as well as continued administration of replacement enzyme to avoid further accumulation of sphingomyelin.

3. SUMMARY

The invention relates to dose escalation enzyme replacement therapy for the treatment of human subjects having ASMD—particularly subjects having non-neurological manifestations of NPD, and in particular embodiments, NPD type B. More particularly, the enzyme, ASM, is administered to such patients at an initial low, non-toxic dose that is then escalated in subsequent administrations. The highest dose of ASM tolerated by the patient can then be used as a maintenance dose. Alternatively, a therapeutically effective dose less than the highest dose tolerated can be used as a maintenance dose.

The invention is based, in part, on the discovery that doses of ASM that would be required to clear accumulated sphingomyelin substrate in human subjects, i.e., ASMD patients or Niemann-Pick patients, result in toxic side effects (including clinical signs of toxicity). This is especially surprising in the less severe form of ASMD, NPD type B patients who are deficient but have at least some enzyme activity.

More particularly, treatment of NPD would require doses high enough to achieve adequate distribution of the ASM enzyme in organs of pathology (e.g., in particular, the liver, spleen, lungs, heart, kidney and brain). Studies in an ASM knockout mouse model (ASKMO mice) showed that the majority of recombinant human ASM (rhASM) administered distributes to the liver and spleen where it reduces substrate, but to a much lesser extent in lung, heart and brain (Miranda et al. FASEB 2000, 14:1988; see also, FIG. 9B of He et al., 1999, Biochimica et Biophsyica Acta 1432: 251-264). In subsequent studies using higher doses of rhASM in the ASMKO mouse model, substrate was reduced and toxicity was not observed at doses ≤3.0 mg/kg; in fact, clinical symptoms of toxicity was not observed until doses ≥10 mg/kg were used. See, "Dose Responsive Toxicological Findings Following Intravenous Administration of Recombinant Human Acid Sphingomyelinase (rhASM) to Acid Sphingomyelinase Knock-out (ASMKO) Mice. C. Nickerson, J. Murray. A. Vitsky, M. Hawes. S. Ryan, P. Ewing, B. Thurberg, L. Andrews. Dept Pharm/Tox, Pathology, Genzyme Corp., Framingham, Mass., American Society of Human Genetics 2005; and Elevations of Pro-Inflammatory Cytokines and Decreases in Cardiovascular Hemodynamics Following Intravenous Administration of Recombinant Human Acid Sphingomyelinase (rhASM) to Acid Sphingomyelinase Knock-out (ASMKO) Mice. J. Murray, A. M. D'Angona, C. Nickerson, A. Vitsky. M. Hawes, S. Ryan, P. Ewing, B. Thurberg, L. Andrews. Dept. Pharmacology/Toxicology & Pathology, Genzyme Corp., Framingham, Mass., Society of Toxicology 2006.

Based on these ASKMO data, we treated non-neuronopathic ASMD human subjects with a conservative maximum dose of 1.0 mg/kg rhASM as described in Section 6, infra. Quite unexpectedly, toxicity in the human subjects, including the onset of related adverse events with clinical symptoms, was observed using doses as low as 0.3 mg/kg! This result was especially surprising, since the ASM enzyme is absent in the knock out mouse model which should reflect a more severe condition than in these human subjects having at least some enzyme activity and relatively mild disease.

While not intended to be bound by any theory, the toxic side effects that occur with ASM treatment may result from breakdown of stored sphingomyelin substrate in the ASMD patient and release of the product, ceramide that is pro-apoptotic and induces a pro-inflammatory cytokine response and hyperbilirubinemia. To address this issue, we have developed a regimen to allow for the safe administration of high doses of the ASM enzyme required to achieve adequate distribution in organs of pathology. In accordance with this regimen, initial treatment with ASM at very low doses is used to achieve a slow degradation of the stored substrate which is accompanied by fewer side effects. As the substrate is depleted in the subject (as the storage substrate is "debulked"), the dose can be escalated safely.

In accordance with this protocol, a low, non-toxic dose of the ASM enzyme is initially administered to a NPD disease patient and the dose is escalated over time. As the dose of the ASM enzyme is escalated, the patient can be monitored for total bilirubin concentration, the production of acute phase reactants, the production of inflammatory mediators, and related adverse events. The administration of a low dose of ASM and the escalation of the dose facilitates the debulking of the accumulated sphingomyelin. Once the patient is debulked, higher doses may be safely administered to the patient to ensure adequate distribution of the ASM enzyme to target organs (e.g., liver, spleen, lungs, heart, kidney, brain, bone marrow, skeleton, joints, etc.). In certain embodiments, the maximum dose tolerated by the patient can be used as the maintenance dose. In some embodiments, based upon a patient's condition, the maintenance dose may be increased or decreased over time.

In certain embodiments, treatment of the patient is monitored by measuring the plasma sphingomyelin levels, plasma ceramide levels, the production of "acute phase reactants" and inflammatory mediators that are a measure of inflammatory responses, bilirubin concentrations (total, direct, and indirect), and/or other biochemical markers to ensure a stable response before elevating the dose to the next level. These markers include, but are not limited to C-reactive protein (CRP) or high sensitivity CRP (hs-CRP), cytokines (e.g. IL-8, IL-6), calcitonin and ferritin. In specific embodiments, the patient may be monitored for one or more related adverse events, which may include, but are not limited to, constitutional symptoms (e.g., fever, nausea, vomiting, pain, myalgia) and jaundice.

Doses less than 1 mg/kg are preferable for initiating treatment. The initial dose is successively elevated until a therapeutic dose is achieved. Such dose escalation can be used to determine the highest tolerated dose. For example, once the patient is debulked of the accumulated sphingomyelinase substrate, the dose may be further escalated until toxicity is observed. The maintenance dose can be adjusted accordingly, and can be continually and periodically readjusted depending on the status of the patient.

In a specific embodiment, a method for treating a human subject having an acid sphingomyelinase deficiency, comprises: (a) a regimen for debulking accumulated sphingomyelin substrate in the human subject comprising: (i) administering an initial low non-toxic dose of ASM to the human subject; (ii) administering successively higher doses of ASM to the human subject, and monitoring the subject for one or more adverse side effects after each successive dose as indicated by elevated bilirubin or a related adverse event; and (b) a maintenance regimen comprising administering a dose equal to or less than the highest dose tolerated by the subject as the maintenance dose for the subject.

In another specific embodiment, a method for treating a human subject having an acid sphingomyelinase deficiency, comprises administering rhASM in an escalating dose regimen at the following sequential doses: 0.1 mg/kg; 0.3 mg/kg; 0.6 mg/kg; and 1.0 mg/kg, wherein each dose of rhASM is administered at least twice, and each dose is administered at two week intervals, and wherein the patient is monitored for toxic side effects before elevating the dose to the next level.

In another specific embodiment, described herein is an acid sphingomyelinase (ASM) for use in the treatment of an acid sphingomyelinase deficiency in a human subject prepared to be administered: (a) in a regimen for debulking accumulated sphingomyelin substrate comprising: (i) administration of an initial low non-toxic dose of acid sphingomyelinase (ASM); (ii) administration of successively higher doses of ASM, and monitoring the subject for one or more adverse side effects after each successive dose as indicated by elevated bilirubin or a related adverse event; and (b) in a maintenance regimen comprising administration of a dose equal to or less than the highest dose tolerated by the subject as the maintenance dose for the subject.

In another specific embodiment, described herein is a recombinant human ASM for use in the treatment of an acid sphingomyelinase deficiency in a human subject prepared to be administered in an escalating dose regimen at the following sequential doses: 0.1 mg/kg; 0.3 mg/kg; 0.6 mg/kg; and 1.0 mg/kg, wherein each dose of is administered at least twice, and each dose is administered at two week intervals, and wherein the subject is monitored for toxic side effects before elevating the dose to the next level.

3.1. Terminology

As used herein, the terms "about" and "approximately" are used interchangeably in the context of a given value to refer to a range around a given value, wherein the resulting value is substantially the same as the expressly recited value. In a specific embodiment "about" means within 10%, 15%, 25% of a given value or range.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human infant" refers to a newborn to 1 year old year human.

As used herein, the term "human toddler" refers to a human that is 1 year to 3 years old.

As used herein, the term "adverse event" refers to "any untoward medical occurrence in a patient or clinical investigation subject administered a pharmaceutical product" as defined in the Clinical Data Interchange Standards Consortium Study Data Tabulation Model standard terminology v. 3.1.1. A "related adverse event" is an adverse event that has a casual relationship with treatment.

As used herein, the term "maintenance dose(s)" and the like refers to a dosage administered to ASMD patients to maintain the desired therapeutic effect. In specific embodiments, the maintenance dose(s) maintains one, two, three, four or more the following desired therapeutic effects: (i) a reduction in spleen volume as assessed by techniques known in the art. e.g., MRI; (ii) a reduction in liver sphingomyelin levels as assessed by techniques known in the art, e.g., biochemical analysis and/or histomorphometric analysis of liver samples; (iii) an increase in exercise capacity as assessed by techniques known in the art, e.g., maximum workload by cycle erogmetry, including percent predicted maximum workload, peak oxygen consumption and carbon dioxide production; (iv) an increase in pulmonary function as assessed by techniques known in the art, e.g., techniques described in American Thoracic Society, 1991, Am. Rev. Respir. Dis. 144: 1202-1218, such as diffusing capacity (DLco), percent predicted forced vital capacity (FVC) as measured by, e.g., spirometric techniques, forced expiratory volume within 1 second ($FEV_1$) as measured by, e.g., spirometric techniques, and total lung capacity: (v) a decrease in bronchial alveolar lavage (BAL) sphingomyelin; (vi) a decrease in liver volume as assessed by techniques known in the art, e.g., MRI: (vii) an improvement in lung appearance as assessed by techniques known in the art, e.g., high resolution computed tomography (CT) scan or chest X-ray; (viii) a decrease in sphinomyelin concentration in the liver, skin, plasma and dried blood spot (DBS) as measured by, e.g., tandem mass spectrometry; (ix) a reduction or the amelioration of the severity of ASMD and/or a symptom associated therewith; (x) a reduction in the duration of a symptom associated with ASMD; (xi) the prevention in the recurrence of a symptom associated with ASMD; (xii) a reduction in hospitalization of a subject; (vi) a reduction in hospitalization length; (xiii) an increase in the survival of a subject; (xiv) a reduction in mortality; (xv) a decrease in hospitalization rate; (xvi) a reduction in the number of symptoms associated with ASMD; (xvii) an increase in symptom-free survival of ASMD patients; (xviii) an improvement in neurological function (e.g., psychomotor function, social responsiveness, etc.); (xix) an improvement in lung clearance as measured by, e.g., BAL cell count and profile; (xx) a decrease in serum levels of chitotriosidase; (xxi) a decrease in serum levels of chemokine (c-c) motif ligand 18 (CCL18); (xxii) an improvement in lipid profile (e.g., HDL, LDL, cholesterol, triglycerides, and total cholesterol:HDL ratio); and (xxiii) improved quality of life as assessed by, e.g., a questionnaire. In certain embodiments, the maintenance dose is the highest or maximum dose tolerated by a patient.

In some embodiments, the maintenance dose is a dose of between 0.5 mg/kg to 1.5 mg/kg, 0.75 mg/kg to 1.25 mg/kg, 1 mg/kg to 2.5 mg/kg, 1 mg/kg to 2.75 mg/kg, 1.5 mg/kg to 2.5 mg/kg, 1.5 mg/kg to 2.75 mg/kg, 2 mg/kg to 2.5 mg/kg, 2 mg/kg to 2.75 mg/kg, 2.5 mg/kg to 2.75 mg/kg, 2.5 mg/kg to 3 mg/kg, 3 mg/kg to 4 mg/kg, 3 mg/kg to 5 mg/kg, 4 mg/kg to 5 mg/kg, 2 mg/kg to 5 mg/kg or 5 mg/kg to 10 mg/kg of ASM.

In certain embodiments, the maintenance dose is a dose of between 5 mg/kg to 15 mg/kg, 10 mg/kg to 15 mg/kg. 10 mg/kg to 20 mg/kg, 15 mg/kg to 20 mg/kg, 20 mg/kg to 30 mg/kg, 25 mg/kg to 50 mg/kg. 30 mg/kg to 40 mg/kg, 30 mg/kg to 45 mg/kg or 40 mg/kg to 50 mg/kg of ASM. In some embodiments, the maintenance dose is 0.75 mg/kg, 0.80 mg/kg, 0.85 mg/kg, 0.90 mg/kg, 0.95 mg/kg, 1 mg/kg, 1.1 mg/kg, 1.2 mg/kg, 1.25 mg/kg, 1.3 mg/kg, 1.4 mg/kg, 1.5 mg/kg, 1.75 mg/kg, or 2 mg/kg of ASM. In certain embodiments, the maintenance dose is 2.5 mg/kg, 2.75 mg/kg, 3 mg/kg, 3.25 mg/kg, 3.5 mg/kg, 3.75 mg/kg, 4 mg/kg, 4.25 mg/kg, 4.5 mg/kg, 4.75 mg/kg, 5 mg/kg. 5.5 mg/kg, 6 mg/kg, 6.5 mg/kg, 7 mg/kg, 7.5 mg/kg. 8 mg/kg, 8.5 mg/kg, 9 mg/kg. 9.5 mg/kg or 10 mg/kg of ASM. In some embodiments, the maintenance does is 11 mg/kg, 12 mg/kg, 13 mg/kg, 14 mg/kg, 15 mg/kg, 20 mg/kg, 25 mg/kg, 30 mg/kg, 35 mg/kg, 40 mg/kg, 45 mg/kg or 50 mg/kg of ASM. In some embodiments, the maintenance dose is at least 1 mg/kg, at least 2 mg/kg, at least 3 mg/kg, at least 4 mg/kg, at least 5 mg/kg, at least 6 mg/kg, at least 7 mg/kg, at least 8 mg/kg of ASM with the highest dose being 10 mg/kg of ASM. In certain embodiments, the maintenance dose is at least 10 mg/kg, at least 15 mg/kg, at least 20 mg/kg, at least 25 mg/kg, at least 30 mg/kg, or at least 35 mg/kg of ASM with the highest dose being 50 mg/kg.

As used herein, the term "non-toxic dose(s)" and the like refers to a dosage administered to ASMD patients without resulting in one, two, three or all of the following: (i) a moderate or severe related adverse event as defined by a clinical symptom that interferes with normal daily functioning and requires additional monitoring, intervention, or treatment, or, an abnormal laboratory value or procedural result of clinical concern that requires further monitoring, treatment, or investigation. See, e.g., the Clinical Data Interchange Standards Consortium Study Data Tabulation Model standard terminology v.3.1.1; (ii) a total bilirubin value of greater than 1.5 mg/dL, 1.75 mg/dL, 2.0 mg/dL, 2.1 mg/dL, 2.2 mg/dL, 2.3 mg/dL, 2.4 mg/dL, 2.5 mg/dL, 2.6 mg/dL, 2.7 mg/dL, 2.75 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL or 4 mg/dL or in the range of 2.1 mg/dL to 2.5 mg/dL, 2.1 mg/dL to 3.0 mg/dL, or 2.1 mg/dL to 4 mg/dL that lasts for greater than 18 hours, 24 hours, 36 hours, 48 hours or 72 hours, 5 days, one week, two weeks or three weeks after administration of the dose of ASM; (iii) a plasma ceramide concentration of greater than 8.2 µg/mL, 8.3 µg/mL, 8.4 µg/mL, 8.5 µg/mL, 8.75 µg/mL, 9 µg/mL, 9.5 µg/mL, 10 µg/mL, 11 µg/mL, 12 µg/mL, 13 µg/mL, 14 µg/mL, 15 µg/mL, 16 µg/mL, 17 µg/mL, 18 µg/mL, 19 µg/mL, 20 µg/mL, 25 µg/mL, 30 µg/mL, 35 µg/mL, 40 µg/mL, 45 µg/mL, 50 µg/mL, 55 µg/mL, 60 µg/mL, 65 µg/mL, 70 µg/mL, 75 µg/mL, or 80 µg/mL, or in the range of 8.2 µg/mL to 10 µg/mL, 8.5 µg/mL to 10 µg/mL, 9 µg/mL to 12 µg/mL, 10 µg/mL to 12 µg/mL, 10 µg/mL to 15 µg/mL, 10 µg/mL to 20 µg/mL, 15 µg/mL to 20 µg/mL, or 20 µg/mL to 30 µg/mL 6 hours, 8 hours, 10 hours, 12 hours, 16 hours, 18 hours, 24 hours, 36 hours, 48 hours or 72 hours after administration of the dose of ASM; or (iv) an acute phase response/reaction. The "non-toxic dose" of ASM may vary depending upon, e.g., the stability of the enzyme used, the activity of the enzyme used, and/or the route of administration of the enzyme. For example, the dose of a modified ASM enzyme with increased activity may be lower than the dosage of an unmodified ASM. One skilled in the art would be able to adjust the dose of enzyme administered based on the stability of the enzyme, the activity of the enzyme, and/or the route of administration of the enzyme.

An acute phase reaction is an early reaction (generally, e.g., within 12 to 72 hours) following administration of ASM that is indicative of an inflammatory response. An acute phase response can be assessed by a change in the concentration of an acute phase reactant (such as, e.g. CRP/hs-CRP, ferritin, fibrinogen, iron or transferrin), a change in the percentage of neutrophils, a change in prothrombin time, or a change in partial thromboplastin time. In a specific embodiment, an increase in CRP/hs-CRP concentration 6 hours, 8 hours, 12 hours, 18 hours, 24 hours, 36 hours, 48 hours or 72 hours after administration of a dose of ASM relative to a patient's CRP/hs-CRP concentration prior to administration of ASM can be utilized as a measurement of an acute phase response. In another specific embodiment, a plasma CRP/hs-CRP concentration that is greater than the normal plasma CRP/hs-CRP concentration 6 hours, 8 hours, 12 hours, 16 hours, 18 hours, 24 hours, 36 hours, 48 hours or 72 hours after administration of the dose of ASM can be utilized as a measurement of an acute phase response. In certain embodiments, a plasma CRP/hs-CRP concentration of greater than approximately 8.1 mg/L, 8.2 mg/L, 8.3 mg/L, 8.4 mg/L. 8.5 mg/L, 9 mg/L, 9.5 mg/L. 10 mg/L, 11 mg/L, or 12 mg/L, or in the range of 8.5 mg/L to 10 mg/L, or 8.5 mg/dL to 12 mg/L, or 10 mg/L to 12 mg/L 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in ferritin concentration 6 hours, 8 hours, 12 hours, 16 hours, 18 hours, 24 hours, 36 hours, 48 hours or 72 hours after administration of a dose of ASM relative to a patient's ferritin concentration prior to administration of ASM can be used as a measurement of an acute phase response. In another specific embodiment, a plasma ferritin concentration that is greater than the normal plasma ferritin concentration 6 hours, 8 hours, 12 hours, 18 hours, 24 hours, 36 hours, 48 hours or 72 hours after administration of the dose of ASM can be used as a measurement of an acute phase response. In certain embodiments, a plasma ferritin concentration of greater than approximately 300 ng/mL, 325 ng/mL, 350 ng/mL, 375 ng/mL, 400 ng/mL, 425 ng/mL, 450 ng/mL, 475 ng/mL, 500 ng/mL, 525 ng/mL, 550 ng/mL, 575 ng/mL, 600 ng/mL, 625 ng/mL, 650 ng/mL, 675 ng/mL, 700 ng/mL, 725 ng/mL, 750 ng/mL, 775 ng/mL, 800 ng/mL, 850 ng/mL, 900 ng/mL, 950 ng/mL, 1000 ng/mL, 1050 ng/mL, 1100 ng/mL, 1150 ng/mL, or 1200 ng/mL or in the range of 600 ng/mL to 800 ng/mL, 650 ng/mL to 850 ng/mL, 600 ng/mL to 1000 ng/mL, 600 ng/mL to 1200 ng/mL, 800 ng/mL to 1000 ng/mL, 900 ng/mL to 1000 ng/mL, or 1000 ng/mL to 1200 ng/mL 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in plasma or serum IL-8 concentration 6 hours, 8 hours, 12 hours, 16 hours, 18 hours, 24 hours, 36 hours, 48 hours or 72 hours after administration of a dose of ASM relative to a patient's IL-8 concentration prior to administration of ASM can be used as a measurement of an acute phase response. In another specific embodiment, a plasma or serum IL-8 concentration that is greater than the normal plasma IL-8 concentration 6 hours, 8 hours, 12 hours, 18 hours, 24 hours, 36 hours, 48 hours or 72 hours after administration of the dose of ASM can be used as a measurement of an acute phase response. In certain embodiments, a plasma 1-8 concentration of greater than approximately 24 pg/mL, 50 pg/mL, 75 pg/mL, 100 pg/mL, 200 pg/mL, 300 pg/mL, 400 pg/mL, 500 pg/mL, 600 pg/mL, 700 pg/mL, 800 pg/mL, or 900 pg/mL, 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in plasma or serum IL-6 concentration 6 hours, 8 hours, 12 hours, 16 hours, 18 hours, 24 hours, 36 hours, 48 hours or 72 hours after administration of a dose of ASM relative to a patient's IL-6 concentration prior to administration of ASM can be used as a measurement of an acute phase response. In another specific embodiment, a plasma or serum IL-6 concentration that is greater than the normal plasma or serum IL-6 concentration 6 hours, 8 hours, 12 hours, 18 hours, 24 hours, 36 hours, 48 hours or 72 hours after administration of the dose of ASM can be used as a measurement of an acute phase response. In certain embodiments, a plasma IL-6 concentration of greater than approximately 4.4 pg/mL, 6 pg/mL, 8 pg/mL, 10 pg/mL, 15 pg/mL, 20 pg/mL, 25 pg/mL, or 30 pg/mL, 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in plasma or serum calcitonin concentration 6 hours, 8 hours, 12 hours, 16 hours, 18 hours, 24 hours, 36 hours, 48 hours or 72 hours after administration of a dose of ASM relative to a patient's calcitonin concentration prior to administration of ASM can be used as a measurement of an acute phase response. In another specific embodiment, a plasma or serum calcitonin concentration that is greater than the normal plasma calcitonin concentration 6 hours, 8 hours, 12 hours, 18 hours, 24 hours, 36 hours, 48 hours or 72 hours after administration of the dose of ASM can be used as a measurement of an acute phase response. In certain embodiments, a plasma calcitonin concentration of greater than approximately 9.4 pg/mL, 20 pg/mL, 30 pg/mL, 40 pg/mL, 50 pg/mL, 75 pg/mL, 100 pg/mL, 150 pg/mL, 200 pg/mL, or 250 pg/mL, 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in fibrinogen concentration 6 hours, 8 hours, 12 hours, 16 hours, 18 hours, 24 hours, 36 hours, 48 hours or 72 hours after administration of a dose of ASM relative to a patient's fibrinogen concentration prior to administration of ASM can be used as a measurement of an acute phase response. In another specific embodiment, a plasma fibrinogen concentration that is greater than the normal plasma fibrinogen concentration 6 hours, 8 hours, 12 hours, 16 hours, 18 hours, 24 hours, 36 hours, 48 hours or 72 hours after administration of the dose of ASM can be used as a measurement of an acute phase response. In certain embodiments, a plasma fibrinogen concentration of greater than approximately 350 mg/dL, 375 mg/dL, 400 mg/dL, 425 mg/dL, or 450 mg/dL, or in the range of 350 mg/dL to 400 mg/dL, 350 mg/dL to 450 mg/dL or 400 mg/dL to 450 mg/dL 6 hours, 8 hours, 12 hours, 16 hours, 18 hours, 24 hours, 36 hours, 48 hours or 72 hours after administration of the dose of ASM can be used as a measurement of an acute phase response.

In one embodiment, an increase in the percentage of neutrophils of total white blood cells 6 hours, 8 hours, 12 hours, 16 hours, 18 hours, 24 hours, 36 hours, 48 hours or 72 hours after administration of a dose of ASM relative to a patient's percentage of neutrophils of total white blood cells prior to administration of ASM can be utilized as a measurement of an acute phase response. In another embodiment, an increase in the percentage of neutrophils of total white blood cells that is greater than the normal percentage of neutrophils of total white blood cells concentration 6 hours, 8 hours, 12 hours, 16 hours, 18 hours, 24 hours, 36 hours, 48 hours or 72 hours after administration of the dose of ASM can be utilized as a measurement of an acute phase response. In certain embodiments, an increase in the percentage of neutrophils of total white blood cells that is 70%, 75%, 80%, 85%, 90%, 95% or greater 6 hours, 8 hours, 12 hours, 16 hours, 18 hours, 24 hours, 36 hours, 48 hours or 72 hours after administration of the dose of ASM can be utilized as a measurement of an acute phase response.

As used herein, the term "low, non-toxic dose(s)" and the like in the context of the initial dose or doses administered to a subject refers to a dosage that is the first dose or doses of ASM administered to a subject to treat ASMD that is non-toxic. In certain embodiments, a low, non-toxic dose(s) is a dose of 0.001 mg/kg to 0.01 mg/kg, 0.001 mg/kg to 0.01 mg/kg, 0.001 mg/kg to 0.05 mg/kg, 0.001 mg/kg to 0.1 mg/kg, 0.001 mg/kg to 0.5 mg/kg, 0.05 mg/kg to 0.275 mg/kg, 0.075 mg/kg to 0.275 mg/kg, 0.05 mg/kg to 0.2 mg/kg, 0.075 mg/kg to 0.2 mg/kg, 0.1 mg/kg to 0.275 mg/kg, 0.1 mg/kg to 0.25 mg/kg, 0.1 mg/kg to 1 mg/kg. 0.5 mg/kg to 1 mg/kg, 0.75 mg/kg to 1 mg/kg, 0.1 mg/kg to 2 mg/kg, 0.5 mg/kg to 2 mg/kg, 0.75 mg/kg to 2 mg/kg, 1 mg/kg to 2 mg/kg or 1.25 mg/kg to 2 mg/kg, 1.5 mg/kg to 2 mg/kg or 1.75 mg/kg to 2 mg/kg of ASM. In some specific embodiments, a low, non-toxic dose is a dose of 0.001 mg/kg, 0.005 mg/kg, 0.0075 mg/kg, 0.01 mg/kg, 0.0125 mg/kg, 0.025 mg/kg, 0.05 mg/kg, 0.075 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.4 mg/kg. 0.5 mg/kg, 0.6 mg/kg, 0.7 mg/kg, 0.75 mg/kg. 0.8 mg/kg, 0.9 mg/kg or 1 mg/kg of ASM.

The terms "subject" and "patient" are used herein interchangeably to refer to a human. In a specific embodiment, the human has or has been diagnosed as having an ASMD.

As used herein, the term "therapeutically effective" in the context of administering a dose of ASM to a subject refers to the amount of ASM that results in a beneficial or therapeutic effect. In specific embodiments, the term "therapeutically effective" in context of administering a dose of ASM to a subject refers to the amount of ASM refers which is sufficient to achieve at least one, two, three, four or more of the following effects: (i) a reduction in spleen volume as assessed by techniques known in the art, e.g., MRI; (ii) a reduction in liver sphingomyelin levels as assessed by techniques known in the art. e.g., biochemical analysis and/or histomorphometric analysis of liver samples: (iii) an increase in exercise capacity as assessed by techniques known in the art, e.g., maximum workload by cycle erogmetry, including percent predicted maximum workload, peak oxygen consumption and carbon dioxide production: (iv) an increase in pulmonary function as assessed by techniques known in the art, e.g., techniques described in American Thoracic Society, 1991, Am. Rev. Respir. Dis. 144: 1202-1218, such as diffusing capacity (DLco), percent predicted forced vital capacity (FVC) as measured by, e.g., spirometric techniques, forced expiratory volume within 1 second ($FEV_1$) as measured by, e.g., spirometric techniques, and total lung capacity; (v) a decrease in bronchial alveolar lavage (BAL) sphingomyelin; (vi) a decrease in liver volume as assessed by techniques known in the art, e.g., MRI: (vii) an improvement in lung appearance as assessed by techniques known in the art, e.g., high resolution CT scan or chest X-ray; (viii) a decrease in sphinomyelin concentration in the skin, plasma and dried blood spot (DBS) as measured by, e.g., tandem mass spectrometry; (ix) a reduction or the amelioration of the severity of ASMD and/or a symptom associated therewith; (x) a reduction in the duration of a symptom associated with ASMD; (xi) the prevention in the recurrence of a symptom associated with ASMD; (xii) a reduction in hospitalization of a subject; (vi) a reduction in hospitalization length; (xiii) an increase in the survival of a subject; (xiv) a reduction in mortality; (xv) a decrease in hospitalization rate; (xvi) a reduction in the number of symptoms associated with ASMD; (xvii) an increase in symptom-free survival of ASMD patients; (xviii) an improvement in neurological function (e.g., psychomotor function, social responsiveness, etc.); (xix) an improvement in lung clearance as measured by, e.g., BAL cell count and profile; (xx) a decrease in serum levels of chitotriosidase; (xxi) a decrease in serum levels of CCL18; (xxii) an improvement in lipid profile (e.g., HDL, LDL, cholesterol, triglycerides, and total cholesterol:HDL ratio); and (xxiii) improved quality of life as assessed by, e.g., a questionnaire.

As used herein, the terms "therapies" and "therapy" can refer to any protocol(s), method(s), compositions, formulations, and/or agent(s) that can be used in the treatment, management, or amelioration of ASMD or condition or symptom associated therewith. In certain embodiments, the terms "therapies" and "therapy" refer to biological therapy, supportive therapy, and/or other therapies useful in treatment, management, prevention, or amelioration of ASMD or condition or symptom associated therewith. In embodiments, the term "therapy" refers to a therapy that does one, two or more of the following: (i) enhances the delivery of ASM to sites of pathology, (ii) enhances the activity of ASM, and (iii) enhances the stability of ASM. In certain embodiments, the term "therapy" refers to a therapy other than ASM. In specific embodiments, an "additional therapy" and "additional therapies" refer to a therapy other than ASM.

As used herein, the term "toxic effect(s)" and the like refers one, two, three or all of the following subsequent to the administration of a dose(s) of ASM: (i) a moderate or severe related adverse event as defined by a clinical symptom that interferes with normal daily functioning and requires additional monitoring, intervention, or treatment, or, an abnormal laboratory value or procedural result of clinical concern that requires further monitoring, treatment, or investigating. See, e.g., the Clinical Data Interchange Standards Consortium Study Data Tabulation Model standard terminology v.3.1.1; (ii) a total bilirubin value of greater than 1.5 mg/dL, 1.75 mg/dL, 2.0 mg/dL, 2.1 mg/dL, 2.2 mg/dL, 2.3 mg/dL, 2.4 mg/dL, 2.5 mg/dL, 2.6 mg/dL, 2.7 mg/dL, 2.75 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL or 4 mg/dL or in the range of 2.1 mg/dL to 2.5 mg/dL, 2.1 mg/dL to 3.0 mg/dL, or 2.1 mg/dL to 4 mg/dL that lasts for greater than 16 hours, 18 hours, 24 hours, 36 hours, 48 hours or 72 hours, 5 days, one week, two weeks or three weeks after administration of the dose of ASM; (iii) a plasma ceramide concentration of greater than 8.2 µg/mL, 8.3 µg/mL, 8.4 µg/mL, 8.5 µg/mL, 8.75 µg/mL, 9 µg/mL, 9.5 µg/mL, 10 µg/mL, 11 µg/mL, 12 µg/mL, 13 µg/mL, 14 µg/mL, 15 µg/mL, 16 µg/mL, 17 µg/mL, 18 µg/mL, 19 µg/mL, 20 µg/mL, 25 µg/mL, 30 µg/mL, 35 µg/mL, 40 µg/mL, 45 µg/mL, 50 µg/mL, 55 µg/mL, 60 µg/mL, 65 µg/mL, 70 µg/mL, 75 µg/mL, or 80 µg/mL, or in the range of 8.2 µg/mL to 10 µg/mL, 8.5 µg/mL to 10 µg/mL, 9 µg/mL to 12 µg/mL, 10 µg/mL to 12 µg/mL, 10 µg/mL to 15 µg/mL, 10 µg/mL to 20 µg/mL, 15 µg/mL to 20 µg/mL, or 20 µg/mL to 30 µg/mL 6 hours, 8 hours, 10 hours, 12 hours, 16 hours, 18 hours, 24 hours, 36 hours, 48 hours or 72 hours after administration of the dose of ASM; or (iv) an acute phase response.

An acute phase response can be assessed by a change in the concentration of an acute phase reactant (such as, e.g., C-reactive protein, ferritin, albumin, IL-8, Il-6, calcitonin, fibrinogen, iron or transferrin), a change in the percentage of neutrophils, a change in prothrombin time, or a change in partial thromboplastin time. In a specific embodiment, an increase in CRP/hs-CRP concentration 6 hours, 8 hours, 12 hours, 18 hours, 24 hours, 36 hours, 48 hours or 72 hours after administration of a dose of ASM relative to a patient's CRP/hs-CRP concentration prior to administration of ASM can be utilized as a measurement of an acute phase response. In another specific embodiment, a plasma CRP/hs-CRP concentration that is greater than the normal plasma CRP/hs-CRP concentration 6 hours, 8 hours, 12 hours, 16 hours, 18 hours, 24 hours, 36 hours, 48 hours or 72 hours after administration of the dose of ASM can be utilized as a measurement of an acute phase response. In certain embodiments, a plasma CRP/hs-CRP concentration of greater than approximately 8.1 mg/L, 8.2 mg/L, 8.3 mg/L, 8.4 mg/L, 8.5 mg/L, 8.6 mg/L, 8.7 mg/L, 8.8 mg/L, 8.8 mg/dL, 8.9 mg/L, 9 mg/L, 9.5 mg/L, 10 mg/L, 11 mg/L, or 12 mg/L, or in the range of 8.5 mg/L to 10 mg/L, or 8.5 mg/L to 12 mg/L, or 10 mg/L to 12 mg/L 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in ferritin concentration 6 hours, 8 hours, 12 hours, 16 hours, 18 hours, 24 hours, 36 hours, 48 hours or 72 hours after administration of a dose of ASM relative to a patient's ferritin concentration prior to administration of ASM can be used as a measurement of an acute phase response. In another specific embodiment, a plasma ferritin concentration that is greater than the normal plasma ferritin concentration 6 hours, 8 hours, 12 hours, 18 hours, 24 hours, 36 hours, 48 hours or 72 hours after administration of the dose of ASM can be used as a measurement of an acute phase response. In certain embodiments, a plasma ferritin concentration of greater than approximately 600 ng/mL, 625 ng/mL, 650 ng/mL, 675 ng/mL, 700 ng/mL, 725 ng/mL, 750 ng/mL, 775 ng/mL, 800 ng/mL, 850 ng/mL, 900 ng/mL, 950 ng/mL, 1000 ng/mL, 1050 ng/mL, 1100 ng/mL, 1150 ng/mL, or 1200 ng/mL or in the range of 600 ng/mL to 800 ng/mL, 650 ng/mL to 850 ng/mL, 600 ng/mL to 1000 ng/mL, 600 ng/mL to 1200 ng/mL, 800 ng/mL to 1000 ng/mL, 900 ng/mL to 1000 ng/mL, or 1000 ng/mL to 1200 ng/mL 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in fibrinogen concentration 6 hours, 8 hours, 12 hours, 16 hours, 18 hours, 24 hours, 36 hours, 48 hours or 72 hours after administration of a dose of ASM relative to a patient's fibrinogen concentration prior to administration of ASM can be used as a measurement of an acute phase response. In another specific embodiment, a plasma fibrinogen concentration that is greater than the normal plasma fibrinogen concentration 6 hours, 8 hours, 12 hours, 16 hours, 18 hours, 24 hours, 36 hours, 48 hours or 72 hours after administration of the dose of ASM can be used as a measurement of an acute phase response. In certain embodiments, a plasma fibrinogen concentration of greater than approximately 350 mg/dL, 375 mg/dL, 400 mg/dL, 425 mg/dL, or 450 mg/dL, or in the range of 350 mg/dL to 400 mg/dL, 350 mg/dL to 450 mg/dL or 400 mg/dL to 450 mg/dL 6 hours, 8 hours, 12 hours, 16 hours. 18 hours, 24 hours, 36 hours, 48 hours or 72 hours after administration of the dose of ASM can be used as a measurement of an acute phase response.

In a specific embodiment, a decrease in albumin concentration 6 hours, 8 hours, 12 hours, 18 hours, 24 hours, 36 hours, 48 hours or 72 hours after administration of a dose of ASM relative to a patient's albumin concentration prior to administration of ASM can be utilized as a measurement of an acute phase response. In certain embodiments, a decrease in the following magnitude of albumin concentration of 0.2, 0.4, 0.6, 1, 1.5, 2.0 g/dL from a normal range of 3.5 to 5.0 g/dL 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, a decrease in ferritin concentration 6 hours, 8 hours, 12 hours, 18 hours, 24 hours, 36 hours, 48 hours or 72 hours after administration of a dose of ASM relative to a patient's ferritin concentration prior to administration of ASM can be utilized as a measurement of an acute phase response. In certain embodiments, a decrease in the following magnitude of ferritin concentration of 20, 40, 60, 80, 100, 120, 140, 160 mcg/dL from a normal range of 60 to 170 mcg/dL 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, a decrease in transferrin concentration 6 hours, 8 hours, 12 hours, 18 hours, 24 hours, 36 hours, 48 hours or 72 hours after administration of a dose of ASM relative to a patient's transferrin concentration prior to administration of ASM can be utilized as a measurement of an acute phase response. In certain embodiments, a decrease in the following magnitude of transferrin concentration of 20, 40, 60, 80, 100, 120, 140, 160, 180 mg/dL from a normal range of 202 to 336 mg/dL 6 hours, 8 hours, 12 hours, 16 hours, 18 hours, 24 hours, 36 hours, 48 hours or 72 hours after administration of the dose of ASM can be used as a measurement of an acute phase response.

In one embodiment, an increase in the percentage of neutrophils of total white blood cells 6 hours, 8 hours, 12 hours, 16 hours, 18 hours, 24 hours, 36 hours, 48 hours or 72 hours after administration of a dose of ASM relative to a patient's percentage of neutrophils of total white blood cells prior to administration of ASM can be utilized as a measurement of an acute phase response. In another embodiment, an increase in the percentage of neutrophils of total white blood cells that is greater than the normal percentage of neutrophils of total white blood cells concentration 6 hours, 8 hours, 12 hours, 16 hours, 18 hours, 24 hours, 36 hours, 48 hours or 72 hours after administration of the dose of ASM can be utilized as a measurement of an acute phase response. In certain embodiments, an increase in the percentage of neutrophils of total white blood cells that is 70%, 75%, 80%, 85%, 90%, 95% or greater 6 hours, 8 hours, 12 hours, 16 hours, 18 hours, 24 hours, 36 hours, 48 hours or 72 hours after administration of the dose of ASM can be utilized as a measurement of an acute phase response.

4. BRIEF DESCRIPTION OF THE DRAWINGS

FIG. 2 is a chart showing the demography and baseline characteristics of the patients enrolled in the protocol described below.

Figure 3A:
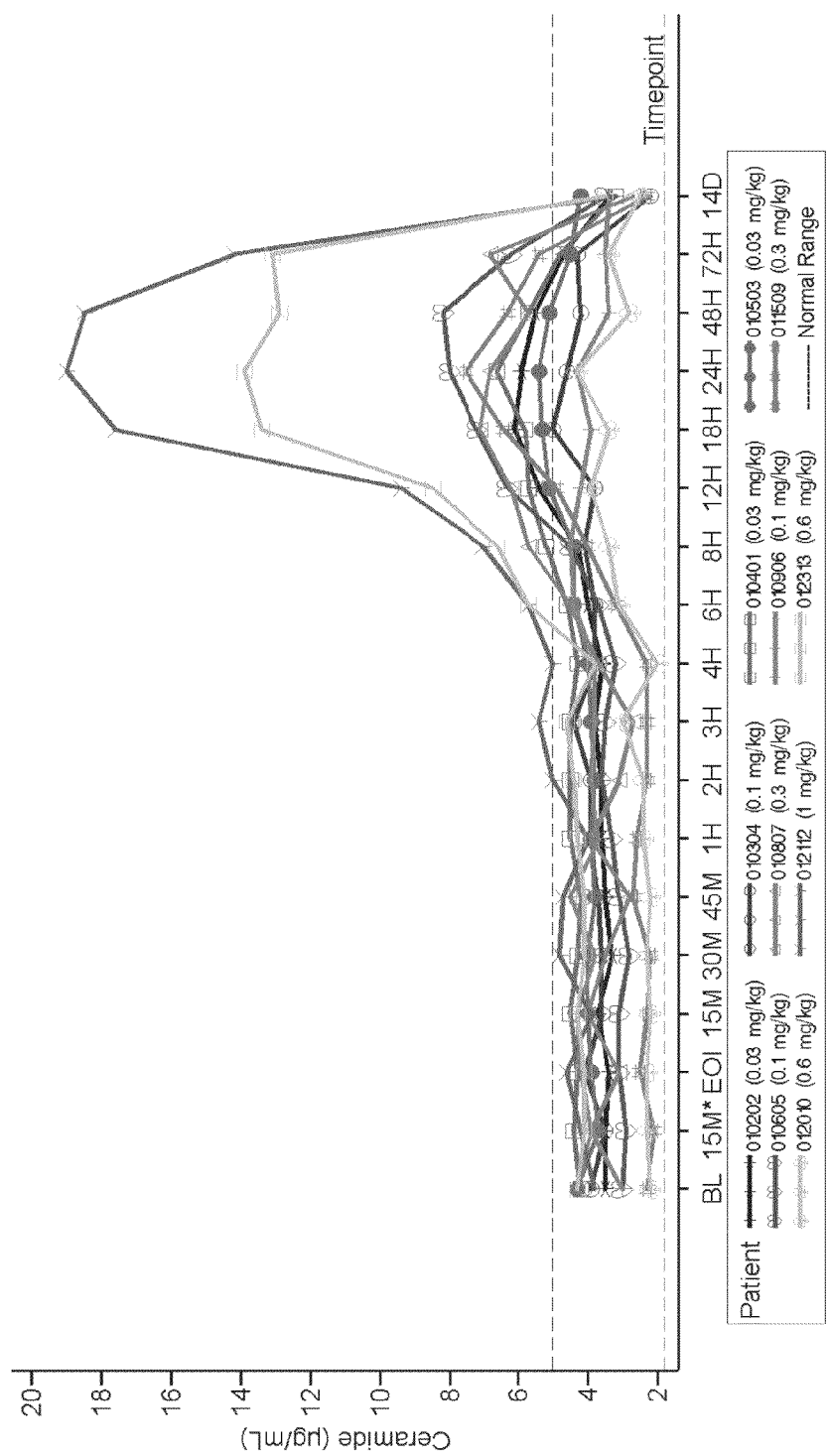
Figure 3B:
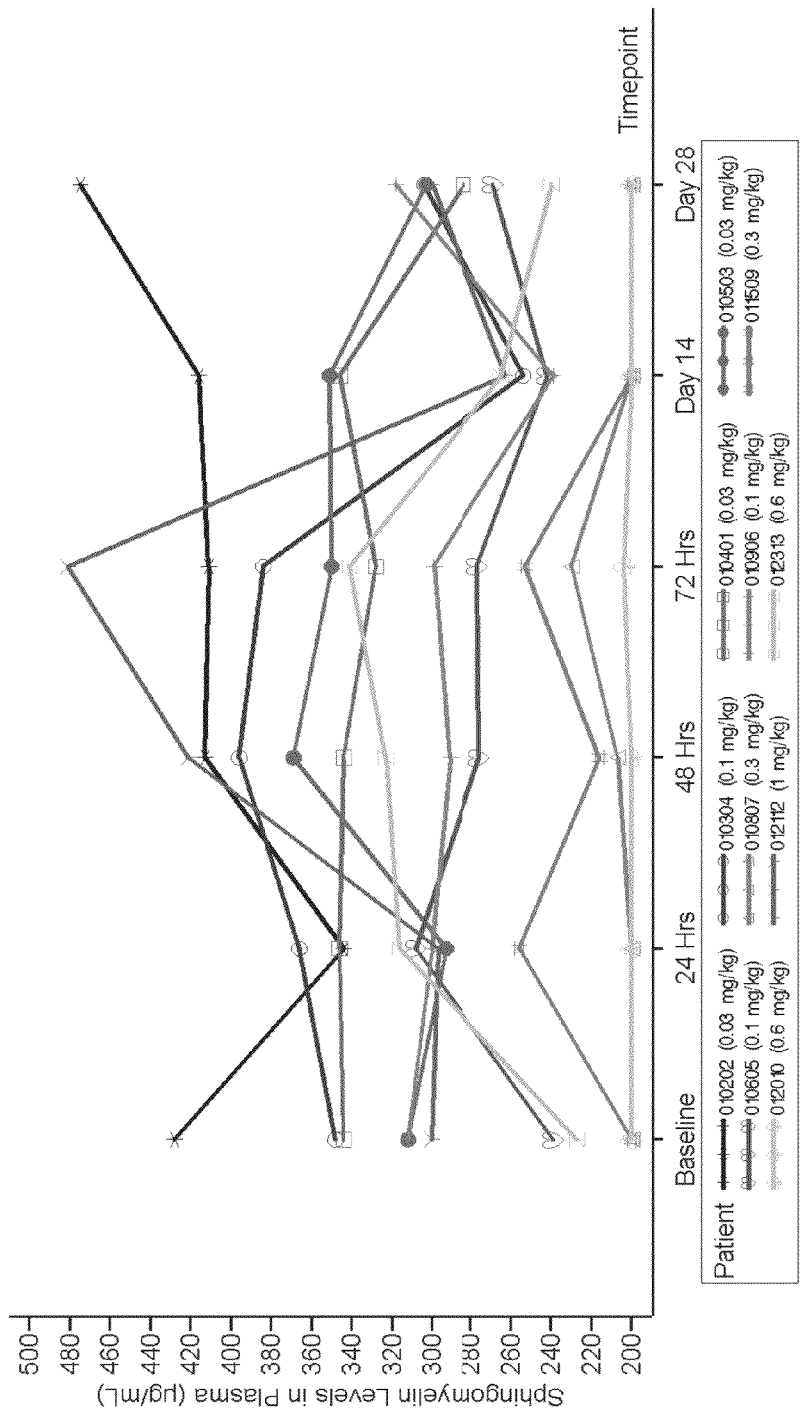
Figure 3C:
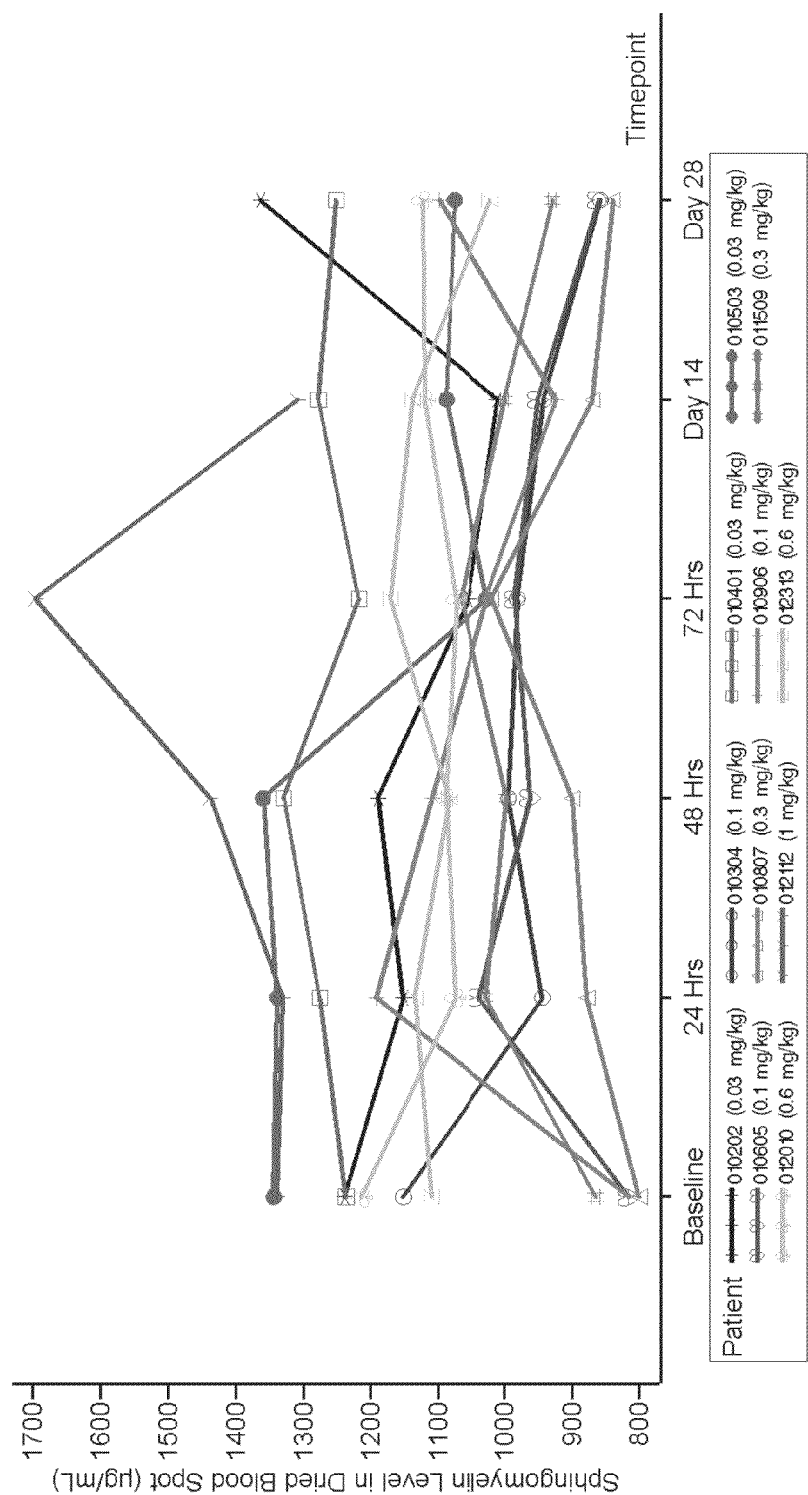

FIGS. 3A, 3B, and 3C are graphs depicting the plasma levels of ceramide (FIG. 3A) and the plasma levels of sphingomyelin (FIG. 3B), and the sphingomyelin level in dried blood spot (FIG. 3C) over time in different patients being administered different doses of rhASM. The right axis of the graphs depict the patient number and the dosage of rhASM.

Figure 4:
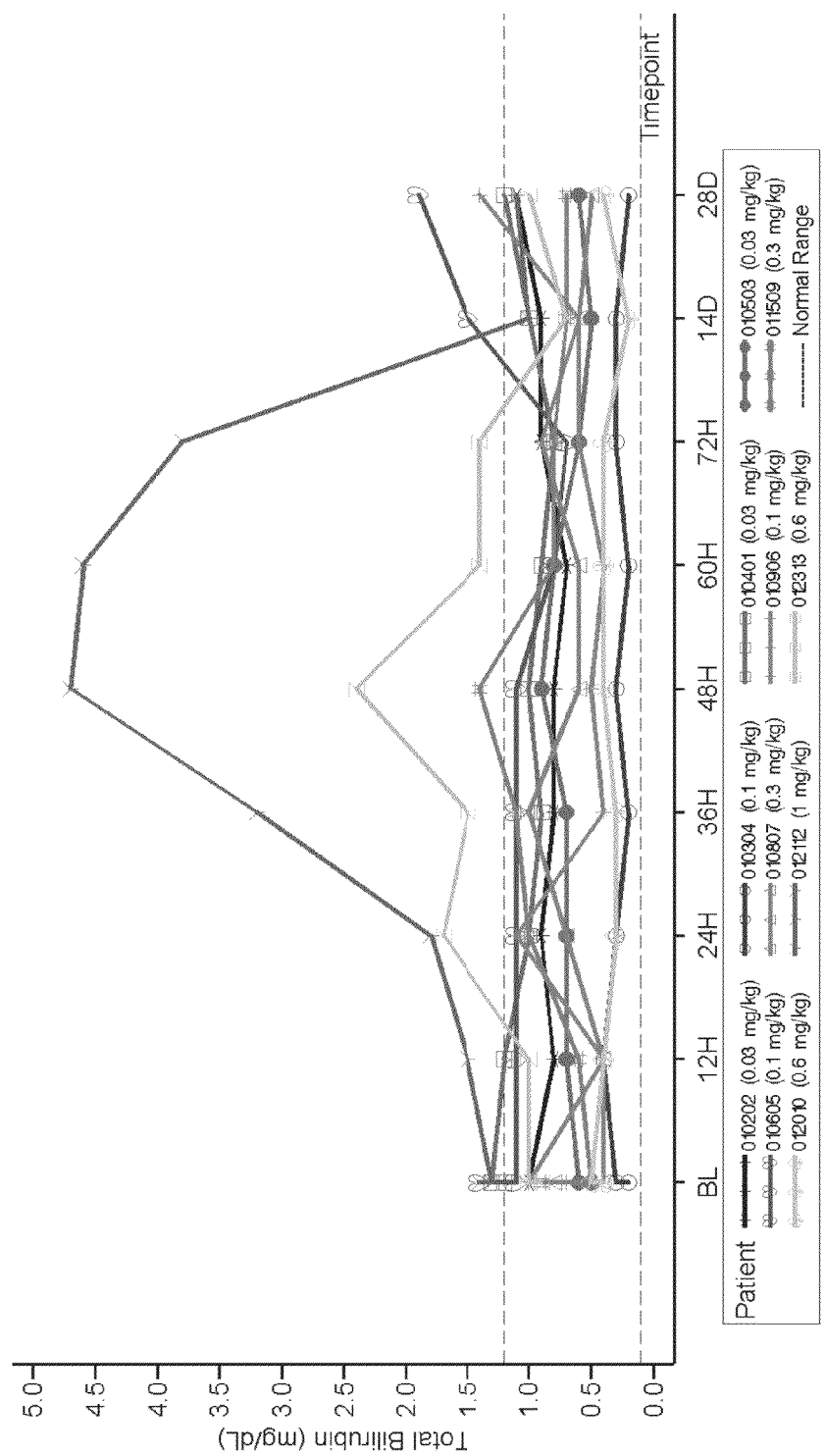
Figure 5A:
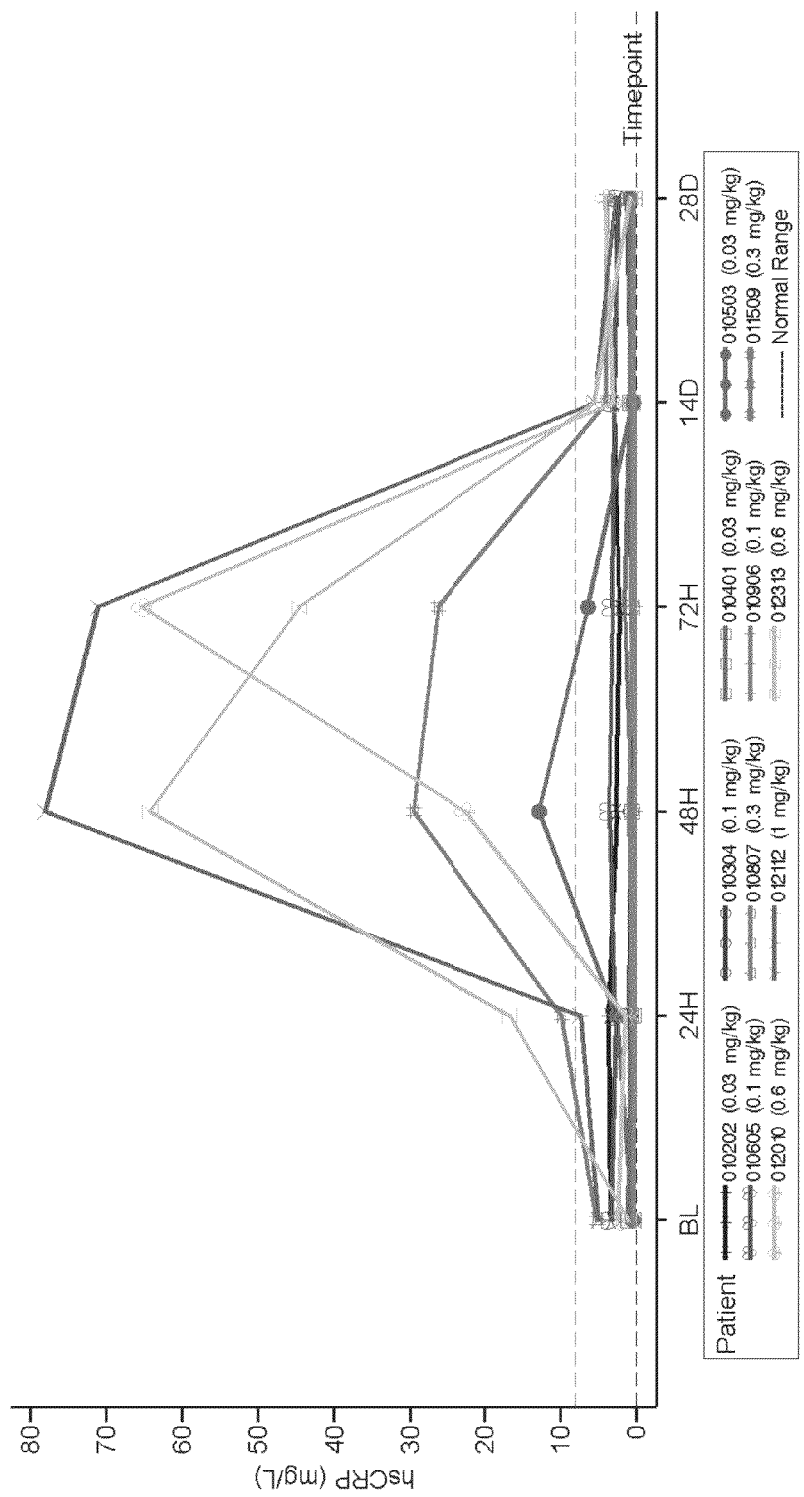
Figure 5B:
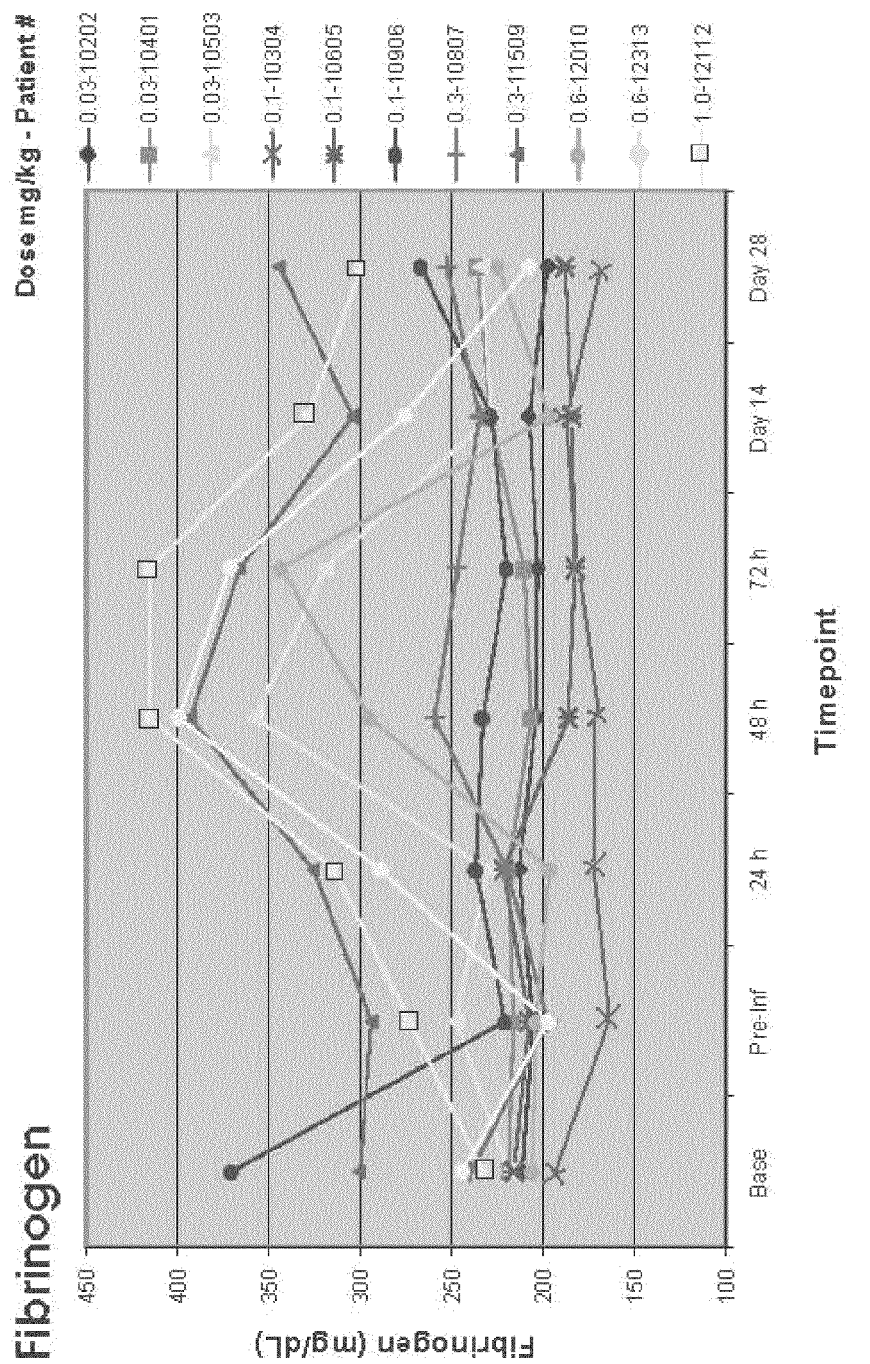
Figure 5C:
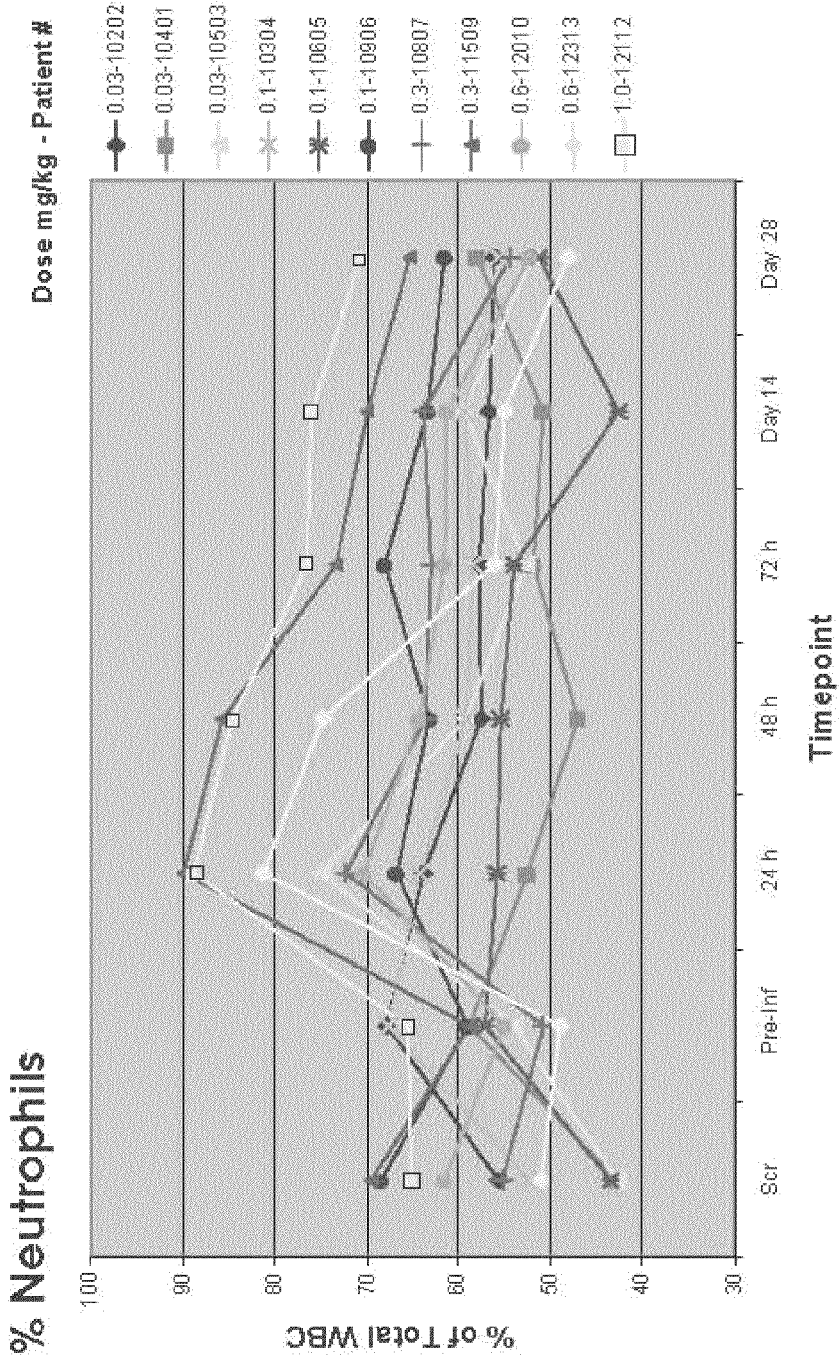
Figure 5D:
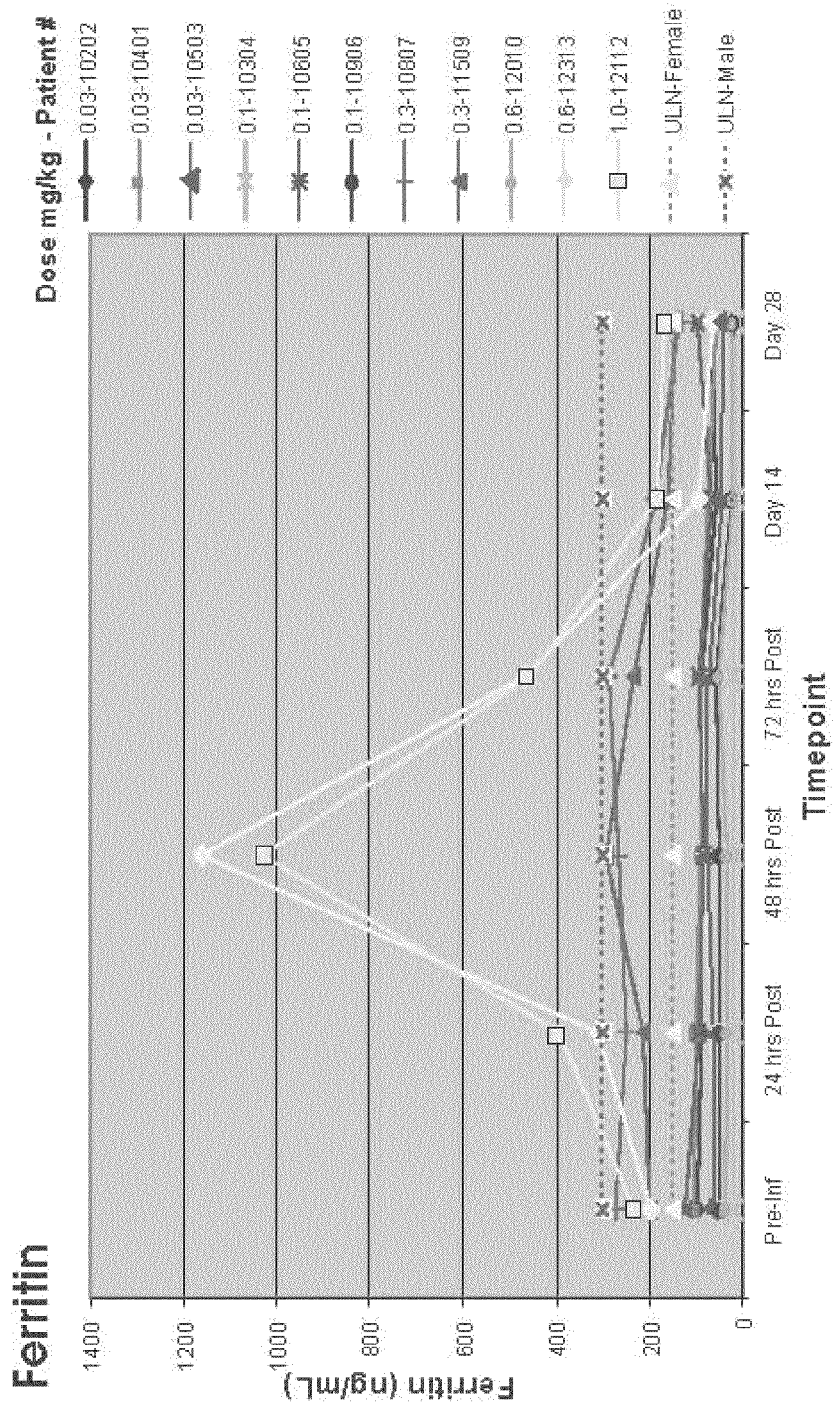
Figure 5E:
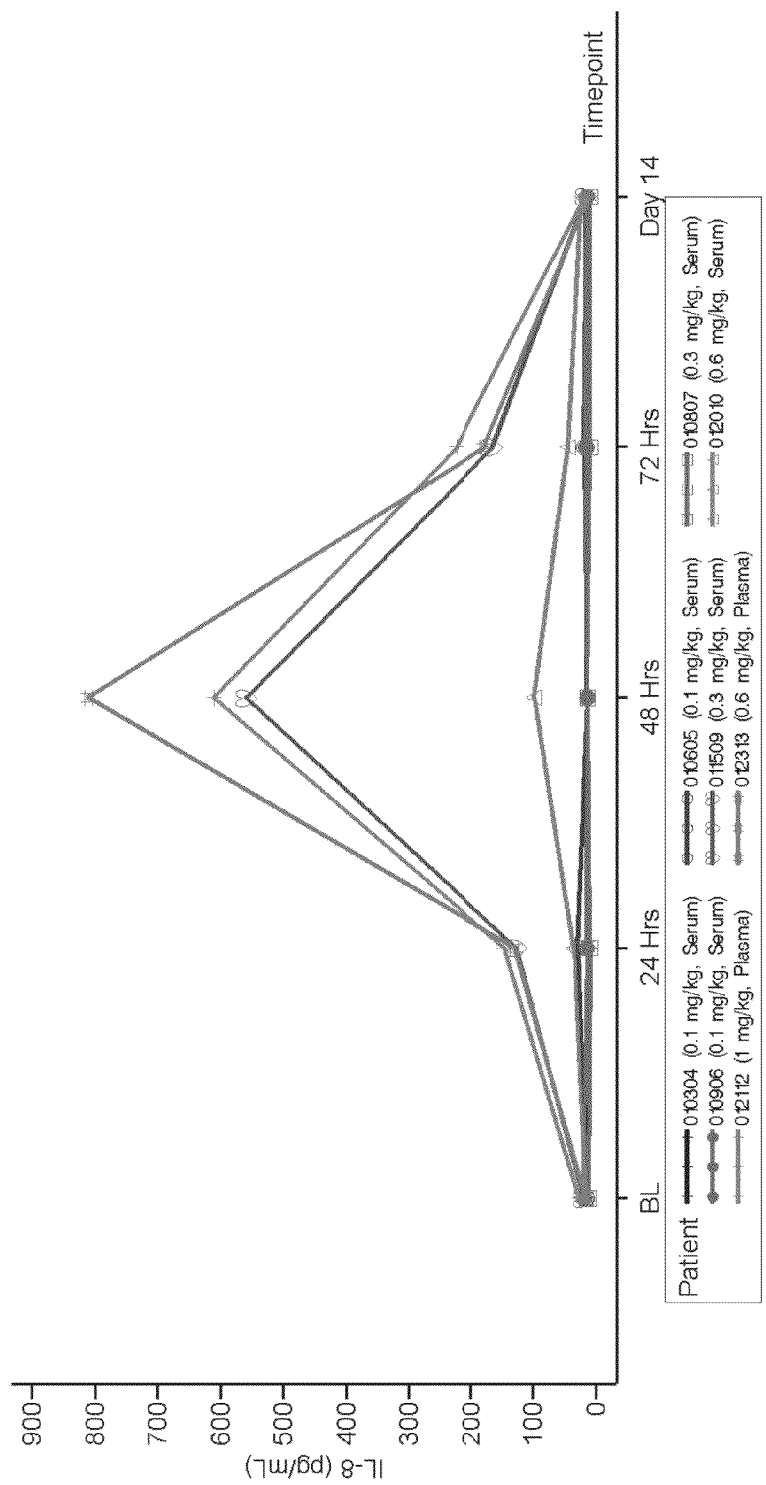
Figure 5F:
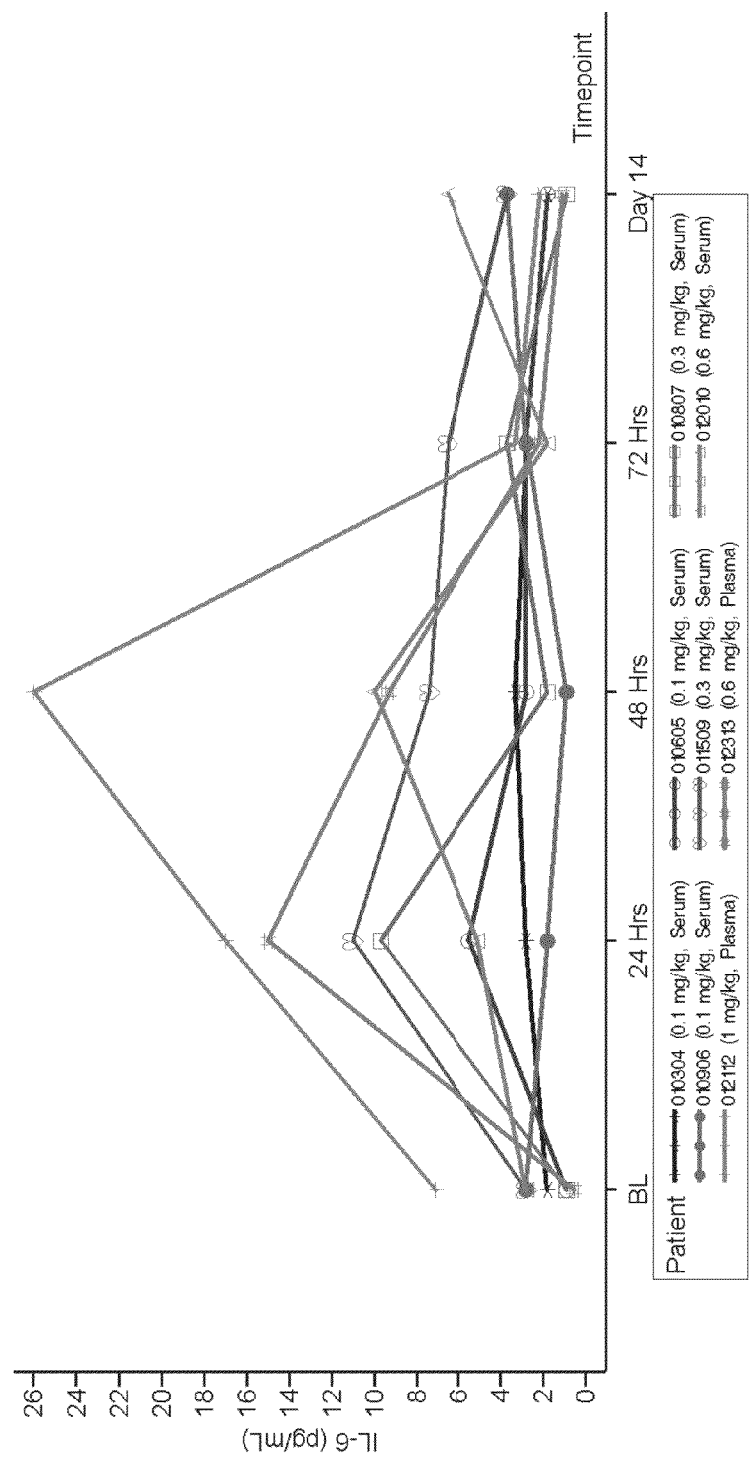
Figure 5G:
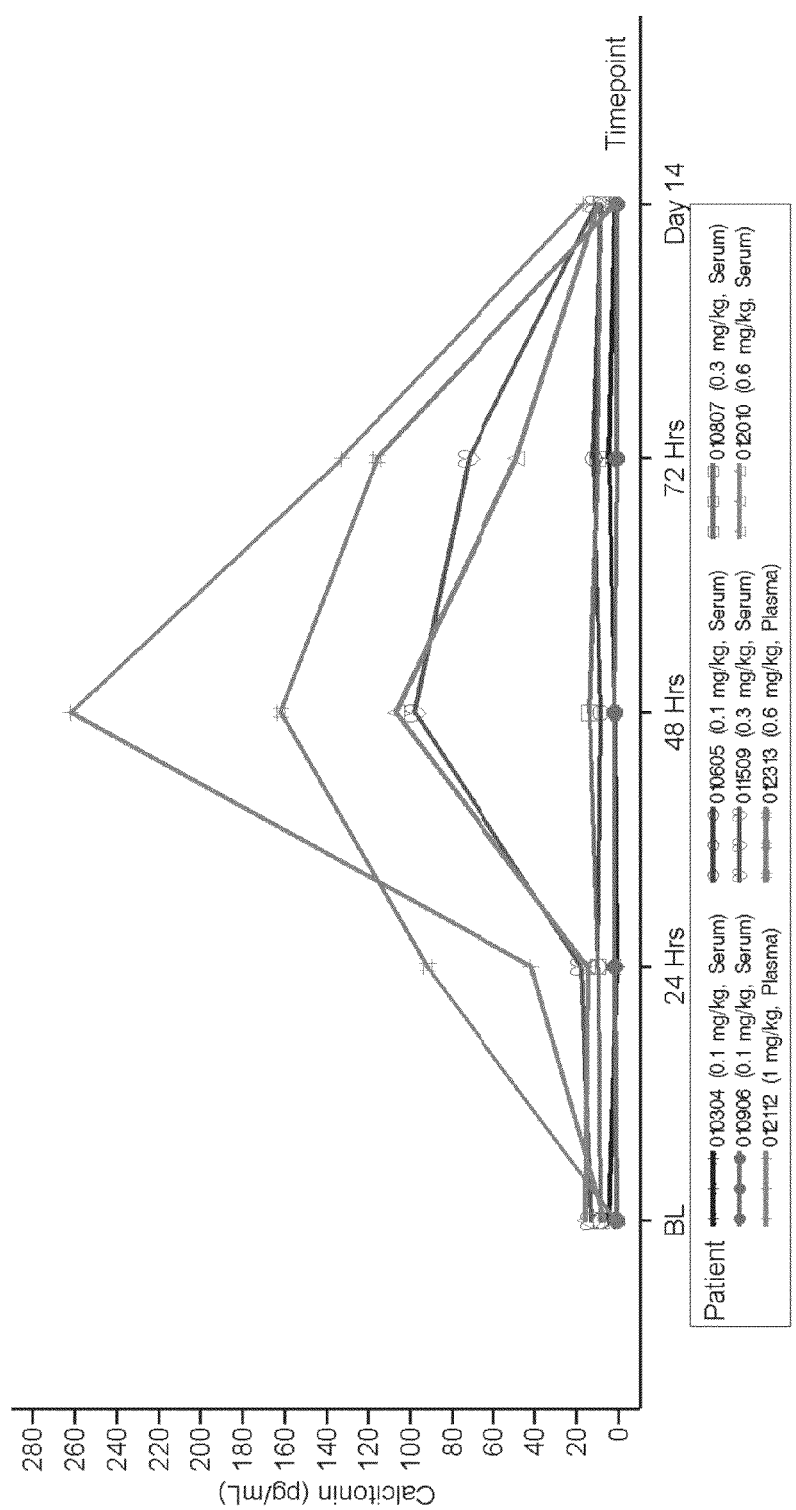

FIG. 4 is a graph depicting the total bilirubin levels determined over time in different patients being administered different doses of rhASM during the protocol. The right axis of the graph depicts the patient number and the dosage of rhASM.

FIGS. 5A-5G are graphs depicting the levels of CRP/hs-CRP (FIG. 5A), percent neutrophils (FIG. 5B), fibrinogen (FIG. 5C), ferritin (FIG. 5D), IL-8 (FIG. 5E), IL-6 (FIG. 5F), and calcitonin (FIG. 5G) determined over time in different patients being administered different doses of rhASM during the protocol. The right axis of the graphs depict the patient number and the dosage of rhASM.

FIG. 6 is a chart of treatment emergent adverse events for four patients each on a different dose of rhASM, which events were considered to be related (possibly, probably, or definitely) to treatment.

Figure 7:
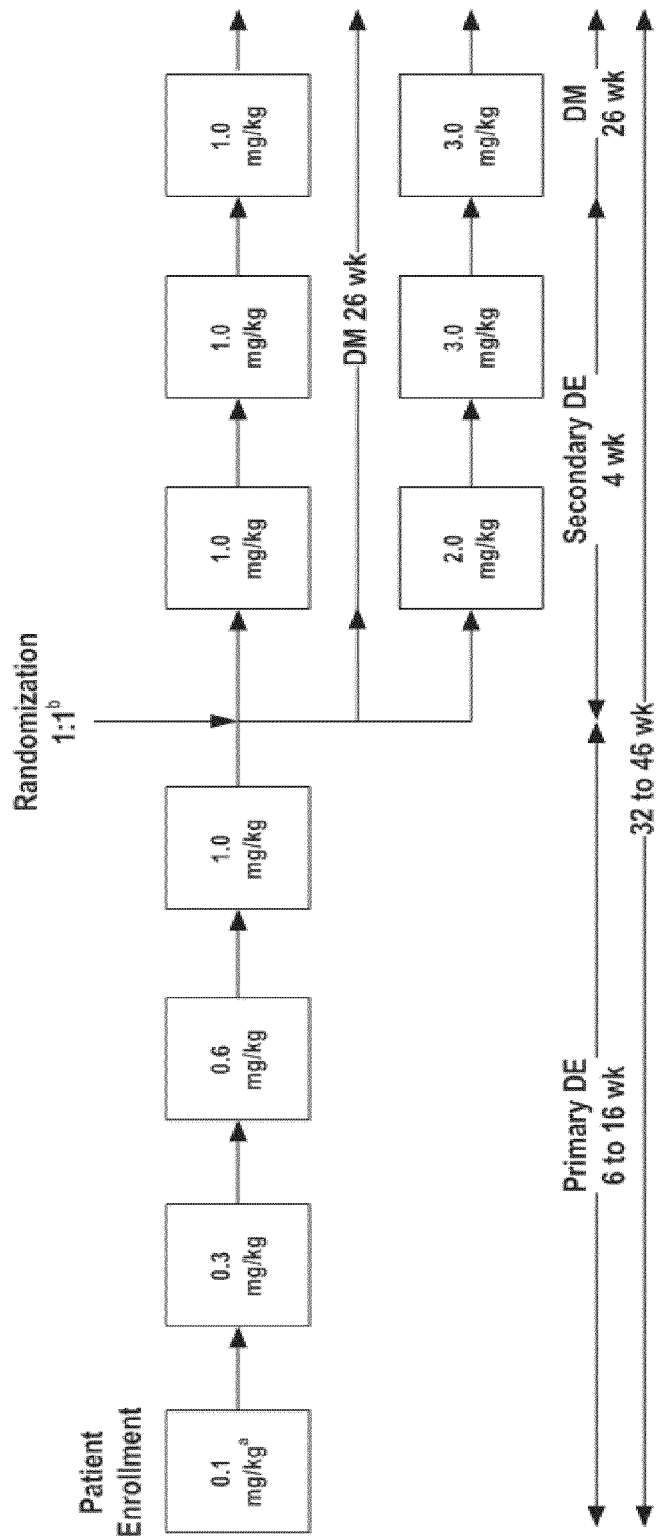

FIG. 7 is a diagram showing the primary treatment period, consisting of—dose escalation and dose maintenance phases, of the Phase 2 rhASM repeat dose protocol in patients with ASMD.

5. DETAILED DESCRIPTION OF THE INVENTION

The invention relates to dose escalation enzyme replacement therapy for the treatment of human subjects having ASMD—particularly subjects having non-neurological manifestations of NPD, and in certain embodiments, NPD type B. More particularly, the enzyme, ASM, is administered to such patients at an initial low, non-toxic dose that is then escalated in subsequent administrations. The highest dose of ASM tolerated by the patient can then be used as a maintenance dose. Alternatively, a therapeutically effective dose less than the highest dose tolerated can be used as a maintenance dose.

Treatment of NPD requires doses high enough to achieve adequate distribution of the ASM enzyme in organs of pathology (e.g., the spleen, lungs, heart, kidney and brain). Following intravenous administration of recombinant human ASM in ASMKO mice, most of the ASM activity distributes to the liver with small amounts of ASM enzymatic activity detected in other organs of pathology, such as the spleen, heart, kidney and lung (see, e.g., FIG. 9B of He et al., 1999, Biochimia et Biophsyica Acta 1432: 251-264). Thus very high doses would be required to ensure distribution and delivery of the administered enzyme to the lung, heart and kidney in patients afflicted with ASMD or Niemann-Pick disease.

Studies in an ASM knockout mouse model (ASKMO mice) showed that the majority of rhASM administered distributes to the liver and spleen where it reduces substrate, but to a much lesser extent in lungs, heart and brain (Miranda et al. FASEB 2000, 14:1988). In subsequent studies using higher doses of rhASM in the ASMKO mouse model, substrate was reduced and toxicity was not observed at doses ≤3.0 mg/kg; in fact, clinical symptoms of toxicity were not observed until doses ≥10 mg/kg were used. See, "Dose Responsive Toxicological Findings Following Intravenous Administration of Recombinant Human Acid Sphingomyelinase (rhASM) to Acid Sphingomyelinase Knock-out (ASMKO) Mice," C. Nickerson, J. Murray, A. Vitsky, M. Hawes, S. Ryan, P. Ewing, B. Thurberg, L. Andrews. Dept Pharm/Tox, Pathology, Genzyme Corp., Framingham, Mass., American Society of Human Genetics 2005; and "Elevations of Pro-Inflammatory Cytokines and Decreases in Cardiovascular Hemodynamics Following Intravenous Administration of Recombinant Human Acid Sphingomyelinase (rhASM) to Acid Sphingomyelinase Knock-out (ASMKO) Mice," J. Murray. A. M. D'Angona, C. Nickerson, A. Vitsky, M. Hawes, S. Ryan, P. Ewing, B. Thurberg, L. Andrews. Dept. Pharmacology/Toxicology & Pathology, Genzyme Corp., Framingham, Mass., Society of Toxicology 2006

Based on these ASKMO data, we treated non-neuronopathic ASMD human subjects with a conservative maximum dose of 1.0 mg/kg as described in Section 6, infra. Quite unexpectedly, toxicity in the human subjects, including the onset of adverse events with clinical symptoms, was observed using doses as low as 0.3 mg/kg! This result was especially surprising, since the ASM enzyme is absent in the knock out mouse model which should reflect a more severe condition than the human subjects who have at least some enzyme activity and relatively mild disease.

Without being bound by any theory, the administration of high doses of ASM to NPD patients can result in the hydrolysis of large amounts of sphingomyelin into large concentrations of ceramide, which may produce the toxic side effects observed in those NPD patients. The ASM enzyme hydrolyzes sphingomyelin, which is a major component of the plasma membrane of cells (see, e.g., Milaus et al., 2010 FEBS Letters 584: 1887-1894), into ceramide and phosphocholine. Ceramide is known to play a role in cell death and is known to be a pro-apoptotic agent (see, e.g., Smith and Schuchman, 2008, FASEB 22: 3419-3431).

Moreover, unlike other lysosomal enzymes associated with characterized lysosomal storage diseases. ASM hydrolyzes sphingomyelin at the neutral pH found in the plasma and the acidic pH found in the lysosome (see, e.g., Schissel et al., 1998. J. Biol. Chem. 273: 2738-2746). The ability of the ASM enzyme to function in the plasma can result in the hydrolysis of sphingomyelin found in lipoproteins and the plasma membrane of cells, which can increase the amount of the breakdown product, ceramide, which may cause the toxic side effects observed in NPD patients administered high doses of ASM enzyme.

To solve the problem of achieving adequate distribution of the ASM enzyme to the organs of pathology while avoiding or minimizing the toxicity associated with administering high doses of the enzyme, the inventors develop the regimens described herein, in which a low, non-toxic dose of the ASM enzyme is initially administered to a NPD patient and the dose is escalated over time. As the dose of the ASM enzyme is escalated, the patient can be monitored for total/direct/indirect bilirubin concentrations, the production of acute phase reactants, the production of inflammatory mediators, and related adverse events. The administration of a low dose of ASM and the escalation of the enzyme facilitates the debulking of the accumulated sphingomyelin. Once the patient is debulked, higher doses of the ASM enzyme may be safely administered to the patient to ensure adequate distribution of the ASM enzyme to target organs (e.g., liver, spleen, lungs, heart, kidney, brain, bone marrow, skeleton, joints, etc.). In certain embodiments, the maximum dose tolerated by the patient can be used as the maintenance dose. Alternatively, a therapeutically effective dose less than the highest dose tolerated can be used as a maintenance dose. In some embodiments, based upon a patient's condition, the maintenance dose may be increased or decreased.

In certain embodiments, treatment of the patient can be monitored by measuring the plasma sphingomyelin levels, plasma ceramide levels, the production of "acute phase reactants" and inflammatory mediators that are a measure of inflammatory responses, bilirubin concentrations (total, direct or indirect) and/or other biochemical markers to ensure a stable response before elevating the dose to the next level. These markers include, but are not limited to CRP/hs-CRP, cytokines (e.g., IL-8, Il-6), calcitonin, and ferritin. In specific embodiments, the patient may be monitored for one or more related adverse events which may include, but is not limited to constitutional symptoms (e.g., fever, nausea, vomiting, pain, myalgia and jaundice).

5.1. Dose Escalation Protocol

Methods are described for treating ASMD involving the administration of one or more initial, low non-toxic doses of ASM to a subject to reduce the amount of sphingomyelin that has accumulated in the subject. After a certain period of time, the dose of ASM can be escalated until the highest dosage tolerated by the subject that is therapeutically effective is achieved. Once this dosage is identified, it can be used as the maintenance dose to treat the subject. The maintenance dose can be administered weekly, biweekly, or monthly to the subject to treat ASMD. In some embodiments, a subject receiving a maintenance dose is monitored every 3 months, every 6 months or yearly for one, two, three or all of the following: (i) a related adverse events; (ii) total/direct/indirect bilirubin concentrations; (iii) plasma ceramide concentration; or (iv) an acute phase response. If the subject experiences a related adverse event of moderate intensity (e.g., a related moderate adverse event), a total bilirubin concentration greater than the total bilirubin value for a human without ASMD (e.g., a healthy human), a plasma ceramide concentration greater than the plasma ceramide concentration of a human without ASMD (e.g., a healthy human), or an acute phase response, then the dose administered to the subject can be evaluated by a physician or other medical professional to determine whether the dose should be adjusted.

In one embodiment, a method for treating a human subject having an acid sphingomyelinase deficiency, comprises: (a) a regimen for debulking accumulated sphingomyelin substrate in the human subject comprising: (i) administering an initial low non-toxic dose of ASM to the human subject; (ii) administering successively higher doses of ASM to the human subject, and monitoring the subject for one or more adverse side effects after each successive dose as indicated by elevated bilirubin or a related adverse event; and (b) a maintenance regimen comprising administering a dose equal to or less than the highest dose tolerated by the subject as the maintenance dose for the subject. In certain embodiments, the initial dose ranges is from 0.1 mg/kg to 0.5 mg/kg or 0.1 mg/kg to 1 mg/kg of ASM. In some embodiments, the successively higher doses are administered one, two, three or four weeks after the previous dose. In certain embodiments, the successively higher dose is approximately 0.1 mg/kg, 0.2 mg/kg, 0.3 mg/kg, 0.4 mg/kg, 0.5 mg/kg. 0.6 mg/kg, 0.7 mg/kg, 0.8 mg/kg, 0.9 mg/kg, 1 mg/kg, 1.2 mg/kg, 1.5 mg/kg, 1.75 mg/kg, 2 mg/kg, 3 mg/kg, 4 mg/kg or 5 mg/kg higher than the previous dose. In some embodiments, the successively higher dose is 0.1 to 0.5 mg/kg, 0.1 mg/kg to 1 mg/kg, 0.5 mg/kg to 1 mg/kg, 0.5 mg/kg to 2 mg/kg, 1 mg/kg to 2 mg/kg, 2 mg/kg to 4 mg/kg or 2 mg/kg to 5 mg/kg higher than the previous dose. In certain embodiments, the highest dose tolerated by the subject is 1 mg/kg to 2.5 mg/kg. In some embodiments, the highest dose is administered to the human subject as a maintenance dose.

In certain embodiments, a method for treating a human subject having ASMD, comprises: (a) a debulking ASM administration to reduce the amount of sphingomyelin that has accumulated in the human subject, wherein the debulking ASM administration comprises: (i) administering a low, non-toxic dose of ASM to the human subject; and (ii) administering successively higher doses of ASM to the human if the human subject does not manifest one or more adverse side effects as indicated by elevated total bilirubin concentration, elevated plasma ceramide concentration, the production of acute phase reactants, the production of inflammatory mediators, or an adverse event (e.g. such as defined by the Clinical Data Interchange Standards Consortium Study Data Tabulation Model standard terminology v.3.1.1); and (b) a maintenance ASM administration, wherein the maintenance ASM administration comprises repeated administration of a maintenance dose of ASM to the human subject. In some embodiments, the patient is monitored for a period of time after administration of a dose of ASM (e.g., 6 hours, 12 hours, 16 hours, 24 hours, 48 hours, 72 hours, weekly, or up until the next dose) for one or more adverse side effects or total bilirubin. In certain embodiments, the maintenance dose that is administered may be adjusted during the course of treatment of the patient. In some embodiments, the maintenance dose administered to the subject is the highest dose tolerated by the subject.

In a particular embodiment, a method for treating ASMD comprises administering to a subject in need thereof an initial low, non-toxic dose of ASM (e.g., a dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 0.1 mg/kg to 0.5 mg/kg, or 0.5 to 1 mg/kg of ASM) and after a certain period of time (e.g. 3 days. 1 week, 2 weeks, or 3 weeks) successively increasing the dose of ASM administered to the subject until the level of ASM activity in one or more organs of pathology is at least 5%, 6%, 7%, 8%, 9%, 10%, 12%, 15%, 20%, 25%, 30%, 35%, 40%, 50%, 75%, 80%, 85%, 90%, 95% or more of the activity of ASM in the corresponding organ in a subject(s) without ASMD (e.g. a healthy subject or population of 5, 10, 15, 20, 30, 40, 50, 75, 100, 150, 175 or more subjects) as measured by techniques known in the art, such as, e.g., the technique described in He et al., 2003, Analytical Biochemistry 314: 116-120. In another embodiment, a method for treating ASMD comprises administering to a subject in need thereof a dose of 0.1 mg/kg of ASM and after a certain period of time (e.g., 3 days, 1 week, 2 weeks, or 3 weeks) successively increasing the dose of ASM administered to the subject until the level of ASM activity in one or more of the following organs of pathology is 5% to 10%, 5% to 15%, 5% to 20%, 10% to 15%, 10% to 20%, 15% to 20%, 15% to 25%, 25% to 50%, 50% to 75%, or 75% to 95% of the normal activity of ASM in the corresponding organ in a subject(s) without ASMD (e.g., a healthy subject or population of 5, 10, 15, 20, 30, 40, 50, 75, 100, 150, 175 or more subjects) as measured by techniques known in the art, such as, e.g. the technique described in He et al., 2003, Analytical Biochemistry 314: 116-120. In certain embodiments, the dose is successively increased if the total bilirubin concentration is less than or equal to 2.0 mg/dL or 2.1 mg/dL and the subject does not experience a moderate or severe related adverse event. In specific embodiments, the activity of ASM in normal healthy subjects is estimated to be approximately 20 to 40 units/mg of protein for the brain, heart, kidney, and liver based upon the activity of ASM in similar organs in healthy mice using the assay described in Horinouchi et al., 1995, Nature Genetics 10: 288-293 (which is incorporated by reference herein in its entirety). In certain embodiments, the activity of ASM in normal healthy subjects is estimated to be approximately 15 to 25 units/mg of protein for the lung and 10 to 15 units/mg of protein for the spleen based upon the activity of ASM in similar organs in healthy mice using the assay described in Horinouchi et al., 1995, Nature Genetics 10: 288-293. In certain embodiments, once the ASM activity reaches normal or a certain percentage of normal in one or more organs of pathology, a dose equal to or less than the highest dose tolerated by the subject can be administered to the subject as the maintenance dose. Over time, the maintenance dose may be adjusted depending the health of the subject. Depending upon a subject's circumstances, the maintenance dose may be increased or decreased.

In one embodiment, a method for treating ASMD comprises: (a) administering to a human in need thereof an initial low, non-toxic dose of ASM; and (b) administering successively higher doses of ASM if the human does not manifest one, two, three or four of the following side-effects after the administration of a dose of ASM: (i) a severe related adverse event as defined by, e.g., the Clinical Data Interchange Standards Consortium Study Data Tabulation Model standard terminology v.3.1.1; (ii) a total bilirubin value of greater than 1.5 mg/dL, 1.75 mg/dL, 2.0 mg/dL, 2.1 mg/dL, 2.2 mg/dL, 2.3 mg/dL, 2.4 mg/dL, 2.5 mg/dL, 2.6 mg/dL, 2.7 mg/dL, 2.75 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL or 4 mg/dL, or in the range of 2.1 mg/dL to 2.5 mg/dL, 2.1 mg/dL to 3.0 mg/dL, or 2.1 mg/dL to 4 mg/dL that lasts for greater than 18 hours, 24 hours, 36 hours, 48 hours or 72 hours, 5 days, one week, two weeks or three weeks after administration of the dose of ASM; (iii) a plasma ceramide concentration of greater than 8.2 μg/mL, 8.3 μg/mL, 8.4 μg/mL, 8.5 μg/mL, 8.75 μg/mL, 9 μg/mL, 9.5 μg/mL, 10 μg/mL, 11 μg/mL, 12 μg/mL, 13 μg/mL, 14 μg/mL, 15 μg/mL, 16 μg/mL, 17 μg/mL, 18 μg/mL, 19 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, or 80 μg/mL, or in the range of 8.2 μg/mL to 10 μg/mL, 8.5 μg/mL to 10 μg/mL, 9 μg/mL to 12 μg/mL, 10 μg/mL to 12 μg/mL, 10 μg/mL to 15 μg/mL, 10 μg/mL to 20 μg/mL, 15 μg/mL to 20 μg/mL, or 20 μg/mL to 30 μg/mL 6 hours, 8 hours, 10 hours, 12 hours, 16 hours, 18 hours, 24 hours, 36 hours, 48 hours or 72 hours after administration of the dose of ASM; or (iv) an acute phase response. In accordance with this embodiment, the human in need thereof can be administered successively higher doses of ASM so long the human does not manifest any one or more of items (i) to (iv). In the event that the human manifests any one or more of items (i) to (iv), then depending on the severity the manifestation, the same dose that resulted in the manifestation of items (i) to (iv) may be repeated or the dose may be decreased to the previous dose.

In another embodiment, a method for treating ASMD comprises: (a) administering to a human in need thereof an initial dose of 0.1 mg/kg of ASM; (b) monitoring one or more of the following in the human subsequent the administration of the dose of ASM: (i) total bilirubin concentration, (ii) the manifestation of a related adverse event; (iii) an acute phase response; or (iv) plasma ceramide concentration; (c) determining whether to adjust (e.g., increase or decrease) or maintain the dose of ASM based on one or more of items (i) to (iv); and (d) repeating steps (b) and (c) following the administration of the dose of ASM determined in the previous step (c). In another embodiment, a method for treating ASMD comprises: (a) administering to a human in need thereof two initial doses of 0.1 mg/kg of ASM 2 to 4 weeks apart; (b) monitoring one or more of the following in the human subsequent to the administration of each dose of ASM: (i) total bilirubin concentration, (ii) the manifestation of a related adverse event; (iii) an acute phase response; or (iv) plasma ceramide concentration; (c) determining whether to adjust (e.g., increase or decrease) or maintain the dose of ASM based on one or more of items (i) to (iv); and (d) repeating steps (b) and (c) following the administration of the dose of ASM determined in the previous step (c). In accordance with these embodiments, the human can be administered a higher dose of ASM one or more times 2 to 4 weeks apart if the initial dose of 0.1 mg/kg or the adjusted dose determined in step (c) results in: (i) a total bilirubin concentration of less than or equal to 2.0 mg/dL before the deadline for administering another dose of ASM; (ii) no related adverse events or only mild related adverse events; (iii) a plasma ceramide within the normal range 6 hours, 8 hours, 12 hours, 16 hours, 18 hours, 24 hours, 48 hours, or 72 hours administration the last dose of ASM; or (iv) no acute phase response or an acute phase response that is not statistically significant. However, the dose can be maintained or decreased if the initial dose of 0.1 mg/kg or the adjusted dose determined in step (c) results in: (i) a total bilirubin concentration of 2.1 mg/dL or greater before the deadline for administering another dose of ASM; (ii) a related adverse event; (iii) a plasma ceramide above the normal range 6 hours, 8 hours, 12 hours, 16 hours, 18 hours, 24 hours, 48 hours, or 72 hours administration the last dose of ASM; or (iv) an acute phase response that is statistically significant.

In another embodiment, a method for treating ASMD comprises: (A) administering to a human in need thereof two initial doses of 0.1 mg/kg 2 weeks apart; (B) monitoring either (i) total bilirubin concentration, (ii) the manifestation of a related adverse event, (iii) both (i) and (ii) in the human subsequent to the administration of each initial dose of ASM: (C) determining whether to adjust (e.g., increase or decrease) or maintain the dose of ASM based on one or more of items (i) to (iii), and (D) repeating steps (B) and (C) following the administration of the dose of ASM determined in the previous step (C), wherein (a) the dose administered to the human is increased if the total bilirubin concentration is less than or equal to 2.0 mg/dL or the human presents with a mild related adverse event; (b) the human continues to receive the current dose 1 to 4 times 2 to 4 weeks apart if the total bilirubin concentration is 2.1 mg/dL to 3.1 mg/dL or the human presents with a moderate related adverse event and this dose is maintained if the total bilirubin concentration remains greater than 2.0 mg/dL subsequent to the last administered dose; (c) the dose administered to the human is decreased or no longer administered ASM if the total bilirubin concentration is greater than 3 mg/dL or the human presents with severe related adverse events.

In another embodiment, a method for treating ASMD comprises: (A) administering to a human in need thereof two initial doses of 0.3 mg/kg 2 weeks apart; (B) monitoring either (i) total bilirubin concentration, (ii) the manifestation of a related adverse event, (iii) both (i) and (ii) in the human subsequent to the administration of each dose of ASM; (C) determining whether to adjust (e.g., increase or decrease) or maintain the dose of ASM based on one or more of items (i) to (iii), and (D) repeating steps (B) and (C) following the administration of the dose of ASM determined in the previous step (C), wherein (a) the dose administered to the human is increased if the total bilirubin concentration is less than or equal to 2.0 mg/dL or the human presents with a mild related adverse event; (b) the human continues to receive the current dose 1 to 4 times 2 to 4 weeks apart if the total bilirubin concentration is 2.1 mg/dL to 3.1 mg/dL or the human presents with a moderate related adverse event and this dose is maintained if the total bilirubin concentration remains greater than 2.0 mg/dL subsequent to the last administered dose; (c) the dose administered to the human is decreased or no longer administered ASM if the total bilirubin concentration is greater than 3 mg/dL or the human presents with severe related adverse events.

In a specific embodiment, a method for treating ASMD comprises administering to a subject in need thereof a dose of 0.1 mg/kg of ASM and after two weeks a dose of 0.3 mg/kg of ASM every two weeks. In another specific embodiment, a method for treating ASMD comprises administering to a subject in need thereof a dose of 0.1 mg/kg of ASM, a dose of 0.3 mg/kg of ASM two weeks after the administration of the 0.1 mg/kg dose of ASM, and a dose of 0.6 mg/kg of ASM two weeks after the administration of the dose of 0.3 mg/kg of ASM. In another specific embodiment, a method for treating ASMD comprises administering to a subject in need thereof a dose of 0.1 mg/kg of ASM, a dose of 0.3 mg/kg of ASM two weeks after the administration of the 0.1 mg/kg dose of ASM, a dose of 0.6 mg/kg of ASM two weeks after the administration of the dose of 0.3 mg/kg of ASM, and a dose of 1 mg/kg of ASM two weeks after the administration of the dose of 0.6 mg/kg of ASM. In certain embodiments, each dose may be repeated at least two, and preferably two to four times before escalating the dose to the next level. In accordance with these embodiments, the dose is only escalated if the total bilirubin value is equal to or less than 2.0 mg/dL and/or the subject experiences a mild related adverse event. The dose is not escalated if the total bilirubin value is between 2.1 and 3 mg/dL and/or the subject experiences a moderate related adverse event. The dose is reduced to a previously tolerated dose if the total bilirubin value is greater than 3.0 mg/dL of total bilirubin and/or the subject experiences a serious related adverse event.

In specific embodiments, a patient is treated for ASMD in accordance with the protocol described in Section 8 or 9 et seq., infra, or an analogous protocol.

In a specific embodiment, a method for treating ASMD comprises administering to a subject in need thereof a dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, or 0.1 mg/kg to 0.5 mg/kg, or 0.1 mg/kg to 1 mg/kg of ASM and after a certain period of time (e.g. 3 days, 1 week, 2 weeks, 3 weeks or 4 weeks) successively increasing the dose of ASM administered to the subject if total bilirubin concentration is less than or equal to 2.1 mg/dL and the subject does not experience a moderate or severe related adverse event. In some embodiments, the dose of ASM is successively increased until the maximum or highest dose tolerated by the subject which is therapeutically effective is achieved. In certain embodiments, such highest or maximum dose tolerated is administered until such time as the accumulated sphingomyelin in the organs of pathology is debulked after which a maintenance dose that is lower than the maximum dose tolerated which is still therapeutically effective is administered to the subject. In some embodiments, the maintenance dose is scaled back over time as the patient's condition improves.

In a specific embodiment, the highest dose tolerated that is therapeutically effective is the highest dosage that is effective in the treatment of ASMD without causing one, two or more severe related adverse events or related adverse events as defined by, e.g., the Clinical Data Interchange Standards Consortium Study Data Tabulation Model standard terminology v.3.1.1. In another embodiment, the highest dose tolerated that is therapeutically effective is the highest dosage that is effective in the treatment of ASMD without causing an increase in the total bilirubin concentration relative to a patient's total bilirubin concentration prior to administration of ASM, which increase lasts for greater than two days, three days, five days, one week, two weeks, or three weeks. In another embodiment, the highest dose tolerated that is therapeutically effective is the highest dosage that is effective in the treatment of ASMD without causing a total bilirubin concentration of greater than normal total bilirubin concentrations that lasts for greater than 18 hours, 24 hours, 36 hours, 48 hours or 72 hours, 5 days, one week, two weeks or three weeks after administration of the dose of ASM. The normal total bilirubin concentration in a human without ASMD (e.g., a healthy human) is less than approximately 1.2 mg/dL. In certain embodiments, the highest dose tolerated that is therapeutically effective is the highest dosage that is effective in the treatment of ASMD without causing a total bilirubin concentration that is greater than approximately 1.5 mg/dL, 1.75 mg/dL, 2.0 mg/dL, 2.1 mg/dL, 2.2 mg/dL, 2.3 mg/dL, 2.4 mg/dL, 2.5 mg/dL, 2.6 mg/dL, 2.7 mg/dL, 2.75 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL or 4 mg/dL or in the range of 2.1 mg/dL to 2.5 mg/dL, 2.1 mg/dL to 3.0 mg/dL, or 2.1 mg/dL to 4 mg/dL that lasts for greater than 18 hours, 24 hours, 36 hours, 48 hours or 72 hours, 5 days, one week, two weeks or three weeks after administration of the dose of ASM.

In another embodiment, the highest dose tolerated is the highest dosage that is effective in the treatment of ASMD without resulting in a plasma ceramide concentration that is greater than the normal plasma ceramide concentration 6 hours, 8 hours, 12 hours, 16 hours, 18 hours, 24 hours, 36 hours, 48 hours or 72 hours after administration of the dose of ASM. The normal plasma ceramide concentration in a human without ASMD (e.g., a healthy human) is approximately 1.5 to 8 μg/mL. In certain embodiments, the highest dose tolerated is the highest dosage that is effective in the treatment of ASMD without resulting in a plasma ceramide concentration of greater than approximately 8.2 μg/mL, 8.3 μg/mL, 8.4 μg/mL, 8.5 μg/mL, 8.75 μg/mL, 9 μg/mL, 9.5 μg/mL, 10 μg/mL, 11 μg/mL, 12 μg/mL, 13 μg/mL, 14 μg/mL, 15 μg/mL, 16 μg/mL, 17 μg/mL, 18 μg/mL, 19 μg/mL, 20 μg/mL, 25 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, or 80 μg/mL, or in the range of 8.2 μg/mL to 10 μg/mL, 8.5 μg/mL to 10 μg/mL, 9 μg/mL to 12 μg/mL, 10 μg/mL to 12 μg/mL, 10 μg/mL to 15 μg/mL, 10 μg/mL to 20 μg/mL, 15 μg/mL to 20 μg/mL, or 20 μg/mL to 30 μg/mL 6 hours, 8 hours, 10 hours, 12 hours, 16 hours, 18 hours, 24 hours, 36 hours, 48 hours or 72 hours after administration of the dose of ASM.

In another embodiment, the highest dose tolerated that is therapeutically effective is the highest dosage that is effective in the treatment of ASMD without causing an acute phase response. An acute phase response can be assessed by a change in the concentration of an acute phase reactant, a change in prothrombin time, a change in partial thromboplastin time, or a change in the percentage of neutrophils. For example, an acute phase response can be assessed by an increase in one or more of the following factors following ASM administration to subject relative to those factors prior to administration of ASM to the subject or relative to those factors in a human without ASMD (e.g., a healthy human): the percentage of neutrophils, the prothrombin time (PT), the partial thromboplastin time (PTT), the total bilirubin concentration, C-reactive protein (CRP/hs-CRP) concentration, serum amyloid A (SAA), serum amyloid P component, angiotensin converting enzyme (ACE), ferritin concentration, IL-6 concentration, IL-8 concentration, calcitonin concentration, albumin concentration, or fibrinogen concentration. An acute phase response can also be assessed by a decrease in iron concentration or albumin concentration following ASM administration to a subject relative to the iron concentration or albumin concentration in the subject prior to ASM administration or relative to the iron concentration or albumin concentration in a human without ASMD (e.g., a healthy human).

In a specific embodiment, the highest dose tolerated that is therapeutically effective is the highest dosage that is effective in the treatment of ASMD without causing an increase in CRP/hs-CRP concentration 6 hours, 8 hours, 12 hours, 16 hours, 18 hours, 24 hours, 36 hours, 48 hours or 72 hours after administration of the dose of ASM relative to a patient's CRP/hs-CRP concentration prior to administration of ASM. In another specific embodiment, the highest dose tolerated that is therapeutically effective is the highest dosage that is effective in the treatment of ASMD without resulting in a plasma CRP/hs-CRP concentration that is greater than the normal plasma CRP/hs-CRP concentration 6 hours, 8 hours, 12 hours, 16 hours, 18 hours, 24 hours, 36 hours, 48 hours or 72 hours after administration of the dose of ASM. The normal plasma CRP/hs-CRP concentration in a human without ASMD (e.g., a healthy human) is less than approximately 8 mg/dL. In certain embodiments, the highest dose tolerated that is therapeutically effective is the highest dosage that is effective in the treatment of ASMD without causing a plasma CRP/hs-CRP concentration of greater than approximately 8.1 mg/L, 8.2 mg/L, 8.3 mg/L, 8.4 mg/L, 8.5 mg/L, 8.6 mg/L, 8.7 mg/L, 8.8 mg/L, 8.8 mg/L, 8.9 mg/L. 9 mg/L, 9.5 mg/L, 10 mg/L, 11 mg/L, or 12 mg/L, or in the range of 8.5 mg/L to 10 mg/L, or 8.5 mg/L to 12 mg/L, or 10 mg/L to 12 mg/L 6 hours, 8 hours, 12 hours, 16 hours, 18 hours, 24 hours, 36 hours, 48 hours or 72 hours after administration of the dose of ASM.

In a specific embodiment, the highest dose tolerated that is therapeutically effective is the highest dosage that is effective in the treatment of ASMD without causing an increase in ferritin concentration 6 hours, 8 hours, 12 hours, 16 hours, 18 hours, 24 hours, 36 hours, 48 hours or 72 hours after administration of the dose of ASM relative to a patient's ferritin concentration prior to administration of ASM. In another specific embodiment, the highest dose tolerated that is therapeutically effective is the highest dosage that is effective in the treatment of ASMD without resulting in a plasma ferritin concentration that is greater than the normal plasma ferritin concentration 6 hours, 8 hours, 12 hours, 16 hours, 18 hours, 24 hours, 36 hours, 48 hours or 72 hours after administration of the dose of ASM. The normal plasma ferritin concentration in a human without ASMD (e.g., a healthy human) is 10 to 30 ng/mL. In certain embodiments, the highest dose tolerated that is therapeutically effective is the highest dosage that is effective in the treatment of ASMD without causing a plasma ferritin concentration of greater than approximately 300 ng/mL, 325 ng/mL, 350 ng/mL, 375 ng/mL, 400 ng/mL, 425 ng/mL, 450 ng/mL, 475 ng/mL, 500 ng/mL, 525 ng/mL, 550 ng/mL, 575 ng/mL, 600 ng/mL, 625 ng/mL, 650 ng/mL, 675 ng/mL, 700 ng/mL, 725 ng/mL, 750 ng/mL, 775 ng/mL, 800 ng/mL, 850 ng/mL, 900 ng/mL, 950 ng/mL, 1000 ng/mL, 1050 ng/mL, 1100 ng/mL, 1150 ng/mL, or 1200 ng/mL or in the range of 600 ng/mL to 800 ng/mL, 650 ng/mL to 850 ng/mL, 600 ng/mL to 1000 ng/mL, 600 ng/mL to 1200 ng/mL, 800 ng/mL to 1000 ng/mL, 900 ng/mL to 1000 ng/mL, or 1000 ng/mL, or 1000 ng/mL to 1200 ng/mL 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in plasma or serum IL-8 concentration 6 hours, 8 hours, 12 hours, 16 hours, 18 hours, 24 hours, 36 hours, 48 hours or 72 hours after administration of a dose of ASM relative to a patient's IL-8 concentration prior to administration of ASM can be used as a measurement of an acute phase response. In another specific embodiment, a plasma or serum IL-8 concentration that is greater than the normal plasma IL-8 concentration 6 hours, 8 hours, 12 hours, 18 hours, 24 hours, 36 hours, 48 hours or 72 hours after administration of the dose of ASM can be used as a measurement of an acute phase response. In certain embodiments, a plasma IL-8 concentration of greater than approximately 24 pg/mL, 50 pg/mL, 75 pg/mL, 100 pg/mL, 200 pg/mL, 300 pg/mL, 400 pg/mL, 500 pg/mL, 600 pg/mL, 700 pg/mL, 800 pg/mL, or 900 pg/mL 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in plasma or serum IL-6 concentration 6 hours, 8 hours, 12 hours, 16 hours, 18 hours, 24 hours, 36 hours, 48 hours or 72 hours after administration of a dose of ASM relative to a patient's IL-6 concentration prior to administration of ASM can be used as a measurement of an acute phase response. In another specific embodiment, a plasma or serum IL-6 concentration that is greater than the normal plasma or serum IL-6 concentration 6 hours, 8 hours, 12 hours, 18 hours, 24 hours, 36 hours, 48 hours or 72 hours after administration of the dose of ASM can be used as a measurement of an acute phase response. In certain embodiments, a plasma IL-6 concentration of greater than approximately 4.4 pg/mL, 6 pg/mL, 8 pg/mL, 10 pg/mL, 15 pg/mL, 20 pg/mL, 25 pg/mL, or 30 pg/mL 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, an increase in plasma or serum calcitonin concentration 6 hours, 8 hours, 12 hours, 16 hours, 18 hours, 24 hours, 36 hours, 48 hours or 72 hours after administration of a dose of ASM relative to a patient's calcitonin concentration prior to administration of ASM can be used as a measurement of an acute phase response. In another specific embodiment, a plasma or serum calcitonin concentration that is greater than the normal plasma calcitonin concentration 6 hours, 8 hours, 12 hours, 18 hours, 24 hours, 36 hours, 48 hours or 72 hours after administration of the dose of ASM can be used as a measurement of an acute phase response. In certain embodiments, a plasma calcitonin concentration of greater than approximately 9.4 pg/mL, 20 pg/mL, 30 pg/mL, 40 pg/mL, 50 pg/mL, 75 pg/mL, 100 pg/mL, 150 pg/mL, 200 pg/mL, or 250 pg/mL, 6 hours, 8 hours, 12 hours, 16 hours, 18 hours, 24 hours, 36 hours, 48 hours or 72 hours after administration of the dose of ASM can be used as a measurement of an acute phase response.

In a specific embodiment, the highest dose tolerated that is therapeutically effective is the highest dosage that is effective in the treatment of ASMD without causing an increase in fibrinogen concentration 6 hours, 8 hours, 12 hours, 18 hours, 24 hours, 36 hours, 48 hours or 72 hours after administration of the dose of ASM relative to a patient's fibrinogen concentration prior to administration of ASM. In another specific embodiment, the highest dose tolerated that is therapeutically effective is the highest dosage that is effective in the treatment of ASMD without resulting in a plasma fibrinogen concentration that is greater than the normal plasma fibrinogen concentration 6 hours, 8 hours, 12 hours, 16 hours, 18 hours, 24 hours, 36 hours, 48 hours or 72 hours after administration of the dose of ASM. The normal plasma fibrinogen concentration in a human without ASMD (e.g., a healthy human) is 150 mg/dL to 300 mg/dL. In certain embodiments, the highest dose tolerated that is therapeutically effective is the highest dosage that is effective in the treatment of ASMD without causing a plasma fibrinogen concentration of greater than approximately 350 mg/dL, 375 mg/dL, 400 mg/dL, 425 mg/dL, or 450 mg/dL, or in the range of 350 mg/dL to 400 mg/dL, 350 mg/dL to 450 mg/dL or 400 mg/dL to 450 mg/dL, 6 hours, 8 hours, 12 hours, 16 hours, 18 hours, 24 hours, 36 hours, 48 hours or 72 hours after administration of the dose of ASM.

In a specific embodiment, the highest dose tolerated that is therapeutically effective is the highest dosage that is effective in the treatment of ASMD without causing an increase in the percentage of neutrophils of total white blood cells 6 hours, 8 hours, 12 hours, 16 hours, 18 hours, 24 hours, 36 hours, 48 hours or 72 hours after administration of the dose of ASM relative to a patient's percentage of neutrophils of total white blood cells prior to administration of ASM. In another specific embodiment, the highest dose tolerated that is therapeutically effective is the highest dosage that is effective in the treatment of ASMD without resulting in a percentage of neutrophils of total white blood cells that is greater than the normal percentage of neutrophils of total white blood cells concentration 6 hours, 8 hours, 12 hours, 16 hours, 18 hours, 24 hours, 36 hours, 48 hours or 72 hours after administration of the dose of ASM. The normal percentage of neutrophils of total white blood cells in a human without ASMD (e.g., a healthy human) is 45% to 60%. In certain embodiments, the highest dose tolerated that is therapeutically effective is the highest dosage that is effective in the treatment of ASMD without causing an increase in the percentage of neutrophils of total white blood cells that is 70%, 75%, 80%, 85%, 90%, 95% or greater 6 hours, 8 hours, 12 hours, 18 hours, 24 hours, 36 hours, 48 hours or 72 hours after administration of the dose of ASM.

In another embodiment, the highest dose tolerated that is therapeutically effective is the highest dosage that is effective in the treatment of ASMD without causing an increase in antibodies to the administered ASM. In another embodiment, the highest dose tolerated that is therapeutically effective is the highest dosage that is effective in the treatment of ASMD without causing a hypersensitivity reaction. In another embodiment, the highest dose tolerated that is therapeutically effective is the highest dosage that is effective in the treatment of ASMD without causing cytokine release syndrome.

In certain embodiments, the highest dose tolerated by a subject that is therapeutically effective is 1 mg/kg to 2.5 mg/kg, 2 mg/kg to 3 mg/kg, 3 mg/kg to 5 mg/kg, 5 mg/kg to 10 mg/kg, 10 mg/kg to 15 mg/kg, 15 mg/kg to 20 mg/kg, 15 mg/kg to 25 mg/kg, 20 mg/kg to 30 mg/kg, or 25 mg/kg to 50 mg/kg. In some embodiments, the highest dose tolerated by a subject that is therapeutically effective is 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, or 15 mg/kg. In certain embodiments, the highest dose tolerated by a subject that is therapeutically effective is 20 mg/kg, 25 mg/kg, 30 mg/kg, 35 mg/kg, 40 mg/kg. 45 mg/kg, or 50 mg/kg.

In a specific embodiment, the highest dose tolerated that is therapeutically effective is the highest dosage that is effective in the treatment of ASMD without causing one, two or more severe related adverse events or related adverse events as defined by, e.g., the Clinical Data Interchange Standards Consortium Study Data Tabulation Model standard terminology v.3.1.1. In another embodiment, the highest dose tolerated that is therapeutically effective is the highest dosage that is effective in the treatment of ASMD without causing an increase in the total bilirubin concentration relative to a patient's total bilirubin concentration prior to administration of ASM, which increase lasts for greater than two days, three days, five days, one week, two weeks, or three weeks. In another embodiment, the highest dose tolerated that is therapeutically effective is the highest dosage that is effective in the treatment of ASMD without causing a total bilirubin concentration of greater than normal total bilirubin concentrations that lasts for greater than 18 hours, 24 hours, 36 hours, 48 hours or 72 hours, 5 days, one week, two weeks or three weeks after administration of the dose of ASM. The normal total bilirubin concentration in a human without ASMD (e.g., a healthy human) is less than approximately 1.2 mg/dL. In certain embodiments, the highest dose tolerated that is therapeutically effective is the highest dosage that is effective in the treatment of ASMD without causing a total bilirubin concentration that is greater than approximately 1.5 mg/dL, 1.75 mg/dL, 2.0 mg/dL, 2.1 mg/dL, 2.2 mg/dL. 2.3 mg/dL, 2.4 mg/dL, 2.5 mg/dL, 2.6 mg/dL, 2.7 mg/dL, 2.75 mg/dL, 2.8 mg/dL, 2.9 mg/dL, 3.0 mg/dL, 3.1 mg/dL, 3.2 mg/dL, 3.3 mg/dL, 3.4 mg/dL, 3.5 mg/dL, 3.6 mg/dL, 3.7 mg/dL, 3.8 mg/dL, 3.9 mg/dL or 4 mg/dL or in the range of 2.1 mg/dL to 2.5 mg/dL, 2.1 mg/dL to 3.0 mg/dL, or 2.1 mg/dL to 4 mg/dL that lasts for greater than 18 hours, 24 hours, 36 hours, 48 hours or 72 hours, 5 days, one week, two weeks or three weeks after administration of the dose of ASM.

In another embodiment, the highest dose tolerated is the highest dosage that is effective in the treatment of ASMD without resulting in a plasma ceramide concentration that is greater than the normal plasma ceramide concentration 6 hours, 8 hours, 12 hours, 16 hours, 18 hours, 24 hours, 36 hours, 48 hours or 72 hours after administration of the dose of ASM. The normal plasma ceramide concentration in a human without ASMD (e.g., a healthy human) is approximately 1.5 to 8 µg/mL. In certain embodiments, the highest dose tolerated is the highest dosage that is effective in the treatment of ASMD without resulting in a plasma ceramide concentration of greater than approximately 8.2 µg/mL, 8.3 µg/mL, 8.4 µg/mL, 8.5 µg/mL, 8.75 µg/mL, 9 µg/mL, 9.5 µg/mL, 10 µg/mL, 11 µg/mL, 12 µg/mL, 13 µg/mL, 14 µg/mL, 15 µg/mL, 16 µg/mL, 17 µg/mL, 18 µg/mL, 19 µg/mL, 20 µg/mL, 25 µg/mL, 55 µg/mL, 60 µg/mL, 65 µg/mL, 70 µg/mL, 75 µg/mL, or 80 µg/mL, or in the range of 8.2 µg/mL to 10 µg/mL, 8.5 µg/mL to 10 µg/mL, 9 µg/mL to 12 µg/mL, 10 µg/mL to 12 µg/mL, 10 µg/mL to 15 µg/mL, 10 µg/mL to 20 µg/mL, 15 µg/mL to 20 µg/mL, or 20 µg/mL to 30 µg/mL 6 hours, 8 hours, 10 hours, 12 hours, 16 hours, 18 hours, 24 hours, 36 hours, 48 hours or 72 hours after administration of the dose of ASM.

In another embodiment, the highest dose tolerated that is therapeutically effective is the highest dosage that is effective in the treatment of ASMD without causing an acute phase response. An acute phase response can be assessed by a change in the concentration of an acute phase reactant, a change in prothrombin time, a change in partial thromboplastin time, or a change in the percentage of neutrophils. For example, an acute phase response can be assessed by an increase in one or more of the following factors following ASM administration to subject relative to those factors prior to administration of ASM to the subject or relative to those factors in a human without ASMD (e.g., a healthy human): the percentage of neutrophils, the prothrombin time (PT), the partial thromboplastin time (PTT), the total bilirubin concentration, C-reactive protein (CRP/hs-CRP) concentration, serum amyloid A (SAA), serum amyloid P component, angiotensin converting enzyme (ACE), ferritin concentration, albumin concentration or fibrinogen concentration. An acute phase response can also be assessed by a decrease in iron concentration or albumin concentration following ASM administration to a subject relative to the iron concentration or albumin concentration in the subject prior to ASM administration or relative to the iron concentration or albumin concentration in a human without ASM (e.g., a healthy human).

In a specific embodiment, the highest dose tolerated that is therapeutically effective is the highest dosage that is effective in the treatment of ASMD without causing an increase in CRP/hs-CRP concentration 6 hours, 8 hours, 12 hours, 16 hours, 18 hours, 24 hours, 36 hours, 48 hours or 72 hours after administration of the dose of ASM relative to a patient's CRP/hs-CRP concentration prior to administration of ASM. In another specific embodiment, the highest dose tolerated that is therapeutically effective is the highest dosage that is effective in the treatment of ASMD without resulting in a plasma CRP/hs-CRP concentration that is greater than the normal plasma CRP/hs-CRP concentration 6 hours, 8 hours, 12 hours, 16 hours, 18 hours, 24 hours, 36 hours, 48 hours or 72 hours after administration of the dose of ASM. The normal plasma CRP/hs-CRP concentration in a human without ASMD (e.g., a healthy human) is less than approximately 8 mg/L. In certain embodiments, the highest dose tolerated that is therapeutically effective is the highest dosage that is effective in the treatment of ASMD without causing a plasma CRP/hs-CRP concentration of greater than approximately 8.1 mg/L, 8.2 mg/L, 8.3 mg/L, 8.4 mg/L, 8.5 mg/L, 8.6 mg/L, 8.7 mg/L, 8.8 mg/L, 8.9 mg/L, 9 mg/L, 9.5 mg/L, 10 mg/L, 11 mg/L, or 12 mg/L, or in the range of 8.5 mg/L to 10 mg/L, or 8.5 mg/L to 12 mg/L, or 10 mg/L to 12 mg/L 6 hours, 8 hours, 12 hours, 16 hours, 18 hours, 24 hours, 36 hours, 48 hours or 72 hours after administration of the dose of ASM.

In a specific embodiment, the highest dose tolerated that is therapeutically effective is the highest dosage that is effective in the treatment of ASMD without causing an increase in ferritin concentration 6 hours, 8 hours, 12 hours, 16 hours, 18 hours, 24 hours, 36 hours, 48 hours or 72 hours after administration of the dose of ASM relative to a patient's ferritin concentration prior to administration of ASM. In another specific embodiment, the highest dose tolerated that is therapeutically effective is the highest dosage that is effective in the treatment of ASMD without resulting in a plasma ferritin concentration that is greater than the normal plasma ferritin concentration 6 hours, 8 hours, 12 hours, 16 hours, 18 hours, 24 hours, 36 hours, 48 hours or 72 hours after administration of the dose of ASM. The normal plasma ferritin concentration in a human without ASMD (e.g., a healthy human) is 10 to 30 ng/mL. In certain embodiments, the highest dose tolerated that is therapeutically effective is the highest dosage that is effective in the treatment of ASMD without causing a plasma ferritin concentration of greater than approximately 600 ng/mL, 625 ng/mL, 650 ng/mL, 675 ng/mL, 700 ng/mL, 725 ng/mL, 750 ng/mL, 775 ng/mL, 800 ng/mL, 850 ng/mL, 900 ng/mL, 950 ng/mL, 1000 ng/mL, 1050 ng/mL, 1100 ng/mL, 1150 ng/mL, or 1200 ng/mL or in the range of 600 ng/mL to 800 ng/mL, 650 ng/mL to 850 ng/mL, 600 ng/mL to 1000 ng/mL, 600 ng/mL to 1200 ng/mL, 800 ng/mL to 1000 ng/mL, 900 ng/mL to 1000 ng/mL, or 1000 ng/mL to 1200 ng/mL 6 hours, 8 hours, 12 hours, 16 hours, 18 hours, 24 hours, 36 hours, 48 hours or 72 hours after administration of the dose of ASM.

In a specific embodiment, the highest dose tolerated that is therapeutically effective is the highest dosage that is effective in the treatment of ASMD without causing an increase in fibrinogen concentration 6 hours, 8 hours, 12 hours, 18 hours, 24 hours, 36 hours, 48 hours or 72 hours after administration of the dose of ASM relative to a patient's fibrinogen concentration prior to administration of ASM. In another specific embodiment, the highest dose tolerated that is therapeutically effective is the highest dosage that is effective in the treatment of ASMD without resulting in a plasma fibrinogen concentration that is greater than the normal plasma fibrinogen concentration 6 hours, 8 hours, 12 hours, 16 hours, 18 hours, 24 hours, 36 hours, 48 hours or 72 hours after administration of the dose of ASM. The normal plasma fibrinogen concentration in a human without ASMD (e.g., a healthy human) is 150 mg/dL to 300 mg/dL. In certain embodiments, the highest dose tolerated that is therapeutically effective is the highest dosage that is effective in the treatment of ASMD without causing a plasma fibrinogen concentration of greater than approximately 350 mg/dL, 375 mg/dL, 400 mg/dL, 425 mg/dL, or 450 mg/dL, or in the range of 350 mg/dL to 400 mg/dL, 350 mg/dL to 450 mg/dL or 400 mg/dL to 450 mg/dL, 6 hours, 8 hours, 12 hours, 16 hours, 18 hours, 24 hours, 36 hours, 48 hours or 72 hours after administration of the dose of ASM.

In a specific embodiment, the highest dose tolerated that is therapeutically effective is the highest dosage that is effective in the treatment of ASMD without causing an increase in the percentage of neutrophils of total white blood cells 6 hours, 8 hours, 12 hours, 16 hours, 18 hours, 24 hours, 36 hours, 48 hours or 72 hours after administration of the dose of ASM relative to a patient's percentage of neutrophils of total white blood cells prior to administration of ASM. In another specific embodiment, the highest dose tolerated that is therapeutically effective is the highest dosage that is effective in the treatment of ASMD without resulting in a percentage of neutrophils of total white blood cells that is greater than the normal percentage of neutrophils of total white blood cells concentration 6 hours, 8 hours, 12 hours, 16 hours, 18 hours, 24 hours, 36 hours, 48 hours or 72 hours after administration of the dose of ASM. The normal percentage of neutrophils of total white blood cells in a human without ASMD (e.g., a healthy human) is 45% to 60%. In certain embodiments, the highest dose tolerated that is therapeutically effective is the highest dosage that is effective in the treatment of ASMD without causing an increase in the percentage of neutrophils of total white blood cells that is 70%, 75%, 80%, 85%, 90%, 95% or greater 6 hours, 8 hours, 12 hours, 18 hours, 24 hours, 36 hours, 48 hours or 72 hours after administration of the dose of ASM.

In another embodiment, the highest dose tolerated that is therapeutically effective is the highest dosage that is effective in the treatment of ASMD without causing an increase in antibodies to the administered ASM. In another embodiment, the highest dose tolerated that is therapeutically effective is the highest dosage that is effective in the treatment of ASMD without causing a hypersensitivity reaction. In another embodiment, the highest dose tolerated that is therapeutically effective is the highest dosage that is effective in the treatment of ASMD without causing cytokine release syndrome.

In certain embodiments, the highest dose tolerated by a subject that is therapeutically effective is 1 mg/kg to 2.5 mg/kg, 2 mg/kg to 3 mg/kg, 3 mg/kg to 5 mg/kg, 5 mg/kg to 10 mg/kg, 10 mg/kg to 15 mg/kg, 15 mg/kg to 20 mg/kg, 15 mg/kg to 25 mg/kg, 20 mg/kg to 30 mg/kg, or 25 mg/kg to 50 mg/kg. In some embodiments, the highest dose tolerated by a subject that is therapeutically effective is 1 mg/kg, 2 mg/kg, 3 mg/kg. 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, or 15 mg/kg. In certain embodiments, the highest dose tolerated by a subject that is therapeutically effective is 20 mg/kg, 25 mg/kg, 30 mg/kg, 35 mg/kg, 40 mg/kg, 45 mg/kg, or 50 mg/kg.

In certain embodiments, a dose of ASM described herein is administered every 3 days, every 4 days, every 5 days, every 6 days, every week, every 8 days, every 9 day, every 10 days, every 11 days, every 12 days, every 13 days, every 2 weeks, every 3 weeks, every 4 weeks, or every 5 weeks to a subject. In some embodiments, a dose of ASM described herein is administered every 3 to 5 days, every 3 to 7 days, every 5 to 7 days, every 5 to 10 days, every 5 to 14 days, every 7 to 14 days, every 2 to 4 weeks, or every 3 to 5 weeks to a subject. In certain embodiments, the frequency of administration of a dose of ASM changes as the dose is adjusted. For example, a dose of 0.3 mg/kg may be administered every week or two weeks and a dose of 1 mg/kg may be administered every two weeks or three weeks.

In some embodiments, a dose of ASM (e.g. a maintenance dose) is administered to a subject for a period for 12 weeks, 20 weeks, 25 weeks, 30 weeks, 35 weeks, 40 weeks, 45 weeks, 50 weeks, 52 weeks, 1 year, 1.5 years, 2 years, 2.5 years, 3 years, 3.5 years, 4 years or until the patient experiences a related adverse event, a total bilirubin value greater than the bilirubin value for a human without ASMD (e.g., a healthy human), a plasma ceramide concentration greater than the plasma ceramide concentration of a human without ASMD (e.g., a healthy human), or an acute phase response.

In certain embodiments, an initial low non-toxic dose of ASM is administered every 3 days, every 4 days, every 5 days, every 6 days, every week, every 8 days, every 9 day, every 10 days, every 11 days, every 12 days, every 13 days, every 2 weeks, every 3 weeks, every 4 weeks, or every 5 weeks to a subject. In some embodiments, a dose of ASM described herein is administered every 3 to 5 days, every 3 to 7 days, every 5 to 7 days, every 5 to 10 days, every 5 to 14 days, every 7 to 14 days, every 2 to 4 weeks, or every 3 to 5 weeks to a subject. In certain embodiments, the initial low non-toxic dose of ASM is administered for a period of 4 weeks, 6 weeks, 8 weeks, 12 weeks, 14 weeks or longer.

In certain embodiments, a successive increase in the dose of ASM is approximately 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.2 mg/kg, 1.5 mg/kg, 1.75 mg/kg, 2 mg/kg, 3 mg/kg. 4 mg/kg or 5 mg/kg higher than the previous dose. In some embodiments, a successive increase in the dose of ASM 0.1 to 0.5 mg/kg, 0.1 mg/kg to 1 mg/kg, 0.5 mg/kg to 1 mg/kg, 0.5 mg/kg to 2 mg/kg, 1 mg/kg to 2 mg/kg, 2 mg/kg to 4 mg/kg or 2 mg/kg to 5 mg/kg higher than the previous dose.

Doses of ASM described herein can be administered by any route that is useful in achieving a therapeutic effect. Specific routes of administration of doses of ASM include, but are not limited to, intravenous, intraventricular, intradermal, transdermal, subcutaneous, intramuscular, intranasal, inhalation, intrapulmonary, topical, transmucosal, intracranial, intrathecal, epidural and intra-synovial. In one embodiment, a dose of ASM is administered systemically (e.g., parenterally) to a subject in need thereof. In another embodiment, a dose of ASM is administered locally to a subject in need thereof.

The dose of ASM enzyme that is effective in treating the somatic (non-central nervous system) manifestations of ASMD is not able to effectively cross the blood-brain barrier. Thus, in specific embodiments, ASM is administered to a patient intraventicularly or intrathetically to the brain of a NPD patient. See, e.g., U.S. Patent Application Publication No. 2009/0130079 and 2009/0123451, which are incorporated herein by reference in their entirety, for methods for intraventricular delivery of lysosomal storage enzymes to the brain. In certain embodiments, the ASM is administered to a patient intracerebraventricularly. See, e.g., Dodge et al., 2009, Experimental Neurology 215: 349-357, which is incorporated herein by reference in its entirety, for methods for intracerebroventricular infusion of ASM. In some embodiments, the ASM is administered to a patient by indirect intra-parenchymal injections. See, e.g., Yang et al. 2007, Experimental Neurology 207: 258-266. In some embodiments, a modified form of ASM that targets the enzyme to the brain, such as described in Section 5.2, infra, is administered to a patient to treat ASMD.

Only a small percentage of the ASM enzyme administered to a patient reaches the lung. Thus, in specific embodiments, ASM is administered to the lungs of a patient. In certain embodiments, ASM is administered by intranasal or inhalation to a patient. See, e.g., Ziegler et al., 2009, Molecular Genetics and Metabolism 97: 35-42, which is incorporated herein by reference in its entirety, for information regarding the intranasal administration of ASM. In some embodiments, a modified form of ASM that targets the enzyme to the lung, such as described in Section 5.2, infra, is administered to a patient to treat ASMD. In certain embodiments, the ASM is administered to a patient using a nebulizer. Delivery of ASM to the lungs may occur by intrapulmonary injection through a bronchoscope, a metered-dose inhaler, or a nebulizer.

In certain embodiments, the ASM enzyme is administered systemically to a patient as well as locally administered to specific organs, such the brain and lung. In some embodiments, the locally administration of the ASM enzyme supplements the systemic administration of the enzyme. In specific embodiments, the ASM enzyme is administered locally to, e.g., the brain or lungs, after the accumulated sphingomyelin in the patient has been debulked by systemic administration (e.g., intravenous administration).

In certain embodiments, a patient is genotyped prior to the administration of ASM. In some embodiments, the glycosylation pattern of the ASM expressed by a patient is determined prior to administration of ASM. The administration of ASM that is similar/compatible with that endogenously expressed by a patient may reduce the potential for immunogenicity.

In certain embodiments, the activity of endogenously expressed ASM is determined prior to the administration of ASM. The activity of endogenously expressed ASM can be measured in DBS and in cultured fibroblasts using techniques known to one of skill in the art.

In a specific embodiment, the methods for treating ASMD provided herein reduce spleen volume as assessed by techniques known in the art, e.g., MRI. In another specific embodiment, the methods for treating ASMD provided herein reduce liver sphingomyelin levels as assessed by techniques known in the art, e.g., biochemical analysis and/or histomorphometric analysis of liver samples. In another specific embodiment, the methods for treating ASMD provided herein increase exercise capacity as assessed by techniques known in the art, e.g., maximum workload by cycle erogmetry, including percent predicted maximum workload, peak oxygen consumption, and carbon dioxide production. In another specific embodiment, the methods for treating ASMD provided herein increase in pulmonary function as assessed by techniques known in the art, e.g., DLco, FVC, FEV, and/or TLC. In another specific embodiment, the methods for treating ASMD provided herein decrease in bronchial alveolar lavage (BAL) sphinomyelin. In another specific embodiment, the methods for treating ASMD provided herein decrease in liver volume as assessed by techniques known in the art, e.g., MRI. In another specific embodiment, the methods for treating ASMD provided herein improve lung appearance as assessed by techniques known in the art, e.g., high resolution CT scan or chest X-ray. In another specific embodiment, the methods for treating ASMD provided herein improve lung clearance. In another specific embodiment, the methods for treating ASMD provided herein decrease in sphinomyelin concentration in the liver, skin, plasma and DBS. In another specific embodiment, the methods for treating ASMD provided herein reduce serum chitotriosidase levels. In another specific embodiment, the methods for treating ASMD provided herein reduce serum CCL18 levels. In another specific embodiment, the methods for treating ASMD provided herein improve a patient's lipid profile (e.g., decrease cholesterol). In another specific embodiment, the methods for treating ASMD provided herein reduce or ameliorate the severity of ASMD and/or a symptom associated therewith. In another specific embodiment, the methods for treating ASMD provided herein reduce the duration of a symptom associated with ASMD. In another specific embodiment, the methods for treating ASMD provided herein prevent the recurrence of a symptom associated with ASMD. In another specific embodiment, the methods for treating ASMD provided herein a reduces hospitalization of a subject. In another specific embodiment, the methods for treating ASMD provided herein reduces hospitalization length. In another specific embodiment, the methods for treating ASMD provided herein increases the survival of a subject. In another specific embodiment, the methods for treating ASMD provided herein reduces the mortality of subject. In another specific embodiment, the methods for treating ASMD provided herein decreases hospitalization rate of a subject. In another specific embodiment, the methods for treating ASMD provided herein reduces the number of symptoms associated with ASMD. In another specific embodiment, the methods for treating ASMD provided herein increases symptom-free survival of ASMD patients. In another specific embodiment, the methods for treating ASMD provided herein improve in neurological function (e.g., psychomotor function, social responsiveness, etc.) of a subject.

In another specific embodiment, the methods for treating ASMD provided herein improve a patient's quality of life. In certain specific embodiments, the method for treating ASMD provided herein improve a patient's quality of life as assessed by, e.g. the Brief Fatigue Inventory (BFI; Mendoza et al., 1999, Cancer 85(5): 1186-1196), the Brief Pain Inventory-Short Form (BPI-SF; Cleeland et al., 1994, Ann Acad Med Singapore 23(2): 129-138), the ASM-Health Assessment Questionnaire, which is a composite of the BFI, BPI-SF, and Short Form-36 Health Survey, the Chronic Respiratory Disease Questionnaire Self-Administered Standardized (CRQ-SAS; Schunemann et al., 2005, Eur. Respir. J. 25: 31-40) to assess dyspnea and fatigue, and the Activity Measure for Post-Acute Care (AM-PAC), a computer-adaptive test that assesses functional motilities (e.g., mobility, self-care, and applied cognition). Acid spHingomyelinase enzyme ASM refers to any form the acid sphinomyelinase enzyme that retains the ability to hydrolyze sphingomyelin to ceramide and phosphorylcholine as assessed by techniques known to one of skill in the art, such as those described in U.S. Pat. Nos. 4,039,388, 4,082,781, 5,686,240, and 7,563,591, and International Publication Nos. WO 2007/078806 and WO 2006/058385, which are incorporated herein by reference in their entirety. In a specific embodiment, an acid sphingomyelinase enzyme has the ability to hydrolyze sphingomyelin to ceramide and phosphorylcholine in the fluorescence-based, high-performance liquid chromatographic assay described in He et al., 2003, Analytical Biochemistry 314: 116-120. In a specific embodiment, an acid sphingomyelinase has at least 30%. 35%, 40%, 45%, 50%, 75%, 80%, 85%. 80%, 90%, 95% or 98%, or 30% to 50%, 40% to 50%, 50% to 75%, 50% to 90%, 75% to 80%, 75% to 90%, 75% to 95%, or 85% to 95% of the activity of ASM-1 (SEQ ID NO: 1, infra) as measured by, e.g., the assay described in He et al., 2003, Analytical Biochemistry 314: 116-120.

In a specific embodiment, the ASM is a human ASM. There are various isoforms of human ASM resulting from alternative splicing. One of the human ASM isoforms, human ASM isoform 1 (sometimes referred to as ASM-1), has the amino acid sequence found at UniProtKB/Swiss-Prot Accession No. P17405-1. Another human ASM isoform, human isoform 2 (sometimes referred to as ASM-2), has the amino acid sequence found at UniProtKB/Swiss-Prot. Accession No. P17405-2. A third human ASM isoform, human isoform 3 (sometimes referred to as ASM-3), has the amino acid sequence found at UniProtKB/Swiss-Prot. Accession No. P17405-3. The amino acid sequence of ASM-1, which is the most abundant isoform, is provided below:

```
        10         20         30         40
MPRYGASLRQ SCPRSGREQG QDGTAGAPGL LWMGLVLALA 50         60         70         80
LALALALSDS RVLWAPAEAH PLSPQGHPAR LHRIVPRLRD 90        100        110        120
VFGWGNLTCP ICKGLFTAIN LGLKKEPNVA RVGSVAIKLC 130        140        150        160
NLLKIAPPAV CQSIVHLFED DMVEVWRRSV LSPSEACGLL 170        180        190        200
LGSTCGHWDI FSSWNISLPT VPKPPPKPPS PPAPGAPVSR 210        220        230        240
ILFLTDLHWD HDYLEGTDPD CADPLCCRRG SGLPPASRPG 250        260        270        280
AGYWGEYSKC DLPLRTLESL LSGLGPAGPF DMVYWTGDIP 290        300        310        320
AHDVWHQTRQ DQLRALTTVT ALVRKFLGPV PVYPAVGNHE 330        340        350        360
STPVNSFPPP FIEGNHSSRW LYEAMAKAWE PWLPAEALRT 370        380        390        400
LRIGGFYALS PYPGLRLISL NMNFCSRENF WLLINSTDPA 410        420        430        440
GQLQWLVGEL QAAEDRGDKV HIIGHIPPGH CLKSWSWNYY 450        460        470        480
RIVARYENTL AAQFFGHTHV DEFEVFYDEE TLSRPLAVAF 490        500        510        520
LAPSATTYIG LNPGYRVYQI DGNYSGSSHV VLDHETYILN 530        540        550        560
LTQANIPGAI PHWQLLYRAR ETYGLPNTLP TAWHNLVYRM 570        580        590        600
RGDMQLFQTF WFLYHKGHPP SEPCGTPCRL ATLCAQLSAR 610        620
ADSPALCRHL MPDGSLPEAQ SLWPRPLFC
```

(SEQ ID NO:1). ASM-2 differs from ASM-1 in that amino acid residues 363 to 374 of ASM-1 (i.e., IGGFYALSPYPG (SEQ ID NO:2)) are replaced with amino acids YLSSVETQEGKR (SEQ ID NO:3) and amino acid residues 375 to 418 of ASM-1 are missing from ASM-2. ASM-3 differs from ASM-1 in that amino acid residues 363 to 418 of ASM-1 are missing from ASM-3. To the extent that ASM-2 and ASM-3 have enzymatic activity as measured by, e.g., the assay described in He et al. 2003, Analytical Biochemistry 314: 116-120, they are included as an ASM that could be administered to a subject. In a specific embodiment, to the extent that ASM-2 and ASM-3 have at least 30%, 35%, 40%, 45%, 50%, 75%, 80%, 85%, 80%, 90%, 95% or 98%, or 30% to 50%, 40% to 50%, 50% to 75%, 50% to 90%, 75% to 80%, 75% to 90%, 75% to 95%, or 85% to 95% of the activity of ASM-1 as measured by, e.g., the assay described in He et al., 2003, Analytical Biochemistry 314: 116-120, they are included as an ASM that could be administered to a subject.

In a specific embodiment, the human ASM has the amino acid sequence of human acid sphingomyelinase disclosed in SEQ ID NO: 1, supra, the amino acid sequence of a human acid sphingomyelinase disclosed in U.S. Pat. No. 6,541,218 (e.g. SEQ ID NO:2 in U.S. Pat. No. 6,541,218), or the amino acid sequence disclosed in FIG. 3 of Schuchman et al., 1991, J. Biol. Chem. 266: 8531-8539, each of which is incorporated herein by reference in its entirety.

In specific embodiments, the human ASM is the processed mature form. In other embodiments, the human ASM is the immature, unprocessed form. With respect to ASM-1, the immature form is 629 amino acids in length and contains the signal peptide found at amino acid residues 1 to 46. The mature form of ASM-1 lacks that signal peptide and is from amino acid residue 47 to amino acid residue 629. Human ASM-1 contains a saposin B-type domain from amino acid residues 85 to 169. With respect to ASM-1, the following amino acid residues are glycosylated (in particular, N-linked glycosylated): 86, 175, 335, 395, and 520.

In addition to the isoforms of human ASM, there are various naturally occurring variants of human ASM. For example, naturally occurring variants of the human ASM gene with different numbers of hexanucleotide repeat units occurring within the region of the gene encoding the putative signal peptide of ASM have been identified. See, e.g., Wan and Schuchman, 1995, Biochimica et Biophysica Acta 1270: 207-210 (which is incorporated herein by reference in its entirety) which the describes the identification of five alleles corresponding to nine, seven, six, five and four hexanucleotide repeats. Further, naturally occurring variants of human ASM with single amino acid variations have been identified. See, e.g., Schuchman et al., 1991, J. of Biol. Chem 266: 8531-8539 and Schuchman et al., 1991, Nucleic Acids Research 19(11): 3160, which are incorporated herein by reference in their entirety, for information regarding single polymorphisms. To the extent that any of the naturally occurring variants of human ASM have enzymatic activity as measured by, e.g. the assay described in He et al., 2003, Analytical Biochemistry 314: 116-120, they are included as an ASM that could be administered to a subject. In a specific embodiment, to the extent that any of the naturally occurring variants of human ASM have at least 30%, 35%, 40%, 45%, 50%, 75%, 80%, 85%, 80%, 90%, 95% or 98%, or 30% to 50%, 40% to 50%, 50% to 75%, 50% to 90%, 75% to 80%, 75% to 90%, 75% to 95%, or 85% to 95% of the activity of ASM-1 as measured by, e.g., the assay described in He et al., 2003, Analytical Biochemistry 314: 116-120, they are included as an ASM that could be administered to a subject.

Many single nucleotide polymorphisms (SNPs) for the gene encoding human ASM have been identified (see, e.g., the ncbi website: ncbi.nlm.nih.gov/projects/SNP/ for examples of SNPs). To the extent that any of the SNPs in the gene encode of an ASM that has enzymatic activity as measured by, e.g., the assay described in He et al., 2003, Analytical Biochemistry 314: 116-120, they are included as an ASM that could be administered to a subject. In a specific embodiment, to the extent that any of the SNPs in the gene encode of an ASM that has at least 30%, 35%, 40%, 45%, 50%, 75%, 80%, 85%, 80%, 90%, 95% or 98%, or 30% to 50%, 40% to 50%, 50% to 75%, 50% to 90%, 75% to 80%, 75% to 90%, 75% to 95%, or 85% to 95% of the activity of ASM-1 as measured by, e.g., the assay described in He et al., 2003, Analytical Biochemistry 314: 116-120, they are included as an ASM that could be administered to a subject. In certain embodiments, the ASM is a modified form of human ASM. In a specific embodiment, the modified form of human ASM is one disclosed in U.S. Pat. No. 7,527,956, which is incorporated herein by reference in its entirety. In another embodiment, the modified form of human ASM is one disclosed in International Publication No. WO 2008/136451, which is incorporated herein by reference in its entirety. In some specific embodiments, the ASM is a modified form of human ASM that has one, two or more of the following properties: (i) increased targeting to sites of pathology (e.g., the lung and/or brain) relative to unmodified human ASM, (ii) increased stability relative to unmodified human ASM, and (iii) increased activity relative to unmodified human ASM. Techniques known in the art can be used to measure the stability, activity and targeting of ASM. In a specific embodiment, the techniques described in Gamacho et al. 2008, J. Pharmacol. Exp. Ther. 325: 400-408 (which is incorporated herein by reference in its entirety) for assessing targeting of ASM are used. In another specific embodiment, the techniques described in He et al., 1999, Biochimica et Biophysica Acta 1432: 251-264 or Dhami et al., 2001. Lab. Invest. 81: 987-999 (which are incorporated herein by reference in their entirety) for assessing stability of the ASM are used. In another specific embodiment, the techniques described in He et al., 2003. Analytical Biochemistry 314: 116-120 (which is incorporated herein by reference in its entirety) for assessing ASM activity are used.

In one embodiment, the ASM is a modified form of human ASM that has increased enzymatic activity relative to unmodified human ASM, such as ASM-1. See, e.g., Qiu et al., 2003, J. Biol. Chem. 278(35): 32744-32752 and U.S. Pat. No. 7,527,956 for a mutant forms of recombinant human ASM with enzymatic activity with higher activity than wild-type recombinant human ASM (such as, e.g., ASM-1). In some embodiments, the ASM has increased enzymatic activity relative to unmodified human ASM (such as, e.g., ASM-1) due to the addition of zinc cations. See, e.g., Schissel et al., 1998, J. Biol. Chem 273: 18250-18259, which is incorporated herein by reference in its entirety, for a discussion regarding the role of zinc in ASM activity. In another embodiment, the ASM is a modified form of human ASM that has increased affinity for a natural receptor of human ASM (e.g., mannose 6-phosphate or high mannose) relative to unmodified human ASM (such as, e.g., ASM-1). In a specific embodiment, the ASM is conjugated to an oligosaccharide, such as described in U.S. Pat. No. 7,001,994 and International Patent Application Publication No. WO 2010/075010 and United States Patent Application Publication No. 2010/0173385 (which are incorporated herein by reference in their entirety), to increase the targeting the enzyme for its natural receptor. In another embodiment, the ASM is a modified form of human ASM that binds to an alternative receptor (e.g., intercellular adhesion molecule (ICAM)-1 which may increase targeting to organs such as the lung) than the natural receptor for ASM. In embodiment, the ASM is a modified form of human ASM that has increased stability relative to unmodified human ASM (such as, e.g., ASM-1).

In some embodiments, the ASM is conjugated or fused, directly or indirectly, to a targeting moiety, such as insulin-like growth factor (IGF)-I, IGF-II, leptin, granulocyte colony stimulating factor (G-CSF), or a humanized antibody that binds to human insulin receptor (HIR). See, e.g., U.S. Patent Application Publication No. 2009/0029467 and U.S. Pat. No. 7,560,424 (which is incorporated herein by reference in its entirety) for a discussion of the use of IGF-I as a targeting moiety for lysosomal storage enzymes, and U.S. Pat. No.

7,396,811 (which is incorporated herein by reference by reference in its entirety) for a discussion of the use of IGF-II as a targeting moiety for lysosomal storage enzymes. The targeting moieties IGF-I and IGF-II can facilitate targeting the ASM enzyme to the lyosome. For a discussion of the use of hormones, such as G-CSF and leptin as targeting moieties see, e.g., International Patent Application Publication No. WO 2007/091250 and U.S. Patent Application Publication No. 2010/0183577, which are incorporated herein by reference herein by reference in their entirety. See, e.g., U.S. Patent Application Publication No. 2004/0101904, which is incorporated herein by reference in its entirety, for a discussion of a humanized monoclonal antibody that binds human insulin receptor (HIR) linked to a pharmaceutical agent, such as an enzyme. The targeting moieties G-CSF, leptin and an antibody that binds to HIR can facilitate targeting of the ASM enzyme to the brain.

In certain embodiments, the ASM is a modified form of ASM (e.g., a modified form of human ASM) with a decrease in activity relative to unmodified ASM (such as, an unmodified human ASM, e.g., ASM-1). In some embodiments, the ASM is a modified form of ASM (e.g., a modified form of human ASM) with an increase in targeting to sites of pathology and a decrease in enzymatic activity relative to unmodified ASM (such as an unmodified human ASM, e.g., ASM-1).

In certain embodiments, the ASM is a highly phosphorylated form of ASM. See, e.g., U.S. Patent Application Publication No. 2002/0150981, which is incorporated herein by reference, for a discussion of techniques for producing highly phosphorylated forms of lysosomal enzymes.

The ASM enzyme can be produced by any method known in the art, including but not limited to recombinant DNA methods, cDNA cloning (see, e.g., Schuchman et al., 1991, J. Biol. Chem 266: 8531-8539 and U.S. Pat. No. 5,773,278, which are incorporated herein by reference in their entirety for cDNA clones of human ASM), genomic cloning, gene activation (see, e.g., U.S. Pat. No. 5,641,670, which is incorporated herein by reference in its entirety for gene activation techniques), or selected cell lines (e.g., mammalian, yeast, prokaryotic, insect cells (e.g. Sf9, Sf21, *Trichoplusia ni*, *Spodoptera frugiperda* and *Bombyx mori*), and plant cells) that produce high levels of the ASM enzyme. ASM as well as methods for producing ASM are described, e.g., in U.S. Pat. Nos. 5,773,278; 6,541,218; 5,686,240; and 7,527,956; each of which is incorporated herein by reference in its entirety.

In a specific embodiment, the ASM is a recombinantly produced ASM (e.g., a recombinantly produced human ASM). Cell expression systems which possess the cellular machinery and elements for the proper processing, i.e., signal cleavage, glycosylation, phosphorylation and protein sorting are preferred. For example, mammalian cell expression systems are preferred for the expression of biologically active enzymes that are properly folded and processed; when administered in humans such expression products should exhibit proper tissue targeting and no adverse immunological reaction.

In certain embodiments, the ASM (e.g., human ASM) is produced by overexpression of ASM cDNA in mammalian cells. In a specific embodiment, the human ASM is produced by overexpression of human ASM cDNA in Chinese hamster ovary (CHO) cells. See, e.g., He et al., 1999, Biochimia et Biophsyica Acta 1432: 251-264 for methods for overexpression of human ASM cDNA in CHO cells, and U.S. Pat. No. 6,541,218 each of which is incorporated by reference herein in its entirety. In certain embodiments, the human ASM is produced by overexpression of human ASM cDNA in CHO cells that co-express alpha-2,6-sialytransferase. See, e.g., U.S. Pat. No. 5,047,335, incorporated herein by reference in its entirety, which describes CHO cells engineered to express alpha 2,6-sialytransferase.

In another specific embodiment, the mammalian cells are human cells. Examples of human cells that may be used to recombinantly express ASM (e.g., human ASM) include, but are not limited to Crucell Per.C6 cells, HT 1080 cells, HeLa cells, HEK 293 cells, 293T cells, WI38 cells, HuT292 cells, LF 1043 (HEL) cells, MRC-5 cells, TMK-1 cells, BT483 cells, Hs578T cells, HTB2 cells, HTB3 cells, HTB4 cells, BT 20 cells, T47D cells. CRL7O3O cells, HsS78Bst cells, 721 cells, A2780 cells, A172 cells, A253 cells, COR-L23/R23 cells, COV-434 cells, DU145 cells, DuCaP cells, EM2 cells, Saos-2 cells. U373 cells, WM39 cells, L132 cells, A-5489 cells, G-293 cells, G-401 cells, CAKI-1 cells, RD cells, and YAR cells. Other exemplary human cells that may be used to express ASM include those human cell lines listed in the Immuno Polymorphism Database of the European Molecular Biology Laboratory, and the database of the U.S. National Institutes of Health, as well as those commercially available form, for example, the American Type Culture Collection, Manassas, Va., and Lifeline Cell Technology, Walkersville, Md. When using human cell lines for production, rhASM can be produced using cDNAs, gDNAs for hASM or by gene activation techniques such as those described in U.S. Pat. No. 5,641,670 which is incorporated by reference herein in its entirety.

Examples of other mammalian cells that may be used to produce ASM (e.g., human ASM) include, but are not limited to, Vero cells, VERY cells, BHK cells, COS cells, MDCK cells, or 3T3 cells. In certain embodiments, myeloma cells are used to produce ASM (e.g., human ASM). Non-limiting examples of myeloma cells include NS0 cells, 45.6 TG1.7 cells, AF-2 clone 9B5 cells, AF-2 clone 9B5 cells, J558L cells, MOPC 315 cells, MPC-1 cells. NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells.

In some embodiments, a plant cell culture system is used for expression of the ASM. See, e.g., U.S. Pat. Nos. 5,929, 304; 7,504,560; 6,770,799; 6,551,820; 6,136,320; 6,034,298; 5,914,935; 5,612,487; and 5,484,719, U.S. patent application publication Nos. 2009/0208477, 2009/0082548, 2009/0053762, 2008/0038232, 2007/0275014 and 2006/0204487, and Shoji et al., 2008, Vaccine. 26(23):2930-2934, and D'Aoust et al., 2008, J. Plant Biotechnology, 6(9):930-940 (which are incorporated herein by reference in their entirety) for plant cells and methods for the production of proteins utilizing plant cell culture systems. In particular, U.S. patent application Nos. 2009/0208477, 2008/0038232 and 2006/0204487 describe the expression and production of enzymatically active high mannose lysosomal enzymes using transgenic plant root, particularly carrot cells. In a specific embodiment, carrot cells are engineered to express ASM. In certain embodiments, algae (e.g., *Chlamydomonas reinhardtii*) may be engineered to express ASM (see, e.g., Rasala et al., 2010, Plant Biotechnology Journal (Published online Mar. 7, 2010, which is incorporated herein by reference in its entirety).

Tissue and cellular uptake of ASM is mediated by both the high mannose residues (e.g., in macrophages) and by mannose-6-phosphate (e.g., in liver). Thus, production of ASM with altered glycan content and/or phosphorylation may be desired to enhance drug distribution. For example, ASM can be produced by cells having a mutation, e.g., a knockout for, at least one Golgi processing mannosidase. In one embodiment, the mutation reduces the expression of the gene, reduces protein or activity levels, or alters the distribution or other post translational modifications of the mannosidase, e.g., the processing of the carbohydrate chains. In a specific embodiment, the mutation reduces the level of the Golgi processing mannosidase activity. The mutation can be in a class 1 processing mannosidase; a class 2 processing mannosidase; a class 1 processing mannosidase and a class 2 processing mannosidase. Class 1 processing mannosidase includes: Golgi mannosidase IA; Golgi mannosidase IB; Golgi mannosidase IC. Class 2 processing mannosidase includes: Golgi mannosidase II. See, e.g., International Patent Application Publication No. WO 02/15927 and U.S. Pat. No. 7,138,262, which are incorporated herein by reference in their entirety, for methods of producing a high mannose protein.

In certain embodiments, cells expressing ASM are cultured in the presence of mannosidase inhibitor, such as an antibody, kifunensine, swainsonine, mannostatin, 6-deoxy-1,4-dideoxy-1,4-imino-D-mannitol (6-deoxy-DIM), or 6-deoxy-6-fluoro-1,4-dideoxy-1,4-imino-D-mannitol (6-deoxy-6-fluoro-DIM). The culture of ASM in the presence of such inhibitors may result in the production of a high mannose ASM. In some embodiments, the cells expressing ASM include a nucleic acid sequence, such as an antisense molecule or ribozyme, which can bind to or inactivate a cellular mannosidase nucleic acid sequence, e.g., mRNA, and inhibit expression of the protein. See, e.g., International Patent Application Publication No. WO 02/15927 and U.S. Pat. No. 7,138,262, which are incorporated herein by reference in their entirety, for methods of producing a high mannose protein.

In certain embodiments, the carbohydrate chains of the ASM enzyme recombinantly expressed are remodeled by sequential treatment with various enzymes, such as neuraminidase, galactosidase and .beta.-N acetylglucosaminidase. See, e.g., U.S. Pat. No. 5,549,892, which is incorporated herein by reference in its entirety, for a methods for remodeling carbohydrate chains of a lysosomal enzyme.

Uptake of ASM, mediated by mannose-6-phosphate (M6P) can be enhanced by modification of ASM to produce highly phosphorylated mannose residues and M6P. For example, ASM can be modified by recombinant technology to introduce additional mannose-6-phosphate to the ASM for enhancing cellular uptake. See, e.g., Matsuoka et al., 2010 Mole. Ther. 18:1519-1526 which is incorporated herein by reference in its entirety. In other embodiments, ASM can be coupled to highly phosphorylated oligosaccharide derivatives containing mannose 6-phosphate (M6P). See, e.g., U.S. Pat. No. 7,001,994, U.S Patent Application Publication US2010/0173385 and International Publication No. WO2010/075010. In another approach, a yeast culture system can be used for the expression of recombinant ASM that contains additional highly phosphorylated mannose-6-phosphate residues. See, e.g., Akeboshi et al., 2009 Glycobiology 19(9):1002-1009 which is incorporated by reference herein in its entirety.

Once ASM has been produced, it may be isolated or purified by any method known in the art for isolation or purification of a protein, for example, by chromatography (e.g., ion exchange, high performance liquid chromatography, affinity, particularly by affinity for ASM, by Protein A, and sizing column chromatography), centrifugation, differential solubility, or by any other standard technique for the isolation or purification of proteins. Where the ASM enzyme is secreted by the cultured cells, ASM may be readily recovered from the culture medium. See, e.g., He et al., 1999, Biochimia et Biophsyica Acta 1432: 251-264 for methods for purifying ASM.

The ASM enzyme can be formulated for any route of administration (e.g., infusion, subcutaneous, intramuscular, intrathecal, intraventricular, intranasal, inhalation or intradermal). The ASM enzyme can be supplied in a lyophilized form that is reconstituted before use with, e.g. sterile saline (e.g., 0.9% sodium chloride) or sterile water. Alternatively, the ASM enzyme can be supplied in an aqueous form. In certain embodiments, ASM is administered to a subject in a formulation comprising zinc. In some embodiments, the ASM enzyme is administered to the patient by infusion using, e.g., a syringe pump or an infusion bag with a pump.

In certain embodiments, ASM is administered to a subject in a carrier, such as liposomes or a polycationic carrier. See, e.g., U.S. Pat. No. 5,716,614, which is incorporated herein by reference in its entirety, for a carriers that can be used to administered ASM. In some embodiments, the ASM administered to a subject in ICAM-1-target nanocarriers. See, e.g., Muro et al., 2006, Mol. Ther. 13(1): 135-141, which is incorporated herein by reference, for ASM delivery using ICAM-1-targeted nanocarriers.

5.2. Patient Populations

In specific embodiments, a subject treated for ASMD in accordance with the methods provided herein is a human who has or is diagnosed as having one or more mutations in the gene encoding acid sphingomyelinase. In particular embodiments, a subject treated for ASMD in accordance with the methods provided herein is a human who has or is diagnosed as having Niemann-Pick disease (NPD). In one embodiment, a subject treated for ASMD in accordance with the methods provided herein is a human who has or is diagnosed as having NPD Type A. In another specific embodiment, a subject treated for ASMD in accordance with the methods provided herein is a human who has or is diagnosed as having NPD Type B.

In certain embodiments, a subject treated for ASMD in accordance with the methods provided herein has one or more mutations in the SMPD1 gene. In some embodiments, the mutation is a missense mutation. In other embodiments, the mutation is a deletion that results is the deletion of one, two or more amino acid residues. In specific embodiments, a subject treated for ASMD in accordance with the methods provided herein has one or more of the mutations

TABLE 1

| Amino Acid Position of ASM-1 | Mutation |
| --- | --- |
| 49 | D → V in NPDB |
| 92 | C → W in NPDB |
| 103 | L → P in NPDA and NPDB |
| 130 | V → A in NPDB |
| 137 | L → P in NPDB |
| 157 | C → R in NPDB |
| 166 | G → R in NPDB |
| 176 | I → N in NPDB |
| 184 | P → L in NPDA/NPDB |
| 196 | A → P in NPDB |
| 200 | R → C in NPDB |
| 225 | L → M in NPDB |
| 225 | L → P in NPDB |
| 228 | R → C in NPDB |
| 228 | R → H in NPDA/NPDB |
| 232 | G → D in NPDB |
| 241 | A → V in NPDA/NPDB |
| 242 | G → R in NPDB |
| 244 | W → C in NPDB |

TABLE 1-continued

| Amino Acid Position of ASM-1 | Mutation |
|---|---|
| 245 | G → S in NPDA and NPDB |
| 246 | E → K in NPDA |
| 246 | E → Q in NPDA |
| 248 | S → R in NPDA and NPDB |
| 251 | D → E in NPDA/NPDB |
| 278 | D → A in NPDA/NPDB |
| 281 | A → T in NPDB |
| 289 | R → H in NPDB |
| 292 | Q → K in NPDA/NPDB |
| 294 | R → Q in NPDA |
| 302 | L → P in NPDA |
| 313 | Y → H in NPDA |
| 319 | H → Y in NPDA |
| 323 | P → A in NPDB. |
| 330 | P → R in NPDB |
| 341 | L → P in NPDA/NPDB |
| 357 | A → D in NPDB |
| 367 | Y → C in NPDA |
| 371 | P → S in NPDB |
| 376 | R → H in NPDB |
| 376 | R → L in NPDB |
| 379 | S → P in NPDB |
| 382 | M → I in NPDA |
| 383 | N → S in NPDB |
| 389 | N → T in NPDA |
| 390 | Missing in NPDA. |
| 391 | W → G in NPDB |
| 413 | A → V in NPDB |
| 421 | H → R in NPDA |
| 421 | H → Y in NPDB |
| 431 | C → R in NPDB |
| 432 | L → P in NPDB |
| 435 | W → C in NPDB |
| 436 | S → R in NPDB |
| 446 | Y → C in NPDA |
| 450 | L → P in NPDA |
| 452 | A → V in NPDB |
| 456 | G → D in NPDB |
| 463 | F → S in NPDA |
| 467 | Y → S in NPDA |
| 474 | R → W in NPDB |
| 475 | P → L in NPDA and NPDB |
| 480 | F → L in NPDB |
| 482 | A → E in NPDA |
| 485 | A → V in NPDB |
| 486 | T → A in NPDB |
| 488 | Y → N in NPDB |
| 494 | G → S in NPDB |
| 496 | R → C in NPDB |
| 496 | R → H in NPDA |
| 496 | R → L in NPDA |
| 514 | H → Q in NPDB |
| 515 | E → V in NPDB |
| 517 | Y → C in NPDA |
| 533 | W → R in NPDB |
| 537 | Y → H in NPDA |
| 549 | L → P in NPDB |
| 563 | D → Y in NPDB |
| 576 | K → N in NPDB |
| 577 | G → S in NPDA |
| 592 | Missing in NPDA. |
| 600 | R → H in NPDB |
| 600 | R → P in NPDB |
| 608 | Missing in NPDB |

See, e.g., Simonaro et al., 2002, Am. J. Hum. Genet. 71: 1413-1419, which is incorporated herein by reference, for mutations in the acid sphingomyelinase gene (designated SMPD1).

In certain embodiments, a subject treated for ASMD in accordance with the methods provided herein endogenously expresses ASM with 2 to 5%, 5 to 10%. 5 to 15%, 5 to 20%, 5% to 30%, or 20% to 30% of the activity of normal, human ASM, e.g., ASM-1. In some embodiments, a subject treated for ASMD in accordance with the methods provided herein endogenously expresses ASM with less than 30%, 25%, 20%, 15%, 10%, 5%, 4%. 3%, 2% or 1% of the activity of normal, human ASM. e.g., ASM-1. See, e.g., U.S. Pat. Nos. 4,039,388, 4,082,781, 5,686,240, and 7,563,591, and International Publication Nos. WO 2007/078806 and WO 2006/058385, which are incorporated herein by reference in their entirety, for techniques that can be used to measure the activity of ASM. In a specific embodiment, the fluorescence-based, high-performance liquid chromatographic assay described in He et al., 2003, Analytical Biochemistry 314: 116-120 (which is incorporated herein by reference) is used to measure the activity of ASM.

In certain embodiments, a subject treated for ASMD in accordance with the methods provided herein displays one or more symptoms of NPD. Symptoms of NPD include, but are not limited to, distended abdomens, hepatomegaly, splenomegly, hepatosplenomegaly, neutropenia, pulmonary disease, lymphoadenopathy, the presence of histochemically characteristic NPD foam cells, anemia (e.g., microcytic anemia), thrombocytopenia, recurrent vomiting, chronic constipation, growth failure (e.g., decreased liner growth and body weight), delayed puberty, recurrent bruising, recurrent bleeding, atherogenic lipid profile (high cholesterol, triglycerides, LDL, and low HDL), pain (headache, back, extremities, abdomen), fatigue, early satiety, low endurance, osteopenia, neurological manifestations, and respiratory difficulties (e.g., interstitial lung disease, shortness of breath). Neurological manifestation of NPD include cherry red spot, hypotonia, muscle weakness, psychomotor retardation, spasticity, social unresponsiveness, irritability, and seizures.

In certain embodiments, a subject treated for ASMD in accordance with the methods provided herein is a human subject that displays two or more clinical features consistent with non-neuropathic NPD. In specific embodiments, a subject treated for ASM in accordance with the methods provided herein is a human subject that displays two or more clinical features consistent with non-neuropathic NPD: thrombocytopenia, anemia, neutropenia, hepatomegaly, splenomegaly, and pulmonary disease. In other embodiments, a subject treated for ASMD in accordance with the methods provided herein is a human subject that displays two or more clinical features consistent with neuropathic NPD.

In certain embodiments, a subject treated for ASMD in accordance with the methods provided herein is a human with a spleen volume two, three, four, five, six, seven, eight, nine, ten, eleven or twelve times greater than the spleen volume of a healthy human as assessed by techniques known in the art, such as, e.g., magnetic resonance imaging (MRI). In specific embodiments, a subject treated for ASMD in accordance with the methods provided herein is a human with a spleen volume greater than eight times the spleen volume of a healthy human as assessed by techniques known in the art, such as, e.g. MRI. In some embodiments, a subject treated for ASMD in accordance with the methods provided herein is a human with a spleen volume eight to twelve, nine to twelve, ten to twelve, or twelve to fourteen times greater than the spleen volume of a healthy human as assessed by techniques known in the art, such as, e.g., MRI. In specific embodiments, a subject treated for ASMD in accordance with the methods provided herein is a human with a spleen volume ≥8 multiples of normal (MN) (i.e., 1.6% of body weight) as assessed by techniques known in the art, such as, e.g., MRI.

In certain embodiments, a subject treated for ASMD in accordance with the methods provided herein is a human with a diffusing capacity ($DL_{CO}$) between 20% to 80%, 25% to 80%, 30% to 80%, 40% to 80%, 50% to 80%, or 60% to 80% of the predicted $DL_{CO}$ of a healthy human. In some embodiments, a subject treated for ASMD in accordance with the methods provided herein is a human with a $DL_{CO}$ of between 20% to 90%, 25% to 90%, 30% to 90%, 40% to 90%, 50% to 90%, 60% to 90%, or 70% to 90% of the predicted $DL_{CO}$ of a healthy human. $DL_{CO}$ measures the rate of diffusion of a diffusion-limited gas (e.g., carbon monoxide) per minute across the alveolocapillary membrane. $DL_{CO}$ can be calculated by comparing the amount of carbon monoxide exhaled following a known amount of inhaled carbon monoxide. Techniques known in the art can be used to assess $DL_{CO}$.

In certain embodiments, a subject treated for ASMD in accordance with the methods provided herein is a human infant. In some embodiments, a subject treated for ASMD in accordance with the methods provided herein is a human that is 2 to 3 months old. 2 to 6 months old, 3 to 6 months old, 4 to 6 months old, 5 to 8 months old, or 6 to 9 months old. In other embodiments, a subject treated for ASMD in accordance with the methods provided herein is a human child. In some embodiments, a subject treated for ASMD in accordance with the methods provided herein is a human that is 1 to 3 years old. 2 to 3 years old, 3 to 5 years old, 4 to 5 years old, 5 to 7 years old, or 6 to 9 years old.

In certain embodiments, a subject treated for ASMD in accordance with the methods provided herein is a human adult. In other embodiments, a subject treated for ASMD in accordance with the methods described herein is a elderly human. In some embodiments, a subject treated for ASMD in accordance with the methods provided herein is a human that is 10 to 18 years old, 10 to 20 years old, 12 to 20 years old, 15 to 20 years old, 20 to 25 years old, 21 to 25 years old, 21 to 30 years old, 25 to 30 years old. 30 to 35 years old. 35 to 40 years old. 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In specific embodiments, a subject treated for ASMD in accordance with the methods provided herein is a human female. In other embodiments, a subject treated for ASMD in accordance with the methods provided herein is a human male. In certain embodiments, a subject treated for ASMD in accordance with the methods provided herein is a female human that is not pregnant or is not breastfeeding. In other embodiments, a subject treated for ASMD in accordance with the methods provided herein is a female human that is pregnant or will become pregnant, or is breastfeeding.

In certain embodiments, a subject treated for ASMD in accordance with the methods provided herein is a human that has not had a major organ transplant (e.g., liver or bone marrow transplant). In other embodiments, a subject treated for ASMD in accordance with the methods provided herein is a human that has had a major organ transplant (e.g., liver or bone marrow transplant). In some embodiments, a subject treated for ASMD in accordance with the methods provided herein is a human that has not had a total or partial splenectomy. In other embodiments, a subject treated for ASMD in accordance with the methods provided herein is a human that has had a total or partial splenectomy.

In certain embodiments, a subject treated for ASMD in accordance with the methods provided herein is a human that does not have or has not been diagnosed with one or more of the following: active hepatitis B, active hepatitis C, human immunodeficiency virus (HIV) infection, cirrhosis, or significant cardiac disease (e.g., moderate or severe pulmonary hypertension or valvular dysfunction, or less than 50%, less than 40%, less than 30% or less than 20% left ventricular ejection fraction by echocardiography). In other embodiments, a subject treated for ASMD in accordance with the methods provided herein is a human that has or has been diagnosed as having one or more of the following: active hepatitis B, active hepatitis C, an human immunodeficiency virus (HIV) infection, cirrhosis, or significant cardiac disease (e.g., moderate or severe pulmonary hypertension or valvular dysfunction, or less than 50%, less than 40%, less than 30% or less than 20% left ventricular ejection fraction by echocardiography).

In certain embodiments, a subject treated for ASMD in accordance with the methods provided herein is a human that does not have one or more of the following: an International Normalized Ratio (INR) of greater than 1.25, 1.5, 1.75 or 2, a platelet count of less than $60 \times 10^3$ per μL, an alanine aminotransferase (ALT) of greater than 250 IU/L, an aspartate aminotransferase of greater than 250 IU/L, or a total bilirubin greater than 1.5 mg/dL, 1.75 mg/dL or 2 mg/dL. In other embodiments, a subject treated for ASMD in accordance with the methods provided herein is a human that has one or more of the following: an International Normalized Ration (INR) of greater than 1.25, 1.5, 1.75 or 2, a platelet count of less than $60 \times 10^3$ per μL, an alanine aminotransferase (ALT) of greater than 250 IU/L, an aspartate aminotransferase of greater than 250 IU/L, or a total bilirubin greater than 1.5 mg/dL, 1.75 mg/dL or 2 mg/dL.

In certain embodiments, a subject treated for ASMD in accordance with the methods provided herein is a human that is not taking one or more of the following medications: chlorpromazine, imipramine or desipramine. In other embodiments, a subject treated for ASMD in accordance with the methods provided herein is a human that is taking one or more of the following medications: chlorpromazine, imipramine or desipramine.

In certain embodiments, a subject treated for ASMD in accordance with the methods provided herein is a human that is not taking herbal supplements or medications that may cause or prolong bleeding (e.g., anti-coagulants, ibuprofen, aspirin, garlic supplements, ginkgo, and ginseng), or have potential hepatotoxicity (e.g., 3-hydroxy-3-methyl glutaryl [HMG]-CoA reductase inhibitors, erythromycin, valproic acid, anti-depressants, kava and echinaecea). In other embodiments, a subject treated for ASMD in accordance with the methods provided herein is a human that is taking one or more of the following herbal supplementals or medications: anti-coagulants, ibuprofen, aspirin, garlic supplements, ginkgo, ginseng, 3-hydroxy-3-methyl glutaryl [HMG]-CoA reductase inhibitors, erythromycin, valproic acid, anti-depressants, kava and echinaecea.

In specific embodiments, a subject treated for ASMD in accordance with the methods provided herein is human that meets one, two or more, or all of the criteria for subjects in the working examples in Sections 6, 8, and 9 et seq.

5.3. Monitoring Treatment

In accordance with the method provided herein, a number of parameters (e.g., factors or markers) can be monitored before, during and/or after the administration of a dose of ASM. In certain embodiments, a physical examination is performed prior to administration of ASM and as needed or recommended during the course of treatment with ASM. A physical examination can include the following assessments: general appearance, skin, head, ears, eyes, nose, and throat (HEENT), lymph nodes, heart, lungs, abdomen, extremities/joints, neurological, mental status, and reflexes. In certain embodiments, vital signs, continuous heart rate, respiratory rate, temperature and oxygen saturation can be assessed before, during and/or after the administration of a dose of ASM. Heart rates can be monitored continuously by telemetry beginning, e.g., 6 hours before administration of a dose of ASM up to 72 hours after administration of a dose of ASM.

In specific embodiments, a complete blood count with differential, blood urea nitrogen (BUN), bicarbonate, creatinine, glucose, uric acid, calcium, phosphate, albumin, total protein, sodium, potassium, chloride, lactate dehydrogenase, creatine kinase, creatine kinase with MB fraction, and urinalysis (including urine color, appearance, specific gravity, pH, protein, glucose, ketones, bilirubin, hemoglobin, and microscopy if indicated) can be performed at the times specified before, during and/or after the administration of a dose of ASM. In certain embodiments, liver tests, coagulation studies, and/or fasting lipid profile can be performed before, during and/or after the administration of a dose of ASM. Liver functions tests can include assessing concentrations of alanine aminotransferase (ALT), aspartate aminotransferase (AST), alkaline phosphatase (AP), gamma-glutamyl transferase (GGT) and total and direct bilirubin. Coagulation studies can include assessing prothrombin time (PT), partial thromboplastin time (PTT), International normalized ratio (INR), D-dimer concentration, and fibrinogen concentration. Fasting lipid profile assessments can include assessments of total cholesterol (TC), low-density lipoprotein (LDL), high-density lipoprotein (HDL), very low-density lipoprotein (VLDL) and triglycerides.

In certain embodiments, a skin biopsy is performed prior to, during and/or subsequent to the administration of a dose of ASM. In some embodiments, a liver biopsy is performed prior to, during and/or subsequent to the administration of a dose of ASM. Sphingomyelin levels in skin and liver biopsies can be assessed by metamorph histological analysis.

In certain embodiments, pulmonary function tests are performed prior to, during and/or after the administration of a dose of ASM. Pulmonary function testing equipment calibration and test administration protocols can be standardized accordance with American Thoracic Society (ATS) guidelines (ATS, 1991, Am Rev Respir Dis 144: 1202-1218). In certain embodiments, percent predicted forced vital capacity (FVC) is assessed prior to, during and after the administration of a dose of ASM. FVC is the total volume of air expired during a forced maneuver. The FVC can be measured using standard spirometric techniques.

In certain embodiments, forced expiratory volume in 1 second (FEV1) can be performed prior to, during and after the administration of a dose of ASM. FEV1 is the volume of air expelled during the first second of FVC. The FEV1 can be measured using standard spirometric techniques.

In certain embodiments, total lung capacity (TLC) can be assessed prior to, during and after the administration of a dose of ASM. TLC is the total volume of air within the lungs following a maximal inspiratory effort. The TLC can be measured using whole body plethysmography.

In certain embodiments, DLco can be assessed prior to, during and after the administration of a dose of ASM. DLco measures the rate of diffusion of a diffusion-limited gas (carbon monoxide, CO) per minute across the alveolocapillary membrane. DLco can be calculated by comparing the amount of carbon monoxide (CO) exhaled following a known amount of inhaled CO. Helium, which does not diffuse across the alveolocapillary membrane, can be included as a tracer with the inspired CO to control for air trapping.

In certain embodiments, a chest X-ray (posterior-anterior and lateral) can be obtained prior to, during and/or after the administration of a dose of ASM. In certain embodiments, an abdominal MRI is obtained before, during and/or after the administration of a dose of ASM.

In certain embodiments, a blood sample is collected before, during and/or after administration of a dose of ASM for assessment of biomarkers, bilirubin concentration, and the percentage of neutrophils of total white blood cells. In a specific embodiment, the concentration of one or more of the following biomarkers is assessed using techniques known to one skilled in the art: CRP/hs-CRP concentration, sphingomyelin concentration, iron concentration, ferritin concentration, calcitonin concentration, albumin concentration, SAA, serum amyloid P component, ACE, CCL18, chitotriosidase, transferrin, fibrinogen concentration, and plasma sphingomyelin concentration, plasma ceramide concentration. In certain embodiments, the concentration of one or more of the following cytokines is assessed using techniques known to one skilled in the art: IL-6 and IL-8.

In certain embodiments, the concentration of antibodies against ASM (e.g., anti-recombinant human ASM IgG and/or anti-recombinant human ASM IgE) is assessed before, during and/or after the administration of a dose of ASM. In some embodiments, the concentration of one, two or more complement factors are assessed before, during and/or after the administration of a dose of ASM. In certain embodiments, the concentration of serum tryptase is assessed before, during and/or after the administration of a dose of ASM. In certain embodiments, a skin test to determine IgE-mediated reactions to ASM is assessed before, during and/or after the administration of a dose of ASM.s.

In certain embodiments, the pharmacokinetic profile for ASM is measured before, during and/or after the administration of a dose of ASM. In some embodiments, the BAL cell count is measured before, during and/or after the administration of a dose of ASM. See Section 8 et seq, infra, for other parameters that may be assessed before, during and/or after the administration of a dose of ASM.

In certain embodiments, a factor or marker described herein is assessed 1 week, 72 hours, 48 hours, 24 hours, 12 hours, 6 hours, 4 hours, 2 hours, 1 hour, 30 minutes or 15 minutes before the administration of a dose of ASM. In some embodiments, a factor or marker described herein is assessed during the administration of a dose of ASM. For example, a factor or marker described herein is assessed during the administration of a dose of ASM. In certain embodiments, a factor or marker described herein is assessed 15 minutes, 30 minutes, 1 hour, 2 hours, 4 hours, 6 hours, 8 hours 12 hours, 16 hours, 18 hours, 24 hours, 36 hours, 48 hours, 72 hours, 4 day, 5 days, 6 days, 1 week, two weeks, three weeks, four weeks, one month, two months, three months or longer after the administration of a dose of ASM. In certain embodiments, a factor or marker described herein is assessed some many hours or weeks after a certain number of doses of ASM. For example, a factor or marker described herein may be assessed every four weeks, month, 2 months, 3 months, 4 months, 5 months or 6 months after a certain number of doses of ASM. In certain embodiments, a factor or marker is assessed every 4 weeks, month, 2 months, 3 months, 4 months 5 months, 6 months, 7 months, 8 months. 9 months, 10 months, 11 months, or 12 months. In some embodiments, a factor or marker is assessed every month to 2 months, every month to 4 months, every 2 months to 4 months, every 2 months to 4 months, every 3 months to 4 months, every 2 months to 5 months, every 3 months to 5 months, every 4 months to 5 months, every 2 months to 6 months, every 3 months to 6 months, every 4 months to 6 months, or every 5 months to 6 months. In certain embodiments, a factor or marker is assessed every 6 months to 8 months, every 6 months to 12 months, every 8 months to 12 months, every 9 months to 12 months, or every 10 months to 12 months. In some embodiments, one or more factors or markers described herein is not assessed before, during and/or after the administration of a dose of ASM.

In certain embodiments, the results from the assessment of one or more factors or markers indicates that the dosage of ASM should be adjusted.

5.4. Biological Samples

In accordance with the methods described herein, a biological sample is subjected to one or more pretreatment steps prior to the detection and/or measurement of a cell population, factor or marker (e.g., biomarker). In certain embodiments, a biological fluid is pretreated by centrifugation, filtration, precipitation, dialysis, or chromatography, or by a combination of such pretreatment steps. In other embodiments, a tissue sample is pretreated by freezing, chemical fixation, paraffin embedding, dehydration, permeabilization, or homogenization followed by centrifugation, filtration, precipitation, dialysis, or chromatography, or by a combination of such pretreatment steps. In certain embodiments, the sample is pretreated by removing cells of a certain type from the sample, or removing debris from the sample prior to the determination of the number or amount of a particular cell type(s) in the sample according to the methods described herein.

The biological sample can be a tissue sample, biological fluid, discharge, or any other sample from a human subject. In some embodiments, the biological sample is a blood sample or bone marrow sample. In certain embodiments, the biological sample is a tissue sample (e.g., a liver, skin or lung biopsy). In some embodiments, the biological sample is a biological fluid such as urine. In certain embodiments, the biological sample is a sputum or nasal discharge sample. In some embodiments, the biological sample is mouth swab.

Techniques known in the art can be used to assess the presence, number, amount or percentage of a certain type(s) of cells present in a biological sample. For example, cells can be sorted using a using a fluorescence activated cell sorter (FACS). Fluorescence activated cell sorting (FACS) is a known method for separating particles, including cells, based on the fluorescent properties of the particles. See, for example, Kamarch, 1987, Methods Enzymol 151:150-165. Laser excitation of fluorescent moieties in the individual particles results in a small electrical charge allowing electromagnetic separation of positive and negative particles from a mixture. An antibody or ligand used to detect an antigenic determinant present on the cell surface of particular cells is labeled with a fluorochrome, such as FITC or phycoerythrin. The cells are incubated with the fluorescently labeled antibody or ligand for a time period sufficient to allow the labeled antibody or ligand to bind to cells. The cells are processed through the cell sorter, allowing separation of the cells of interest from other cells. FACS sorted particles can be directly deposited into individual wells of microtiter plates to facilitate separation.

Magnetic beads can be also used to separate cells. For example, cells can be sorted using a using a magnetic activated cell sorting (MACS) technique, a method for separating particles based on their ability to bind magnetic beads (0.5-100 μm diameter). A variety of useful modifications can be performed on the magnetic microspheres, including covalent addition of an antibody which specifically recognizes a cell-solid phase surface molecule or hapten. A magnetic field is then applied, to physically manipulate the selected beads. In a specific embodiment, antibodies to a blood cell surface marker are coupled to magnetic beads. The beads are then mixed with the blood cell culture to allow binding. Cells are then passed through a magnetic field to separate out cells having the blood cell surface markers of interest. These cells can then be isolated.

In some embodiments, the surface of a culture dish may be coated with antibodies, and used to separate cells by a method called panning. Separate dishes can be coated with antibody specific to particular cells. Cells can be added first to a dish coated with blood cell specific antibodies of interest. After thorough rinsing, the cells left bound to the dish will be cells that express the cell markers of interest. Examples of cell surface antigenic determinants or markers include, but are not limited to, CD2 for T lymphocytes and natural killer cells, CD3 for T lymphocytes, CD11a for leukocytes, CD28 for T lymphocytes, CD19 for B lymphocytes, CD20 for B lymphocytes, CD21 for B lymphocytes, CD22 for B lymphocytes, CD23 for B lymphocytes, CD29 for leukocytes, CD14 for monocytes. CD41 for platelets, CD61 for platelets, CD66 for granulocytes, CD67 for granulocytes and CD68 for monocytes and macrophages.

The presence, concentration or amount of a marker (including a biomarker) or factor can be assessed used techniques known in the art. The presence, concentration or amount of a marker (including a biomarker) or factor can be measured at the protein level and/or RNA level using techniques known to one skilled in the art. At the protein level, immunoassays, such as ELISAs and immunoprecipitation and western blots can be used to measure the presence, concentration or amount of a marker (including a biomarker) or factor. In addition, FACS can be used to measure the presence, concentration or amount of a marker (including a biomarker) or factor. At the RNA level, RT-PCR and Northern blots can be used to measure the presence, concentration or amount of a marker (including a biomarker) or factor.

5.5. Co-Therapies

In some embodiments, a method for treating ASMD involves the administration of ASM in combination with one or more additional therapies. As used herein, the term "in combination," refers, in the context of the administration of ASM, to the administration of a dose ASM prior to, concurrently with, or subsequent to the administration of one or more additional therapies (e.g., agents) for use in treating ASMD. The use of the term "in combination" does not restrict the order in which ASM and one or more additional therapies are administered to a subject. In specific embodiments, the interval of time between the administration of a dose of ASM and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, a dose ASM and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering a dose of ASM every 2 to 4 weeks, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, ASM and one or more additional therapies are cyclically administered to a subject. Cycling therapy involves the administration of ASM for a period of time, followed by the administration of one or more additional therapies for a period of time, and repeating this sequential administration. In certain embodiments, cycling therapy may also include a period of rest where ASM or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month. 2 months, 3 months, 4 months. 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating ASMD provided herein comprise administering ASM as a single agent for a period of time prior to administering ASM in combination with an additional therapy. In certain embodiments, the methods for treating ASMD provided herein comprise administering an additional therapy alone for a period of time prior to administering ASM in combination with the additional therapy.

In some embodiments, the administration of ASM and one or more additional therapies in accordance with the methods presented herein have an additive effect relative the administration of ASM or said one or more additional therapies alone. In some embodiments, the administration of ASM and one or more additional therapies in accordance with the methods presented herein have a synergistic effect relative to the administration of ASM or said one or more additional therapies alone.

As used herein, the term "synergistic." refers to the effect of the administration of a dose ASM in combination with one or more additional therapies (e.g., agents), which combination is more effective than the additive effects of any two or more single therapies (e.g., agents). In a specific embodiment, a synergistic effect of a combination therapy permits the use of lower dosages (e.g. sub-optimal doses) of ASM or an additional therapy and/or less frequent administration of ASM or an additional therapy to a subject. In certain embodiments, the ability to utilize lower dosages of ASM or of an additional therapy and/or to administer ASM or said additional therapy less frequently reduces the toxicity associated with the administration of ASM or of said additional therapy, respectively, to a subject without reducing the efficacy of ASM or of said additional therapy, respectively, in the treatment of ASMD. In some embodiments, a synergistic effect results in improved efficacy of ASM and each of said additional therapies in treating ASMD. In some embodiments, a synergistic effect of a combination of ASM and one or more additional therapies avoids or reduces adverse or unwanted side effects associated with the use of any single therapy.

In particular embodiments, one or more additional therapies are administered in combination with ASM to subjects to reduce or ameliorate one or more of the following that may be associated with the administration of a particular dose of ASM: (i) a related adverse event, (ii) a total bilirubin value greater than the bilirubin value for a human without ASMD (e.g., a healthy human), (iii) a plasma ceramide concentration greater than the plasma ceramide concentration of a human without ASMD (e.g., a healthy human), or (iv) an acute phase response. In specific embodiments, one or more additional therapies are administered in combination with ASM to subjects to increase pulmonary function while minimizing one or more of the following that may be associated with the administration of a particular dose of ASM: (i) a related adverse event, (ii) a total bilirubin value greater than the bilirubin value for a human without ASMD (e.g., a healthy human), (iii) a plasma ceramide concentration greater than the plasma ceramide concentration of a human without ASMD (e.g., a healthy human), or (iv) an acute phase response.

In certain embodiments, one or more additional therapies administered in combination with ASM to a subject to control or relieve symptoms associated with ASMD. In some embodiments, one or more additional therapies that are administered in combination with ASM to a subject are pain relievers. Specific examples of therapies can be administered in combination with ASM include, but are not limited to, N-Acetyl-L-cysteine (NAC), S-Adenosyl-L-methionine (SAM), interleukin (IL)-6 antibody, IL-6 receptor antibody, dexamethasone, L-Nil, (a selective inhibitor of inducible NOS), L-NAME (a selective inhibitor of NOS), basic fibroblast growth factor (b-FGF), imipramine (a sphingomyelinase inhibitor), D609 (a sphingomyelinase inhibitor), and N-oleoylethanolamine (NOE; a ceramide inhibitor).

In certain embodiments, chaperones, such as small molecule chaperones, are administered in combination with ASM. See, e.g., U.S. Pat. No. 7,750,050 and International Publication Nos. WO 2004/045574 and WO 2010/015816, which are incorporated by reference herein, for agents (e.g., small molecules) that may be administered in combination with ASM to a subject. In some embodiments, the chaperone (e.g. small molecule chaperone) does one, two or all of the following: increases the targeting of ASM to sites of pathology, stabilizes the activity of the ASM, and enhances the activity of the ASM.

In some embodiments, a glucocorticosteroid, such as dexamethasone, are administered in combination with ASM. See, e.g., U.S. Pat. No. 7,658,916, which is incorporated herein by reference in its entirety, for agents (e.g., glucocorticosteriods) that can be administered in combination with ASM.

In some embodiments, a substrate reduction molecule is administered in combination with ASM to a subject. In specific embodiments, a molecule (e.g., a small molecule) that either decreases the amount of sphingomyelin, reduces the rate of sphingomyelin synthesis, or both is administered in combination with ASM to a subject. See, e.g., Li et al. 2007, Biochim Biophys Act 1771(9):1186-1194 (which is incorporated herein by reference in its entirety) for sphingomyelin synthase inhibitors, such as tricyclodecan-9-yl-xanthogenate and sphingomyelin synthase siRNAs.

In some embodiments, a therapy that reduces the potential immunogenicity of ASM is administered in combination with ASM to a subject. In certain embodiments, benadryl is administered in combination with ASM to a subject.

The combination of ASM and one or more additional therapies can be administered to a subject in the same pharmaceutical composition. Alternatively, ASM and one or more additional therapies can be administered concurrently to a subject in separate pharmaceutical compositions. ASM and one or more additional therapies can be administered sequentially to a subject in separate pharmaceutical compositions. ASM and one or more additional therapies may also be administered to a subject by the same or different routes of administration.

5.6. Pharmaceutical Products

In one aspect, described herein are finished packaged and labeled pharmaceutical products. In one embodiment, a pharmaceutical product comprises a unit dosage form of ASM in an appropriate vessel or container (e.g., a glass vial or other container that is hermetically sealed). In some embodiments, the unit dosage form is a lyophilized form of ASM, and under those circumstances, the pharmaceutical product may contain a second container with sterile saline or sterile water for reconstituting the lyophilized form of ASM. In other embodiments, the unit dosage form is an aqueous form of ASM that does not require reconstitution before administration to a subject. In specific embodiments, the unit dosage form of ASM contains ASM in an amount sufficient for the administration of a low, non-toxic dose of the enzyme to a subject. In certain embodiments, the unit dosage form is suitable for the selected route of administration of the ASM to the subject. In a specific embodiment, the unit dosage form is suitable for intravenous delivery to a subject.

In one embodiment, a pharmaceutical product comprises a unit dosage form of ASM in an appropriate vessel or container (e.g., a glass vial or other container that is hermetically sealed) and an infusion pump or syringe pump for the administration of the ASM to a subject.

As with any pharmaceutical product, the packaging material and container are designed to protect the stability of the product during storage and shipment. Further, the pharmaceutical product includes instructions for use or other informational material that advise the physician, technician or patient on how to appropriately treat ASMD. In other words, the pharmaceutical product includes instruction means indicating or suggesting a dosing regimen including, but not limited to, actual doses (e.g., a dose escalation protocol), monitoring procedures, and other monitoring information. In certain embodiments, the pharmaceutical produce includes a means for genotyping a patient (e.g., PCR primers for the SMPD1 gene).

6. EXAMPLE 1

Human Trial of Recombinant Human Acid Sphingomyelinase (rhASM) Enzyme Replacement Therapy in Human Adults with ASM Deficiency

6.1. Introduction

ASMD is an autosomal recessive, lysosomal storage disorder that results when sphingomyelin is unable to be normally catabolized to ceramide and phosphorylcholine. Consequently, sphingomyelin accumulates within cells primarily of the reticuloendothelial system, leading to hepatosplenomegaly, anemia, thrombocytopenia, and interstitial lung disease. Growth retardation and an atherogenic lipid profile also are common findings. Patients who have little to no residual ASM activity exhibit the most severe symptoms with onset in infancy, failure to thrive, neurodegeneration, and death by age 3 (Niemann-Pick disease type A, NPD A). Patients with higher amounts of residual ASM activity have variable ages of onset, heterogeneous presentations and somatic symptoms, little to no neurologic involvement, and generally survive into adulthood (NPD B). Currently, there is no treatment for patients with ASMD.

Enzyme replacement therapy (ERT) has been successfully used to treat several lysosomal storage disorders, including Gaucher disease, Mucopolysaccharidosis types I, II, and VI, Fabry disease, and Pompe disease. Recombinant human lysosomal enzymes are administered intravenously and taken up into cells by receptor-mediated endocytosis for subsequent targeting to lysosomes. Proof of principle for the treatment of ASMD was demonstrated by Dr. Edward Schuchman's laboratory (Mount Sinai Medical Center) in an ASM knockout mouse (ASMKO) model where intravenous injections of recombinant human ASM (rhASM) efficiently reduced sphingomyelin levels in liver and spleen, and to a lesser extent in lung (Miranda, et al., FASEB 2000; 14:1988). However, sphingomyelin levels were not reduced in brain because of the inability of rhASM to cross the blood-brain barrier. Due to the fact that the ASMKO mouse has no residual ASM activity or protein and develops rapid and severe neurological disease, this animal is considered most appropriately a model of NPD—type A (see, Buccinna et al., 2009, J. Neurochem. 109:105-115).

Additional studies confirmed that biweekly doses of rhASM reduced sphingomyelin levels in ASMKO mice in a dose-dependent manner (0.3-3 mg/kg). The no observed adverse effect levels (NOAEL) for single and repeat dosing were determined to be 0.3 and 3 mg/kg, respectively in ASMKO mice. Subsequent attempts to deplete sphingomyelin levels in lung with higher doses of rhASM led to unexpected toxicity. At doses ≥10 mg/kg, ASMKO mice but not normal animals experienced liver inflammation, adrenal hemorrhage, cardiovascular shock and death in the setting of very elevated cytokine levels, suggesting cytokine release syndrome. The toxicity and cytokine elevations seen with high doses of rhASM could be ameliorated or prevented by prior treatment of ASMKO mice with several lower doses of rhASM, suggesting that the rate and amount of sphingomyelin degradation plays a key role.

In the ASMKO mouse, a model for NPD-type A, toxicity was not observed following single doses of ≤0.3 mg/kg rhASM and repeat doses of ≤ of 3.0 mg/kg rhASM; severe toxicity was not observed until single doses ≥10 mg/kg rhASM were administered. Therefore, a conservative starting dose of 0.03 mg/kg rhASM was selected for single-dose treatment of human subjects to ensure a 10-fold safety margin with respect to the single-dose NOAEL (0.3 mg/kg) observed in ASMKO mice. A maximum dose of 1.0 mg/kg rhASM was selected for single dose treatment of human subjects to ensure a 10-fold safety margin with respect to the dose at which serious toxicity was observed in the ASMKO mouse (10 mg/kg). Upon completion of the protocol set forth below, toxicity in the human subjects was unexpectedly observed with a dose as low as 0.3 mg/kg rhASM.

6.2. Materials and Methods

6.2.1. Human Protocol Design

Figure 1:
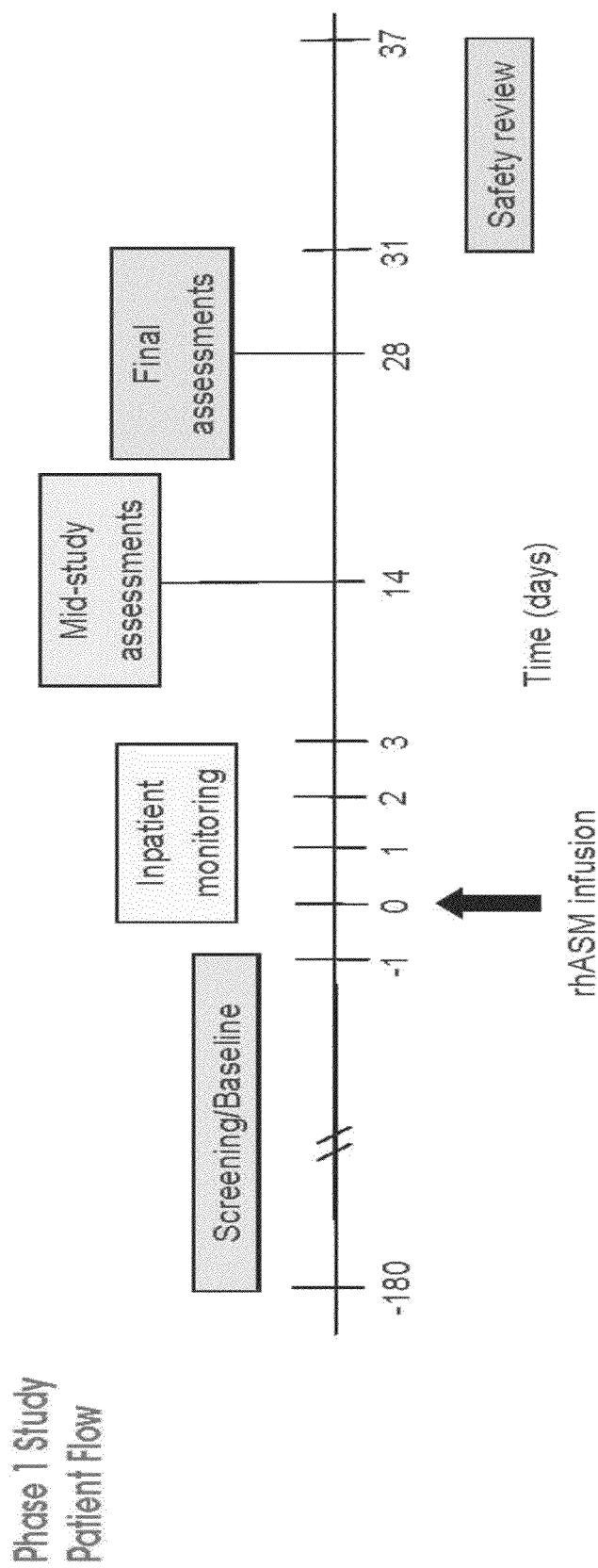
FIG. 1 is a graphic representation of the protocol design.

This protocol was a single-center, single-dose, dose escalation Phase 1 trial. The primary trial objectives were to evaluate the safety and pharmacokinetics of single doses of rhASM in human adults with non-neuronopathic ASMD (Niemann-Pick B). Single doses of 0.03, 0.1, 0.3, 0.6 and 1.0 mg/kg rhASM were infused sequentially by dose cohort. The original trial design called for a minimum of 15 patients (5 cohorts of 3 patients each). Due to difficulties with patient enrollment, the protocol was amended such that the first 2 cohorts enrolled 3 patients each and the last 3 cohorts were to enroll 2 patients each. An independent data monitoring committee oversaw the conduct of the trial and all protocol procedures were approved by the IRB. FIG. 1 depicts the protocol patient flow.

6.2.2. Patients

To be eligible for the protocol, patients had to be 18-65 years of age and have deficient ASM enzyme activity, a spleen volume ≥2× normal, AST and ALT ≤250 IU/L, bilirubin ≤3.6 mg/dL, INR ≤1.5, DLco>30% predicted, and platelets ≥60,000/mL. Patients were excluded if they had cirrhosis (by liver biopsy), significant cardiac disease, total splenectomy, or were taking medications or herbal supplements that were potentially hepatotoxic, promoted bleeding, or inhibited rhASM.

A total of 13 patients were enrolled and 11 patients infused with rhASM. rhASM was produced by over-expression of ASM cDNA in Chinese hamster ovary cells. The mean age of infused patients was 30.8 yrs, all were Caucasian (non-Hispanic/non-Latino), and mean spleen volume was 10.8 multiples of normal. One had a partial splenectomy; the remaining patients had intact spleens at protocol entry. FIG. 2 depicts the demography and baseline characteristics of the patients in this protocol.

Once screening was completed and eligibility was confirmed, patients were admitted to the cardiac care unit (CCU) overnight for baseline telemetry and infused the following morning with rhASM. Patients were monitored for 72 hrs post-dose while on telemetry (24 hrs in the CCU and 48 hrs in the General Clinical Research Center). Patients returned for an overnight visit on Day 14 and an outpatient visit on Day 28.

The following sets forth the medical assessments that were made during the protocol:

Physical exam—Days 0, 1, 2, 14, and 28
Chemistries, hematology, and urinalysis—preinfusion, then 24, 48, 72 hrs; Days 14, 28
Liver function tests—preinfusion, then q12 hrs through 72 hrs. Days 14, 28, Aldosterone, cortisol, delta-4-androstenedione—preinfusion, then q12 hrs through 72 hrs
ACTH stimulation test—Screening, Day 14 Telemetry—continuous through 72 hrs ECG, echocardiogram—preinfusion, end of infusion, and postinfusion at 1, 2, 6, 12, and 4 hrs, Day 14
Cardiac biomarkers (BNP, cardiac troponin-I, CPK-MB)—preinfusion, then 2, 6, 12, 24 hrs
Sphingomyelin, ceramide levels in plasma—preinfusion, then 24, 48, 72 hrs; Days 14 and 28
Pulmonary function testing and CXR—Screening, Day 14
Liver and spleen volumes by MRI—Screening, Day 14
Liver and skin biopsies—Screening, Day 14
Biomarkers—predose, Days 14, 28
Anti-rhASM IgG testing—preinfusion, Day 28
Pharmacokinetics—within 30 min preinfusion, 15 min after start of infusion, end of infusion, and at following time points post-infusion: 15 min, 30 min, 45 min; 1 hr., 2, 3, 4, 6, 8, 12, 18, 24, 48, 72 hrs.
Cytokines (IL-1a, IL-1b, IL-6, G-CSF, GM-CSF, MIP-1a, TNF-a)—pharmacokinetic time points (above) plus Day 14

6.3. Results

As depicted in FIGS. 3A and 3B, plasma ceramide levels and plasma sphingomyelin levels, respectively, were determined at several time points. Plasma ceramide levels showed a dose-dependent rise by 6 hrs and peaked at 18-72 hrs. Plasma sphingomyelin levels were normal at baseline and showed no consistent trend over time. In patient no. 12112 who received the highest dose (1 mg/kg), the plasma sphingomyelin level rose post-dose and peaked at 72 hours.

FIG. 4 depicts total bilirubin levels determined over several time points during the protocol. Total bilirubin showed a dose-related rise by 24 hrs and peaked at 48-60 hrs. The highest total bilirubin was 4.7 mg/dL in patient no. 12112 who received the highest dose (1 mg/kg). There were proportional increases in direct and indirect bilirubin. No increases were seen in ALT, AST, or alkaline phosphatase. There was a mild increase in GGT through 72 hrs (not shown) in two patients who received the highest (1 mg/kg, patient no. 12112) and lowest (0.03 mg/kg, patient no. 10503) doses. Hemoglobin and hematocrit levels were stable through the protocol, indicating that hemolysis was not responsible for elevated bilirubin levels.

FIGS. 5A-5G depict the levels of acute phase response (inflammation) markers, CRP/hs-CRP, % neutrophils, fibrinogen, ferritin, IL-8, IL-6, and calcitonin, respectively, determined at several time points for several patients. CRP/hs-CRP showed a transient dose-related rise by 24 hrs, peaked at 48-72 hrs, and returned to normal by Day 14. Other acute phase reactants also showed increases (% neutrophils, fibrinogen, ferritin, PT and PTT) and decreases (iron, albumin). Certain inflammatory biomarkers, e.g., the cytokines IL-6 and IL-8, and calcitonin, also showed substantial elevations that were dose dependent and peaked 48 hours post-infusion. Among these inflammatory mediators, the greatest changes in descending order occurred in IL 8 (peak 33.8× upper limit of normal), calcitonin (peak 33.4×upper limit of normal), CRP (peak 9.8×upper limit of normal), and ferritin (3.9×upper limit of normal). There was no trend in platelet count or the level of fibrin-split products (not shown). The rises in laboratory acute phase reactants correlated with the constitutional clinical symptoms of fever, nausea, vomiting, headache, pain, and myalgias in some patients.

FIG. 6 is a chart of treatment emergent adverse events for four patients each on a different dose of rhASM, which events were considered to be related (possibly, probably, or definitely) to treatment. As set forth in the chart, patient no. 11509, who was given a dose of 0.3 mg/kg rhASM, exhibited moderately severe adverse events starting on day 2.

With regard to related adverse events reported in the protocol, there were no significant cardiovascular changes by telemetry, ECG, echocardiogram, or biomarkers (BNP, cardiac troponin-1, CPK-MB) or adrenal hormone dysfunction. One patient (no. 12112, 1.0 mg/kg cohort) had an elevated cortisol level in the morning 24 hours post-dose, which most likely represented a normal physiologic stress response to several ongoing moderate related adverse events. Further, four of six patients receiving ≥0.3 mg/kg rhASM experienced a total of 19 clinical and laboratory related adverse events assessed as drug-related. The intensity of related adverse events ranged from mild to severe, but most were moderate and did not require any intervention. They included fever (n=2), pain [myalgia; abdominal, leg, and hip pain] (n=2), nausea (n=2), scleral icterus and urine urobilinogen (n=1), fatigue (n=1), vomiting (n=1), lymphocytic infiltrate/hepatocellular degeneration on liver biopsy (n=1), acute phase reaction (n=4), elevated bilirubin (n=2), and increased fibrin D-dimer (n=1). The onset of clinical symptoms began 12 hours post-infusion and resolved by 72 hrs, except for hip pain in one patient that began after 72 hours. At day 14, a liver biopsy in one patient (0.6 mg/kg rhASM, patient no. 12313) showed two new foci of lymphocytic infiltrates: one was tiny (0.1 mm diameter), and the other was moderate (0.5 mm diameter) and which was associated with hepatocellular degeneration. This protocol was stopped when the first patient in cohort 5 (1 mg/kg rhASM, patient no. 12112) experienced a dose-limiting toxicity of hyperbilirubinemia (peak 4.7 mg/dL).

The results of this showed an unexpected and delayed onset of dose-related clinical and laboratory adverse events in humans suffering from ASMD at doses of rhASM of 0.3 mg/kg and higher. Further, two major safety laboratory observations were made in view of the results of this protocol. One regarding hyperbilirubinemia, in which a proportionate to dose rise in direct and indirect bilirubin was observed with no consistent markers of liver damage (AST, ALT, AP) or evidence of hemolysis (hemoglobin and hematocrit). Two patients had mildly elevated GGT at 48-72 hours, and one patient had two new liver foci of lymphocytic infiltrates, one of which was associated with hepatocellular degeneration.

The other observation concerned the acute phase response, i.e., inflammation. The results showed an increase in CRP/hs-CRP, % neutrophils, ferritin, IL-6, IL-8, calcitonion, fibrinogen, PT, PTT, and a decrease in iron and albumin in response to increasing dosages of rhASM. The constitutional clinical symptoms of fever, nausea, vomiting, pain, and myalgia were most likely related to the acute phase response. The results showed no evidence of cytokine release syndrome associated with cardiovascular changes, and no evidence of adrenal hormone dysfunction.

6.4. Conclusions

The above-described protocol is the first experience with enzyme replacement therapy in adult human patients with ASMD. At bioactive doses in humans, rhASM did not cause cytokine release syndrome associated with cardiovascular changes, or cause adrenal hormone dysfunction. The major safety observations were dose-related hyperbilirubinemia and acute phase response. Both adverse events are likely related to the breakdown of sphingomyelin into ceramide and phosphylcholine, but the exact molecular mechanisms are not fully understood. Several safety biomarkers were identified, including bilirubin, ceramide, hsCRP, IL-8, IL-6, calcitonin, and ferritin. Further, based on the hyperbilirubinemia findings, the maximum tolerated starting dose of rhASM was 0.6 mg/kg.

Moreover, the fact that the onset of adverse events with clinical symptoms in patients was observed at a dose as low as 0.3 mg/kg was surprising, given that the NOAEL ("no observed adverse effect level") in the ASMKO mouse was 0.3 mg/kg. Notably, clinical symptoms of toxicity in the ASMKO mice was not observed until doses greater than or equal to 10 mg/kg were used.

7. EXAMPLE 2

Repeat Dose Intravenous Injection Toxicity Protocol Following Debulking Phase in Acid Sphingomyelinease Knock-Out Mice This example describes the investigation of the potential toxicity of repeated intravenous administration of recombinant human acid sphingomyelinase (rhASM) following a debulking phase in acid sphingomyelinase knockout (ASMKO) mice. Having established that toxic side effects begin to be observed at initial doses of 10 mg/kg of rhASM in ASMKO mice, the following investigation was designed to determine if the administration of escalating doses of recombinant human acid sphingomyelinase (rhASM) in ASMKO mice would debulk enough of the accumulated sphingomyelin so that a higher dose of rhASM could be administered to the ASMKO mice to target sites of pathology, such as the lung and brain, with minimal or no observable toxicity.

JK ASMKO mice were administered 3 mg/kg rhASM on study days (SD) 1, 3, 5, 7 (Debulking Phase). Beginning on SD 9 and continuing every other week for 13 weeks (7 doses) mice received treatment doses of 3, 10, or 30 mg/kg rhASM (Treatment Phase).

rhASM was intravenously administered via a bolus injection in a lateral tail vein to male and female ASMKO mice. Groups 1-3 received 3 mg/kg rhASM during the Debulking Phase (SD 1, 3, 5 and 7). Groups 1, 2, and 3 received 3, 10 and 30 mg/kg rhASM, respectively, during the Treatment Phase (SD 9, 23, 37, 51, 65, 79, and 93). One subset of mice in each group (the first 2 mice/sex in Group 1 and the first 4 mice/sex in Groups 2-3) were bled pre-study as well as 5 minutes and 4 hours following Treatment Phase Doses 1, 4, and 7 for analysis of toxicokinetics (TK) (5 minutes) and ceramide levels (4 hours). The other subset of mice in each group (the last 2 mice/sex in Group 1 and the last 4 mice/sex in Groups 2-3) were bled pre-study as well as 4 and 24 hours following Treatment Phase Doses 1, 4, and 7 for analysis of rodent multi-analyte profiles (4 hours) and acute phase protein/liver function test levels (24 hours). See the Study Design in Table 2, infra.

Due to the likelihood of anaphylactic responses beginning with the first Treatment Phase dose and each dose thereafter, each mouse was observed closely for signs of anaphylaxis (e.g. restlessness, chewing, rubbing face, urticaria, edema, lethargy, and scruffy coat) following test article administration. Mice received diphenhydramine (DPH) beginning prior to the first dose of the Treatment Phase and each dose thereafter.

DPH at a concentration of 5 mg/mL was prepared by diluting a 50 mg/mL commercially-available stock solution with sterile 0.9% saline. DPH was administered intraperitoneally (IP) at a dose of 20 mg/kg (4 mL/kg) based on the most recent body weight, 10-20 minutes prior to dosing rhASM to prevent possible anaphylactic reactions. If any animal demonstrated a hypersensitivity reaction post-test article administration, despite DPH pre-treatment, a second dose of DPH was administered IP at 10 mg/kg (2 mL/kg).

All mice were euthanized via CO2 asphyxiation on SD 100. Following euthanasia blood were collected for clinical pathology and immunogenicity analysis via a cardiac puncture. A necropsy was performed on all mice following blood collection. All tissues were preserved in 10% neutral buffered formalin (NBF) followed by histopathological analysis. A piece of the liver, spleen, kidney, and lung were preserved in 2% glutaraldehyde/2% paraformaldehyde for analysis of the sphingomyelin load. A piece of the liver, spleen, kidney, and lung were also collected and stored at $\leq-70°$ C. for possible future analysis.

Following necropsy all remaining tissues including the carcass were placed in 10% NBF.

TABLE 2

STUDY DESIGN:

| Dose Identification | No. of Animals | | Debulking Phase | Dose Level of rhASM Treatment | Dose Concentration of Treatment (mg/ml) | Dose Volume of Treatment (mL/kg) |
|---|---|---|---|---|---|---|
| | Male | Female | | | | |
| 1—rhASM* | 4 | 4 | All mice were administered 3 mg/kg rhASM on Study Days 1, 3, 5, and 7 | 3 mg/kg beginning on Study Day 9 and every | 0.39 | 7.7 |

TABLE 2-continued

STUDY DESIGN:

| Dose Identification | No. of Animals | | Debulking Phase | Dose Level of rhASM Treatment | Dose Concentration of Treatment (mg/ml) | Dose Volume of Treatment (mL/kg) |
|---|---|---|---|---|---|---|
| | Male | Female | | | | |
| 2—rhASM* | 8 | 8 | Doses were administered at a concentration of 0.39 mg/mL at a volume of 7.7 mL/kg | other week thereafter for 13 weeks 10 mg/kg beginning on Study Day 9 and every other week thereafter for 13 weeks | 1.3 | |
| 3—rhASM* | 8 | 8 | | 30 mg/kg beginning on Study Day 9 and every other week thereafter for 13 weeks | 3.9 | |

*Diphenhydramine will be administered to all mice prior to the 1ˢᵗ Treatment Phase dose and each dose thereafter.

In Life Observations:

The first day of the study was considered SD1 (the first day of dosing). Animal body weights were taken once weekly during the course of the study beginning on SD-1 and were taken on the Monday of each week thereafter. Cageside observations were made once daily Monday through Friday. Any abnormalities and observations of normal were recorded. Post-dose clinical observations/scoring were made immediately prior to, 10-20, and 50-70 minutes following each dose administration. Any abnormalities and observations of normal were recorded. The attending veterinarian and/or the study director was consulted in the event of an adverse reaction and appropriate actions were taken based on their recommendations.

Euthanasia:

If there was an adverse reaction that affected the health and well being of an animal, then the animal was euthanized via CO2 asphyxiation, opened via the thoracic, abdominal, and cranial cavities and placed in 10% neutral buffered formalin (NBF) for possible future analysis. If an animal was found dead, the entire carcass was preserved in 10% NBF for possible future analysis. At the end of the study all surviving animals were euthanized by CO2 asphyxiation.

Sample Collection:

Dose Analysis:

Approximately five-hundred microliters (500 µL) of test article from all dose levels was collected within 1-10 minutes following formulation on each day of dosing and stored on dry ice until transfer to a freezer set to maintain a temperature of ≤−70° C. Dose analysis samples were transferred on SD 1, 3, 5, 7, 9, 23, 37, 51, 65, 79, and 93 and were stored at ≤−70° C. until analysis. Dose analysis samples were measured via the A280 assay.

Blood Collection:

For the collection of blood for analysis of TK, rodent multi-analyte profiles, and acute phase protein/liver function test levels mice were anesthetized with a mixture of isoflurane and oxygen. Blood collections occurred on SD −1, 9, 51 and 93 (pre-study and the 1st, 4th, and 7th treatment phase doses, respectively) according to the Blood Collection Tables (see Tables 4 and 5, infra) and the following text.

rhASM Toxicokinetics:

The first 2 mice/sex in Group 1 and the first 4 mice/sex in Groups 2-3 had a blood sample taken for analysis of peak rhASM levels pre-study (SD −1), and 5 minutes following the 1st, 4th, and 7th Treatment Phase doses. Blood from all animals was collected from the retro-orbital plexus of unconscious mice. Approximately 60 µL of whole blood was collected into hematocrit tubes and allowed to clot at room temperature for at least 1 minute. Serum were prepared from these samples by centrifugation for 5 minutes at 10,000 revolutions per minute (RPM). Following centrifugation the serum was collected and stored on dry ice until transfer to a freezer set to maintain a temperature of ≤−70° C. Once transferred, all samples were stored at ≤−70° C. until analysis. TK samples were transferred on SD 1, 9, 51, and 93. TK samples were measured by an enzyme linked immunosorbent assay (ELISA).

Analysis of Ceramide Levels:

The first 2 mice/sex in Group 1 and the first 4 mice/sex in Groups 2-3 had a blood sample taken for analysis of ceramide levels pre-study (SD −1), and 4 hours following the 1st, 4th, and 7th Treatment Phase doses. Blood from these animals was collected from the retro-orbital plexus of unconscious mice. Approximately 240 µL of whole blood was collected into potassium EDTA tubes and placed on a Nutator rocker for up to 30 minutes to prevent the formation of a clot. Plasma was prepared from these samples by centrifugation for 5 minutes at 10,000 RPM. Following centrifugation the plasma was collected and stored on dry ice until transfer to a freezer set to maintain a temperature of ≤−70° C. Once transferred, all samples were stored at ≤−70° C. until analysis by a Mass Spectrometry Group. Ceramide samples were transferred no later than SD 94. Ceramide samples were measured by mass spectrometry.

Analysis of Rodent Multi-Analyte Profiles (MAP):

The last 2 mice/sex in Group 1 and the last 4 mice/sex in Groups 2-3 had a blood sample taken for analysis of rodent multi-analyte profiles pre-study (SD −1), and 4 hours following the 1st. 4th, and 7th Treatment Phase doses. Blood from these animals was collected from the retro-orbital plexus in unconscious mice. Approximately 150 μL of whole blood was collected into serum separator tubes and allowed to clot for at least 30 minutes. Serum was prepared from these samples by centrifugation for 5 minutes at 10,000 RPM. Following centrifugation the serum was collected and stored on dry ice until transfer to a freezer set to maintain a temperature of ≤−70° C. Once transferred, all samples were stored at ≤−70° C. until shipment on no later than SD 94 for analysis of rodent multi-analyte profiles. Samples were shipped to Rules Based Medicine on dry ice. The Rodent Multi-Analyte Profiles Table (see Table 3, infra) lists the analytes that were measured.

TABLE 3

Rodent Multi-Analyte Profiles: Analytes to be Tested

| | | |
|---|---|---|
| Apolipoprotein A1 | Interleukin-2 | MIP-3 beta |
| C-Reactive Protein | Interleukin-3 | MMP-9 |
| CD40 | Interleukin-4 | MCP-1 |
| CD40 Ligand | Interleukin-5 | MCP-3 |
| Endothelin-1 | Interleukin-6 | MCP-5 |
| Eotaxin | Interleukin-7 | Mycloperoxidase |
| Epidermal Growth Factor | Interleukin-10 | Myoglobin |
| Factor VII | Interleukin-11 | Oncostatin M |
| Fibrinogen | Interleukin-12p70 | RANTES |
| FGF-basic | Interleukin-17 | Serum Amyloid P |
| FGF-9 | KC/GRO alpha | SGOT |
| GCP-2 | Leukemia Inhibitory Factor | Stem Cell Factor |
| GM-CST | Lymphotactin | Thrombopoietin |

TABLE 3-continued

Rodent Multi-Analyte Profiles: Analytes to be Tested

| | | |
|---|---|---|
| GST-alpha | M-CSF | TIMP 1 |
| Haptoglobin | MDC | Tissue Factor |
| Immunoglobulin A | MIP-1 alpha | Tumor Necrosis Factor-alpha |
| Inducible Protein-10 | MIP-1 beta | VCAM-1 |
| Interferon-gamma | MIP-1 gamma | VEGF |
| Interleukin-1 alpha | MIP-2 | von Willebrand Factor |
| Interleukin-1 beta | | |

Analysis of Acute Phase Protein/Liver Function Test Levels:

The last 2 mice/sex in Group 1 and the last 4 mice/sex in Groups 2-3 had a blood sample taken for analysis of acute phase protein (serum amyloid-A and serum amyloid-P) and liver function (bilirubin and alanine aminotransferase (ALT)) levels pre-study (SD −1), and 24 hours following the 1st, 4th, and 7th Treatment Phase doses. Blood from these animals was collected from the retro-orbital plexus in unconscious mice. Approximately 150 μL of whole blood was collected into serum separator tubes and allowed to clot for at least 30 minutes. Serum was prepared from these samples by centrifugation for 5 minutes at 10,000 RPM. Following centrifugation the serum was collected and stored on dry ice until transfer to a freezer set to maintain a temperature of ≤−70° C. Once transferred, all samples were stored at ≤−70° C. until shipment no later than SD 94 for acute phase protein/liver function test analysis. Samples were shipped to Analytics on dry ice.

TABLE 4

Pre-Study (SD-1) Blood Collection Table

| Group | Animal # | Sex | TK Pre-Bleed (60 μL) | Rodent Map Pre-Bleed (150 μL) | Ceramide Pre-Bleed (240 μL) | APP/Liver Function Pre-Bleed (150 μL) |
|---|---|---|---|---|---|---|
| 1 | 1, 2 | M | X | | X | |
|   | 5, 6 | F | X | | X | |
|   | 3, 4 | M | | X | | X |
|   | 7, 8 | F | | X | | X |
| 2 | 9, 10, 11, 12 | M | X | | X | |
|   | 17, 18, 19, 20 | F | X | | X | |
|   | 13, 14, 15, 16 | M | | X | | X |
|   | 21, 22, 23, 24 | F | | X | | X |
| 3 | 25, 26, 27, 28 | M | X | | X | |
|   | 33, 34, 35, 36 | F | X | | X | |
|   | 29, 30, 31, 32 | M | | X | | X |
|   | 37, 38, 39, 40 | F | | X | | X |

TABLE 5

SD 9, 51, and 93 Blood Collection Table

| Group | Animal # | Sex | TK Bleed (60 μL) 5 Minutes Post-Dose | Rodent Map Bleed (150 μL) 4 Hours Post-Dose | Ceramide Bleed (240 μL) 4 Hours Post-Dose | APP/Liver Function Bleed (150 μL) 24 Hours Post-Dose |
|---|---|---|---|---|---|---|
| 1 | 1, 2 | M | X | | X | |
|   | 5, 6 | F | X | | X | |
|   | 3, 4 | M | | X | | X |
|   | 7, 8 | F | | X | | X |
| 2 | 9, 10, 11, 12 | M | X | | X | |
|   | 17, 18, 19, 20 | F | X | | X | |
|   | 13, 11, 15, 16 | M | | X | | X |
|   | 21, 22, 23, 24 | F | | X | | X |

TABLE 5-continued

SD 9, 51, and 93 Blood Collection Table

| Group | Animal # | Sex | TK Bleed (60 µL) 5 Minutes Post-Dose | Rodent Map Bleed (150 µL) 4 Hours Post-Dose | Ceramide Bleed (240 µL) 4 Hours Post-Dose | APP/Liver Function Bleed (150 µL) 24 Hours Post-Dose |
|---|---|---|---|---|---|---|
| 3 | 25, 26, 27, 23 | M | X | | X | |
| | 33, 34, 35, 36 | F | X | | X | |
| | 29, 30, 31, 32 | M | | X | | X |

Necropsy

Terminal Blood Collection for Analysis of Clinical Pathology and Immunogenicity:

Following euthanasia, all animals had a cardiac puncture performed for the collection of whole blood (approximately ≥500 µL) from all main study animals for clinical pathology and immunogenicity analysis. Approximately 150 µL of the whole blood was placed in potassium EDTA tubes, and gently inverted for analysis of hematology parameters. Following the gentle inversion all samples were stored at room temperature rocking on a Nutator rocker until the samples were stored at 2-10° C. until analysis. The remaining blood (from the cardiac stick following removal of 150 µL for hematology analysis) was placed in a serum separator tube, allowed to clot at room temperature for at least 30 minutes, spun in a centrifuge for 5 minutes at 10,000 RPM, and the serum will be collected. Approximately 30 µL of serum was placed in an eppendorf tube for immunogenicity analysis while the remaining serum was placed in an eppendorf tube for clinical chemistry analysis. The immunogenicity samples were stored on dry ice until they were stored in a freezer set to maintain a temperature of ≤−70° C. Immunogenicity samples were measured by an ELISA. Clinical chemistry samples were placed on dry ice until all samples were stored at ≤−20° C. until analysis. The Hematology and Clinical Chemistry Analyte Table (see Table 6, infra) lists the analytes that were measured.

TABLE 6

Hematology and Clinical Chemistry Analyte Table:

| Hematology Parameters | Clinical Chemistry Parameters |
|---|---|
| Leukocyte count (total and absolute differential) | alkaline phosphatase |
| erythrocyte count | total bilirubin (with direct bilirubin if total bilirubin exceeds 1 mg/dL) |
| Hemoglobin | aspartate aminotransferase |
| Hematocrit | alanine aminotransferase |
| mean corpuscular temoglobin | gamma glutamyl transferase |
| mean corpuscular volume | urea nitrogen |
| mean corpuscular hemoglobin concentration (calculated) | Creatinine |
| Absolute reticulocytes | total protein |
| Platelet count | Albumin |
| blood cell morphology | globulin and A/G (albumin/globulin) ratio (calculated) |
| blood smear | Glucose |
| | total cholesterol |
| | Triglycerides |
| | Electrolytes (sodium, potassium, chloride) |
| | Calcium |
| | Phosphorus |

Results from the analysis of hematology and clinical chemistry analyses from all animals was interpreted by a board certified pathologist.

Tissue Collection:

Following euthanasia on SD 100, all animals were subjected to necropsy for tissue collection. The necropsy included an examination of the external features of the carcass, external body orifices, the abdominal and thoracic cavities, organs, and tissues. Gross findings were recorded. The Tissue Collection Table (see Table 7, infra) lists the tissues that were collected in 10% NBF. Gross lesions were also collected and stored in 10% NBF. The remaining carcass were preserved in 10% NBF.

TABLE 7

Tissue Collection Table

| Tissue | Tissue |
|---|---|
| adrenal (2) | Pancreas |
| Aorta | pituitary gland |
| Brain | Prostate |
| Cecum | Rectum |
| Colon | salivary gland [mandibular (2)] |
| Duodenum | seminal vesicle (2) |
| epididymus (2) | sciatic nerve |
| Esophagus | skeletal muscle (quadriceps) |
| eye with optic nerve (2) | Skin |
| femur with bone marrow (articular surface of the distal end) | spinal cord (cervical, thoracic and lumbar) |
| gall bladder | Spleen |
| Heart | sternum with bone marrow |
| Ileum | Stomach |
| Jejunum | testis (2) |
| kidney (2) | Thymus |
| Liver | thyroid (2) with parathyroid |
| lung with mainstem bronchi | Tongue |
| lymph node (mandibular) | Trachea |
| lymph node (mesentric) | urinary bladder |
| mammary gland (females) | uteras with cervix |
| ovary (2) | gross lesions |

Bolded samples will be weighed

Organ Weights:

At the time of necropsy, the above bolded organs were weighed: paired organs were weighed together. Weights were recorded on the organ weight form. Organ-to-body weight percentages and organ-to-brain weight ratios were calculated based on the body weights taken prior to necropsy.

Histopathology:

Samples from all animals as well as gross lesions from any animal on study were transferred to histology. Preserved tissues listed above from each animal were embedded in paraffin. All tissues were sectioned, stained with hematoxylin and eosin, and were examined microscopically. All tissue sections were examined microscopically for the evaluation of histological changes by a board certified pathologist.

Samples of the liver, spleen, kidney, and lung from all animals were collected and fixed in 2% glutaraldehyde/2% paraformaldehyde for analysis of sphingomyelin load. These tissues were post-fixed in potassium dichromate/osmium tetroxide and embedded in epon. One-micron sections were stained with tannic acid and toluidine blue for light microscopic examination. The sphingomyelin load in each sample was quantitated by computer morphometry with MetaMorph software by a board certified pathologist.

Samples of the liver, spleen, kidney, and lung from all animals were collected, frozen in liquid nitrogen, and stored frozen at ≤−70° C. for possible future analysis.

Sample Analysis:

Dose analysis was measured via A280 analysis and toxicokinetic, and immunogenicity samples were be analyzed by ELISA.

Ceramide analysis was measured via mass spectrometry.

Hematology and clinical pathology samples were measured using the Sysmex XTV 2000 IV Hematology Analyzer and the Radnox Daytona Clinical Chemistry Analyzer, respectively.

Tissue samples were processed and histopathological analysis was interpreted by a board certified pathologist according to SOPs. Results from the clinical pathology analysis was interpreted by a board certified pathologist according to SOPs.

8. EXAMPLE 3

Escalating Dose of Recombinant Human Acid Sphingomyelinase (rhASM) Enzyme Replacement Therapy

8.1. Introduction

The protocol described below utilizes within-patient dose escalation as an option for achieving higher repeat doses of rhASM. The safety, efficacy and pharmacokinetics (PK) of rhASM infusions at doses of 0.3, 0.6, and 1.0 mg/kg administered every 2 weeks (q2w) for 40 weeks, and long term safety and efficacy of rhASM infusions are evaluated.

8.2. Materials and Methods

8.2.1. Protocol Design

The 12 NP-type B patients to be treated are of either gender. Patients will receive at least 1 dose of 0.1 mg/kg rhASM initially. Patients that tolerate the 0.1 mg/kg rhASM infusion are then administered escalating doses of 0.3 mg/kg. 0.6 mg/kg, and 1 mg/kg every 2 weeks, as tolerated. Patients who tolerate 1.0 mg/kg are then stratified by spleen volume (<12 times or ≥12 times multiples of normal) and randomized to receive one of 2 target doses: 1.0 mg/kg rhASM or 3.0 mg/kg; patients randomized to the 3.0 mg/kg group will escalate to 2.0 mg/kg and then 3.0 mg/kg, as tolerated. Patients who do not tolerate the 0.1 mg/kg dose of rhASM are replaced. Patients who cannot tolerate escalation at higher doses will remain at their maximum tolerated dose for the duration of the 26 week maintenance dose period.

All patients will have doses escalated from 0.1 mg/kg to their target dose. Dosage adjustments during the escalation period will occur at every 2 week intervals until the target dose is reached (if tolerated). Following the initial infusion (0.1 mg/kg rhASM) as well as subsequent doses, patient outcomes. i.e., adverse event (AE) occurrence/severity and serum bilirubin, hsCRP, and other acute phase response proteins, and ceramide, will be reviewed. The following criteria will determine the next dose to be administered during the dose escalation period:

1. Total bilirubin value ≤2.0 mg/dL or mild AE→escalate to next dose (if applicable)
2. Total bilirubin value=2.1-3.0 mg/dL or moderate AE→no dosage escalation; repeat current dose,
3. Total bilirubin value >3.0 mg/dL) or severe AE→decrease dose to previously administered/tolerated.

Any serious adverse event (SAE) judged to be related to rhASM, a bilirubin value that does not decrease to <2.0 mg/dL prior to the next scheduled dose or any AE that raises concern regarding the safety of rhASM at the administered dose may be considered a dose-limiting-toxicity (DLT). If a patient experiences a DLT, subsequent doses for the patient should be temporarily halted. Patients may be re-challenged to receive the dose that resulted in a DLT and if tolerated, treatment will proceed as originally planned.

If a patient cannot tolerate 2 doses of 0.1 mg/kg (i.e. initial infusion and one re-challenge dose) they will not be treated with escalating doses and will be discontinued and replaced in the study. Patients who tolerate the 0.3 mg/kg dose will receive the initial rhASM infusion (0.1 mg/kg) and, after 2 weeks. 0.3 mg/kg rhASM (provided the dose escalation criteria are met following the 0.1 mg/kg dose). Subsequent rhASM doses will be administered during the dose escalation period q2w for a maximum of 18 weeks. If a patient successfully escalates to 0.3 mg/kg and subsequently meets criteria #2 or #3 (above), the patient may be re challenged twice. If re-challenge is unsuccessful (i.e., target dose cannot be reached), the patient will continue on a rhASM dose of 0.1 mg/kg for the remainder of the 40-week treatment period.

Patients to be treated with the 0.6 mg/kg dose regimen will receive the initial rhASM infusion (0.1 mg/kg), followed by 1 dose of 0.3 mg/kg rhASM, followed by 0.6 mg/kg rhASM q2w for the remainder of the 40-week treatment period (provided the previous rhASM infusions of 0.1 mg/kg and 0.3 mg/kg are well tolerated). Patients to be treated with the 1.0 mg/kg regimen will receive the initial rhASM infusion (0.1 mg/kg), followed by 1 dose of 0.3 mg/kg rhASM, followed by 1 dose of 0.6 mg/kg rhASM, followed by 1.0 mg/kg rhASM q2w for the remainder of the 40-week treatment period (provided the previous rhASM infusions of 0.1 mg/kg, 0.3 mg/kg, and 0.6 mg/kg are well tolerated). If a patient successfully escalates from 0.3 to 0.6 mg/kg or from 0.6 to 1.0 mg/kg and subsequently meets criteria #2 or #3 (above), the patient may be re challenged twice. If re-challenge is unsuccessful (i.e., target dose cannot be reached), the patient will continue on the lower tolerated dose for the remainder of the 40-week treatment period.

Following the 40-week treatment phase, patients may be allowed to continue their treatment at their maintenance dose level.

8.2.2. Patients

Each patient should meet the following inclusion criteria to be treated in accordance with these regimens:

1. Documented ASM deficiency consistent with Niemann-Pick (N-P) disease;
2. Diffusing capacity (DLCO)>20% and ≤80% of the predicted normal value;
3. Spleen volume ≥8 times normal (≥1.6% of body weight);
4. Female patients of childbearing potential must have a serum pregnancy test negative for β-hCG, and agree to use a medically acceptable method of birth control for the duration of the protocol.

8.2.3. Treatment

Patients will receive a single 0.1 mg/kg rhASM IV over an approximate 35 minute time period. Administration guidelines are summarized in Table 8, below. Patients that tolerate the initial 0.1 mg/kg rhASM infusion will be dose escalated to a target treatment dose (rhASM 0.3, 0.6 or 1.0 mg/kg). All patients will have doses escalated from 0.1 mg/kg to their target dose. Dosage adjustments during the escalation period will occur at every 2 week intervals until the target dose is reached.

TABLE 8

Administration of rhASM

| Target Dose (mg/kg) | Approximate Infusion Rate (mL/hr) | Approximate Infusion Rate (mg/kg/hr) | Length of Administration (approx. time in minutes) |
|---|---|---|---|
| 0.1 | Step 1: 20 mL/hr over 20 min (+/−5 min), if no IAR<br>Step 2: 60 mL/hr for the remainder of the infusion if no IAR | Step 1: 0.1 mg/kg/hr over 20 min (+/−5 min), if no IAR<br>Step 2: 0.3 mg/kg/hr for the remainder of the infusion if no IAR | 35 |
| 0.3 | Step 1: 17 mL/hr over 20 min: (+/−5 min), if no IAR<br>Step 2: 50 mL/hr over 20 mM (+/−5 min), if no IAR<br>Step 3: 100 mL/hr for the remainder of the infusion if no IAR | Step 1: 0.1 mg/kg/hr over 20 min: (+/−5 mM), if no IAR<br>Step 2: 0.3 mg/kg/hr over 20 mM (+/−5 mM), if no IAR<br>Step 3: 0.6 mg/kg/hr for the remainder of the infusion if no IAR | 60 |
| 0.6 | Step 1: 17 mL/hr over 20 min (+/−5 min), if no IAR<br>Step 2: 50 mL/hr over 20 min (+/−5 min), if no IAR<br>Step 3: 100 mL/hr over 20 min (+/−5 min), if no IAR<br>Step 4: 167 mL/hr for the remainder of the infusion if no IAR | Step 1: 0.1 mg/kg/hr over 20 min (+/−5 min), if no IAR<br>Step 2: 0.3 mg/kg/hr over 20 min (+/−5 min), if no IAR<br>Step 3: 0.6 mg/kg/hr over 20 min (+/−5 min), if no IAR<br>Step 4: 1.0 mg/kg/hr for the remainder of the Infusion if no IAR | 80 |
| 1.0 | Step 1: 10 mL/hr over 20 min (+/−5 min), if no IAR<br>Step 2: 30 mL/hr over 20 min (+/−5 min), if no IAR<br>Step 3: 60 mL/hr over 20 min (+/−5 min), if no IAR<br>Step 4: 100 mL/hr for the remainder of the infusion if no IAR | Step 1: 0.1 mg/kg/hr over 20 min (+/−5 min), if no IAR<br>Step 2: 0.3 mg/kg/hr over 20 min (+/−5 min), if no IAR<br>Step 3: 0.6 mg/kg/hr over 20 min (+/−5 min), if no IAR<br>Step 4: 1.0 mg/kg/hr for the remainder of the infusion if no IAR | 100 |

Each patient's degree of splenomegaly at baseline can be recorded in multiples of normal (x normal) as an indicator of disease severity. Normal spleen volume is equal to 0.2% of body weight.

At each visit, patients should be evaluated for new or ongoing adverse events (AEs).

Clinical endpoints can be measured as the % change from baseline to Week 26 of the maintenance dose period. The primary efficacy endpoint is a decrease in spleen volume as measured by MRI. Secondary efficacy endpoints include a decrease in liver sphingomyelin level; an increase in exercise capacity as determined by % predicted maximum workload by cycle ergometry; increased pulmonary function as a % predicted DLco; increased lung clearance which can be determined by bronchial alveolar lavage (BAL) cell count and profile, sphingomyelin, ceramide, cytokine and chitotriosidase levels. Tertiary efficacy endpoints can include a decrease in liver volume as measured by MRI; increased pulmonary function which can be determined by % predicted FVC, FEV1, TLC; improved lung appearance determined by high resolution CT scan, chest X-ray; improved lipid profile as determined by HDL, LDL, total cholesterol, triglyceride levels, and total cholesterol:HDL cholesterol ratio; improved platelet count; hemoglobin; decreased sphingomyelin levels in skin, plasma, DBS; and improvement in other biomarkers such as CCL18, ACE.

9. EXAMPLE 4

Escalating Dose of Recombinant Human Acid Sphingomyelinase (rhASM) Enzyme Replacement Therapy

9.1. Introduction

The protocol described below utilizes a repeat-dose, dose comparison to evaluate the safety, efficacy and pharmacokinetics of recombinant human acid sphingomyelinase (rhASM) in adult patients with ASMD. The objectives of the protocol include: (i) the evaluation of the safety of dose escalation of rhASM; (ii) the evaluation of the safety, efficacy and pharmacokinetics of the maximum tolerated or randomized dose of rhASM administered intravenously every 2 weeks for 26 weeks; and (iii) the evaluation of the long-term safety and efficacy of rhASM infusions administered intravenously every 2 weeks from week 26 until protocol completion (at least 182 weeks in duration).

9.2. Materials and Methods

9.2.1. Patients

Each patient should meet the following inclusion criteria to be treated in accordance with these regimens:

1. Documented acid sphingomyelinase (ASM) deficiency consistent with Niemann-Pick disease (NPD).

2. Two or more characteristic clinical features, including thrombocytopenia, anemia, neutropenia, hepatomegaly, splenomegaly, and pulmonary disease consistent with non-neuronopathic NPD.

3. Diffusing capacity of carbon monoxide ($DL_{CO}$)>20% and ≤80% of the predicted normal value;

4. Spleen volume ≥8 multiples of normal (MN) (i.e., ≥1.6% of body weight). A partial splenectomy can be permitted if performed ≥1 year from Screening/Baseline and residual spleen volume is ≥8 MN.

5. Female patients of childbearing potential must have a negative serum pregnancy test for β-human chorionic gonadotropin (β-HCG) and agree to use a medically accepted method of contraception for the duration of the protocol.

9.2.2. PROTOCOL DESIGN

Patients who can tolerate rhASM at 0.1 mg/kg can be enrolled in the protocol. For each patient, protocol participation can consist of 3 periods:

1. Screening/Baseline (−60 to −1 days).
2. Primary Treatment Period (approximately 32 to 46 weeks). Dose Escalation (DE) Phase (Primary DE—approximately 6 to 16 weeks).
   Upon safely escalating from 0.1 to 0.3 to 0.6 to 1.0 mg/kg rhASM, patients can be stratified by spleen volume (<12 and ≥12 MN) and randomized to either continue dosing at 1.0 mg/kg or continue dose escalation through 2.0 and 3.0 mg/kg and then receive 3.0 mg/kg rhASM or the maximum tolerated dose (Secondary DE −4 weeks) for the remainder of the protocol.
   Non-randomized patients can remain at their maximum tolerated dose (<1.0 mg/kg rhASM).
   Dose Maintenance (DM) Phase (26 weeks at maximum tolerated or randomized dose).
3. Long-term Treatment Period (at least 182 weeks at maximum tolerated or randomized dose)

The Screening/Baseline assessments can be completed at least 24 hrs prior to the initial infusion of rhASM. Enrollment into the protocol is contingent upon the patient being able to tolerate 2 doses of rhASM at 0.1 mg/kg. Initially, all eligible patients can receive a single dose of 0.1 mg/kg rhASM on dose escalation (DE) Day 1. Patients who are unable to tolerate this dose are re-challenged 2 weeks later. Patients who cannot tolerate 2 doses of 0.1 mg/kg rhASM (i.e., initial dose and re-challenge dose) are discontinued and replaced, to ensure that approximately 12 patients (who can tolerate rhASM at 0.1 mg/kg) are enrolled.

Doses of rhASM can be escalated every 2 weeks from 0.1 to 0.3 to 0.6 to 1.0 mg/kg during the Primary DE Phase. During the Primary DE Phase, patients can have rhASM doses safely escalated every 2 weeks from 0.1 to 1.0 mg/kg (as indicated in FIG. 7).

During the Primary and Secondary DE Phases, the following dose escalation criteria can determine the next dose of rhASM to be administered:

1. If total bilirubin (the highest value prior to the next scheduled dose of rhASM and includes the pre infusion blood draw) is <2.0 mg/dL or no/mild related adverse event (AE) →Escalate to next dose.
2. If total bilirubin is >2.0 but <3.0 mg/dL or moderate related AE→Repeat same dose.
   If total bilirubin remains >2.0 mg/dL just prior to next dose→Stop further dosing of patient temporarily (potential dose-limiting toxicity [DLT]).
3. If total bilirubin is ≥3.0 mg/dL or severe related AE→Decrease dose.
   If total bilirubin remains >2.0 mg/dL just prior to next dose→Stop further dosing of patient temporarily (potential DLT).
4. Patients can be re-challenged (at a particular dose level) as many times as needed in the Primary DE Phase only (re-challenge is not permitted in the Secondary DE Phase), before being randomized or staying on their maximum tolerated dose by the end of the 16-week Primary DE Phase.
5. Enrolled patients (i.e., those who can tolerate rhASM at 0.1 mg/kg) can not be replaced if they cannot escalate up to a dose of 1.0 mg/kg and be randomized, or cannot tolerate their target randomization dose (i.e., 1.0 or 3.0 mg/kg rhASM). These patients can continue in the protocol at their maximum tolerated dose.

If an infusion is missed, the patient can receive the same dose as the previous infusion. If the visit window of ±5 days is exceeded, that infusion can not be done and the patient should have his/her next infusion at the scheduled time for that infusion.

For the purpose of this protocol, if any of the following criteria are met, the results can be considered indicative of potential dose limiting toxicity (DLT) for rhASM at a given dose:
   Any serious adverse event (SAE) judged by the physician to be related to rhASM, or
   Total bilirubin remains >2.0 mg/dL just prior to next dose, or
   Any adverse event (AE) that, in the opinion of the physician, raises concern regarding the safety of rhASM at the administered dose.

The severity of a related adverse event will be assessed by a physician. A mild related adverse event is usually transient and may require only minimal treatment or therapeutic intervention. A moderate related adverse event is usually alleviated with additional specific therapeutic intervention. This event interferes with usual activities of daily living, causing discomfort, but poses no significant or permanent risk of harm to the subject. A severe adverse event interrupts usual activities of daily living, or significantly affects clinical status, or may require intensive therapeutic intervention.

All patients who had doses escalated and safely tolerate 1.0 mg/kg rhASM by Week 16 can be stratified by spleen volume (<12 and ≥12 MN) and randomized in a 1:1 ratio to either.
   Continue receiving 1.0 mg/kg rhASM (or maximum tolerated dose) every 2 weeks for 26 weeks or
   Continue dose escalation (DE) through 2.0 and 3.0 mg/kg and then receive 3.0 mg/kg rhASM (or maximum tolerated dose) every 2 weeks for 26 weeks.

During the Secondary DE Phase, patients randomized to the 3.0 mg/kg group can have only 4 weeks to escalate their rhASM dose to 3.0 mg/kg before starting the 26-week DM Phase at 3.0 mg/kg (or maximum tolerated dose; see FIG. 7).

The Primary DE Phase can range from approximately 6 to 16 weeks in duration for each patient. This can depend on individual patient tolerability issues, if any, encountered by the patient during dose escalation of rhASM. During the Primary DE Phase, each patient can have their dose of rhASM escalated every 2 weeks from 0.1 to 1.0 mg/kg (as indicated in FIG. 7).

The Primary DE Phase can be completed when a patient receives and tolerates a dose of 1.0 mg/kg rhASM or reaches Week 16, which ever occurs first. If no criteria leading to a dose re-challenge or a decrease in dose are met, a patient can receive a single infusion of each dose (i.e., a total of 4 infusions of rhASM), resulting in a Primary DE Phase of 6 weeks. However, if criteria leading to dose re-challenge or decrease in dose are met the duration of the Primary DE Phase can be longer than 6 weeks, but will not exceed 16 weeks.

Patients who had doses escalated and safely tolerate 1.0 mg/kg by Week 16 can be assigned to 1 of 2 target dose groups (i.e., 1.0 or 3.0 mg/kg rhASM).

Patients randomized to 3.0 mg/kg rhASM can enter the Secondary DE Phase (see FIG. 7), consisting of 2 infusions: the first infusion (i.e., 2.0 mg/kg) being 2 weeks after the first tolerated dose of 1.0 mg/kg, and the second infusion (i.e., 3.0 mg/kg or maximum tolerated dose) being 4 weeks after the first tolerated dose of 1.0 mg/kg. Therefore the Secondary DE Phase can be completed 4 weeks after the first tolerated dose of 1.0 mg/kg. No re-challenge dose will be allowed. If the patient cannot tolerate the first dose at 2.0 mg/kg, the second rhASM dose can be decreased to the maximum tolerated dose (i.e., 1.0 mg/kg) or temporarily halted in the event of a potential dose limiting toxicity (DLT).

Patients can continue receiving rhASM at the maximum tolerated or randomized dose administered IV every 2 weeks during the 26-week DM Phase of the Primary Treatment Period. This can include both randomized and non-randomized patients.

As indicated in FIG. 7, patients in the 1.0 mg/kg dose group can start the DM Phase at their first dose of 1.0 mg/kg following randomization, whereas patients in the 3.0 mg/kg group can start the DM Phase at their third dose of rhASM following randomization. Subsequent rhASM doses can be administered IV every 2 weeks for 26 weeks in the DM Phase for all randomized patients.

Non-randomized patients can start the DM Phase at their first dose of rhASM 2 weeks after their 16-week DE Phase. These patients can continue on their maximum tolerated dose of rhASM (<1.0 mg/kg) every 2 weeks for a total of 26 weeks.

If a randomized patient experiences a moderate/severe related AE (i.e., an infusion associated reaction (IAR)) during the infusion in the DM Phase, the patient may have the rhASM infusion stopped and restarted (i.e., interrupted) or the infusion rate slowed down. Provided that a potential DLT has not occurred, the patient can continue on this dose of rhASM for the remainder of the DM Phase.

After all Week 26 protocol assessments have been completed, all patients (including non-randomized patients) can enter the Long-Term Treatment period and continue rhASM treatment (at the rhASM dose that was administered during the DM Phase) IV every 2 weeks for at least 182 weeks [3.5 years] in duration or until termination of the protocol. The Long-Term Treatment Period includes the Protocol Completion (or patient withdrawal/discontinuation) visit and a safety follow-up phone call (30 to 37 days after the last dose of rhASM). Individual patient doses of rhASM may be adjusted in the Long-Term Treatment Period based on the results of the Primary Treatment Period analyses. Any required dose escalation can occur as previously described.

9.3. Treatment

Patients will receive intravenous infusions of rhASM at 0.1, 0.3, 0.6 and 1.0 mg/kg every 2 weeks during the Primary DE Phase. Patients randomized to 3.0 mg/kg rhASM will receive 2.0 mg/kg prior to receiving 3.0 mg/kg (or maximum tolerated dose) 2 weeks later during the Secondary DE Phase. During the 26-week DM Phase, patients will be administered 1.0 or 3.0 mg/kg (or maximum tolerated dose) rhASM every 2 weeks following the DE Phase. During the Long-Term Treatment Period, the rhASM dose that was administered during the DM Phase will be administered IV every 2 weeks.

Patients will receive each intravenous infusion of rhASM over a period of approximately 35 to 135 minutes (min) depending on the dose (see Table 9 below). Protocol treatment (rhASM) will be infused using a standard programmable infusion pump and a 0.22 micron, low protein-binding, in-line filter. To calculate the dose in mg/kg, use actual weight for patients with body mass index (BMI)≤30 (weight in kg)/(height in meters); for patients with BMI>30, calculate the weight corresponding to a BMI of 30 using the patient's height.

TABLE 9

Administration of rhASM

| rhASM Dose (mg/kg) | Total Volume of 0.9% Sodium Chloride for Injection, to be mixed (mL) | Approximate Infusion Rate (mL/hr) | Approximate Infusion Rate mg/kg/hr) | Length of Administration (approximate time [min]) |
|---|---|---|---|---|
| 0.1 | 20 | Step 1: 20 mL/hr over 20 min (±5 min), if no IAR<br>Step 2: 60 mL/hr for the remainder of the infusion if no IAR | Step 1: 0.1 mg/kg/hr over 20 min (±5 min), if no IAR<br>Step 2: 0.3 mg/kg/hr for the remainder of the infusion if no IAR | 35 |
| 0.3 | 50 | Step 1: 17 mL/hr over 20 min (±5 min), if no IAR<br>Step 2: 50 mL/hr over 20 min (±5 min), if no IAR<br>Step 3: 100 mL/hr for the remainder of the infusion if no IAR | Step 1: 0.1 mg/kg/hr over 20 min (±5 min), if no IAR<br>Step 2: 0.3 mg/kg/hr over 20 min (±5 min), if no IAR<br>Step 3: 0.6 mg/kg/hr for the remainder of the infusion if no IAR | 60 |
| 0.6 | 100 | Step 1: 17 mL/hr over 20 min (±5 min), if no IAR.<br>Step 2: 50 mL/hr over 20 min (±5 min), if no IAR<br>Step 3: 100 mL/hr over 20 min (±5 min), if no IAR<br>Step 4: 167 mL/hr for the remainder of the infusion if no IAR | Step 1: 0.1 mg/kg/hr over 20 min (±5 min), if no IAR<br>Step 2: 0.3 mg/kg/hr over 20 min (±5 min), if no IAR<br>Step 3: 0.6 mg/kg/hr over 20 min (±5 min), if no IAR<br>Step 4: 1.0 mg/kg/hr for the remainder of the Infusion if no IAR | 80 |
| 1.0 | 100 | Step 1: 10 mL/hr over 20 min (±5 min), if no IAR<br>Step 2: 30 mL/hr over 20 min (±5 min), if no IAR<br>Step 3: 60 mL/hr over 20 min (±5 min), if no IAR<br>Step 4: 100 mL/hr for the remainder of the infusion if no IAR | Step 1: 0.1 mg/kg/hr over 20 min (±5 min), if no IAR<br>Step 2: 0.3 mg/kg/hr over 20 min (±5 min), if no IAR<br>Step 3: 0.6 mg/kg/hr over 20 min (±5 min), it no IAR<br>Step 4: 1.0 mg/kg/hr for the remainder of the infusion if no IAR | 100 |
| 2.0 | 200 | Step 1: 10 mL/hr over 20 min (±5 min), if no IAR<br>Step 2: 30 mL/hr over 20 min (±5 min), if no IAR<br>Step 3: 60 mL/hr over 20 min (±5 min), if no IAR | Step 1: 0.1 mg/kg/hr over 20 min (±5 min), if no IAR<br>Step 2: 0.3 mg/kg/hr over 20 min (±5 min), if no IAR<br>Step 3: 0.6 mg/kg/hr over 20 min (±5 min), if no IAR | 120 |

TABLE 9-continued

Administration of rhASM

| rhASM Dose (mg/kg) | Total Volume of 0.9% Sodium Chloride for Injection, to be mixed (mL) | Approximate Infusion Rate (mL/hr) | Approximate Infusion Rate mg/kg/hr) | Length of Administration (approximate time [min]) |
|---|---|---|---|---|
| | | Step 4: 100 mL/hr over 20 min (±5 min), if no IAR Step 5: 200 mL/hr for the remainder of the infusion if no IAR | Step 4: 1.0 mg/kg/hr over 20 min (±5 min), if no IAR Step 5: 2.0 mg/kg/hr for the remainder of the infusion if no IAR | |
| 3.0 | 300 | Step 1: 10 mL/hr over 20 min (±5 min), if no IAR Step 2: 30 mL/hr over 20 min (±5 min), if no IAR Step 3: 60 mL/hr over 20 min (±5 min), if no IAR Step 4: 100 mL/hr over 20 min (±5 min), if no IAR Step 5: 200 mL/hr over 20 min. (±5 min), if no IAR Step 6: 300 mL/hr for the remainder of the infusion if no IAR | Step 1: 0.1 mg/kg/hr over 20 min (±5 min), if no IAR Step 2: 0.3 mg/kg/hr over 20 min (±5 min), if no IAR Step 3: 0.6 mg/kg/hr over 20 min (±5 min), if no IAR Step 4: 1.0 mg/kg/hr over 20 min (±5 min), if no IAR Step 5: 2.0 mg/kg/hr over 20 min (±5 min), if no IAR Step 6: 3.0 mg/kg/hr for the remainder of the infusion if no IAR | 135 | hr = hour;
IAR = Infusion-associated reaction;
min = minutes

Clinical end points can be measured as the percent (%) change from baseline in spleen volume multiples of normal (as measured by magnetic resonance imaging) after 26 weeks of receiving the maximum tolerated or randomized dose of rhASM. Secondary efficacy endpoints include liver volume (as measured by MRI); pulmonary imaging (by high resolution computed tomography scan and chest X ray; pulmonary function tests, including percent predicted diffusing capacity of carbon monoxide, percent predicted forced vital capacity, forced expiratory volume in 1 second, and total lung capacity; exercise capacity by cycle ergometry, including percent predicted maximum workload, peak oxygen consumption, and carbon dioxide production; physician global assessment of change: efficacy biomarkers such as serum chitotriosidase, CCL18, and ACE; and hematology parameters such as platelet count, hemoglobin level. Efficacy assessments can also include fasting lipids, coagulation studies, disease related biomarkers, health outcome measures, and patient photographs.

Safety assessments can be performed prior to, during and/or subsequent to dose administration. Safety assessments that can be performed include: a physical examination with neurological assessment, vital signs (e.g., systolic and diastolic blood pressure, temperature, heart rate, respiratory rate and oxygen saturation), ECG, CHO with Doppler, blood chemistry (e.g., sodium, potassium, calcium, chloride, blood urea nitrogen, creatinine, uric acid, ALT, aspartate aminotransferase, total bilirubin, lactate dehydrogenase, alkaline phosphate, total protein, albumin, glucose, cholesterol, etc.), hematology (e.g., a complete blood count), urinalysis, biomarker analysis for biomarkers related to cancer, hormones, cytokines (e.g., IL-8 and IL-6), cardiovascular risk, acute phase reactants and other cellular processes, serum anti-rhASM IgG concentration, serum anti-rhASM IgE concentration, serum tryptase activity, and skin testing for hypersensitivity. Further, pharmacokinetics and pharmacodynamics assessments can be performed prior to, during and/or subsequent to dose administration. For example, sphingomyelin levels can be assessed in the liver and skin by biopsy, and in plasma and DBS by tandem mass spectrometry.

10. EMBODIMENTS

The invention is illustrated by the following non-limiting embodiments:

1. A method for treating a human subject having an acid sphingomyelinase deficiency, comprising:
   (a) a regimen for debulking accumulated sphingomyelin substrate in the human subject comprising:
      i) administering an initial low non-toxic dose of acid sphingomyelinase (ASM) to the human subject;
      ii) administering successively higher doses of ASM to the human subject, and monitoring the subject for one or more adverse side effects after each successive dose as indicated by elevated bilirubin or a related adverse event; and
   (b) a maintenance regimen comprising administering a dose equal to or less than the highest dose tolerated by the subject as the maintenance dose for the subject.

2. An acid sphingomyelinase (ASM) for use in the treatment of an acid sphingomyelinase deficiency in a human subject prepared to be administered:
   (a) in a regimen for debulking accumulated sphingomyelin substrate comprising:
      (i) administration of an initial low non-toxic dose of acid sphingomyelinase (ASM);
      (ii) administration of successively higher doses of ASM, and monitoring the subject for one or more adverse side effects after each successive dose as indicated by elevated bilirubin or a related adverse event: and
   (b) in a maintenance regimen comprising administration of a dose equal to or less than the highest dose tolerated by the subject as the maintenance dose for the subject.

3. The method according to paragraph 1 in which the ASM is recombinant human ASM (rhASM).

4. The method according to paragraph 3 in which the initial dose ranges is from 0.1 mg/kg to 1 mg/kg of rhASM.

5. The method according to paragraph 3 in which the initial dose is 0.1 mg/kg to 0.5 mg/kg of rhASM.

6. The method according to paragraph 3, in which the initial dose is 0.1 mg/kg of rhASM.

7. The method according to any one of paragraphs 1 and 3 to 6, in which the successively higher doses are administered one, two, three or four weeks after the previous dose.

8. The method according to paragraph 7 in which the successively higher dose is administered one week after the previous dose.

9. The method according to paragraph 7 in which the successively higher dose is administered two weeks after the previous dose.

10. The method according to any one of paragraphs 7, 8 and 9 in which the successively higher dose is approximately 0.1 to 1.0 mg/kg higher than the previous dose.

11. The method according to any one of paragraphs 7, 8 and 9 in which the successively higher dose is approximately 0.1 to 0.5 mg/kg higher than the previous dose.

12. The method according to any one of paragraphs 1, and 3 to 10, in which the highest dose tolerated by the human subject is 1 mg/kg to 3 mg/kg.

13. The method according to any one of paragraphs 1 to 11 in which the highest dose tolerated is administered to the human subject as the maintenance dose.

14. The method according to any one of paragraphs 1 to 11 in which the maintenance dose is a therapeutically effective dose less than the highest dose tolerated.

15. The method according to any one of paragraphs 1 to 13 which further comprises monitoring the subject during the maintenance regimen for one or more adverse side effects as indicated by elevated bilirubin or a related adverse event; and adjusting the maintenance dose.

16. The method according to any one of paragraphs 13 to 15, in which the maintenance dose is administered to the subject every two to four weeks.

17. The ASM according to paragraph 2 which is rhASM.

18. The rhASM according to paragraph 17, in which the initial dose ranges is from 0.1 mg/kg to 1 mg/kg of rhASM.

19. The rhASM according to paragraph 17, in which the initial dose is 0.1 mg/kg to 0.5 mg/kg of rhASM.

20. The rhASM according to paragraph 17, in which the initial dose is 0.1 mg/kg of rhASM.

21. The ASM according to any one of paragraphs 2 and 17 to 20, in which the successively higher doses are administered one, two, three or four weeks after the previous dose.

22. The ASM according to paragraph 21 in which the successively higher dose is administered one week after the previous dose.

23. The ASM according to paragraph 21 in which the successively higher dose is administered two weeks after the previous dose.

24. The ASM according to any one of paragraphs 21, 22 and 23 in which the successively higher dose is approximately 0.1 to 1.0 mg/kg higher than the previous dose.

25. The ASM according to any one of paragraphs 21, 22 and 23 in which the successively higher dose is approximately 0.1 to 0.5 mg/kg higher than the previous dose.

26. The ASM according to any one of paragraphs 2 and 17 to 26, in which the highest dose tolerated by the human subject is 1 mg/kg to 3 mg/kg.

27. The ASM according to any one of paragraphs 2 and 17 to 26 in which the highest dose tolerated is administered to the human subject as the maintenance dose.

28. The ASM according to paragraph 27 in which the maintenance dose is a therapeutically effective dose less than the highest dose tolerated.

29. The ASM according to paragraph 27 in which the maintenance dose is administered to the subject every two to four weeks.

30. A method for treating a human subject having an acid sphingomyelinase deficiency, comprising administering rhASM in an escalating dose regimen at the following sequential doses:
 (a) 0.1 mg/kg,
 (b) 0.3 mg/kg, and
 (c) 0.6 mg/kg;
wherein each dose of rhASM is administered at least twice, and each dose is administered at two week intervals, and wherein the subject is monitored for toxic side effects before elevating the dose to the next level.

31. The method according to paragraph 30 further comprising a sequential dose of 1 mg/kg in the escalating dose regimen.

32. The method according to paragraph 31 further comprising a sequential dose of 2 mg/kg in the escalating dose regimen.

33. The method according to paragraph 32 further comprising a sequential dose of 3 mg/kg in the escalating dose regimen.

34. A rhASM for use in the treatment of an acid sphingomyelinase deficiency in a human subject prepared to be administered in an escalating dose regimen at the following sequential doses:
 (a) 0.1 mg/kg.
 b) 0.3 mg/kg, and
 c) 0.6 mg/kg;
wherein each dose of is administered at least twice, and each dose is administered at two week intervals, and wherein the subject is monitored for toxic side effects before elevating the dose to the next level.

35. The rhASM according to paragraph 34 further comprising a sequential dose of 1 mg/kg in the escalating dose regimen.

36. The rhASM according to paragraph 35 further comprising a sequential dose of 2 mg/kg in the escalating dose regimen.

37. The rhASM according to paragraph 36 further comprising a sequential dose of 3 mg/kg in the escalating dose regimen.

38. The method according to any one of paragraphs 1, 3 to 16 and 30 to 33, in which the doses are administered intravenously.

39. The method according to any one of paragraphs 1, 3 to 16 and 30 to 33, in which the doses are administered intradermally, subcutaneously and intramuscularly.

40. The method according to any one of paragraphs 1, 3 to 16 and 30 to 33, in which the acid sphingomyelinase deficiency is Niemann Pick Disease (NPD) type A.

41. The method according to any one of paragraphs 1, 3 to 16 and 30 to 33, in which the acid sphingomyelinase deficiency is NPD type B.

42. The method according to any one of paragraphs 1, 3 to 16 and 30 to 33, in which the human subject has a missense mutation in the gene encoding acid sphingomyelinase.

43. The method according to any one of paragraphs 1, 3 to 16 and 30 to 33, in which the mutation is L302P, H421Y and R496L.

44. The method according to any one of paragraphs 1, 3 to 16 and 30 to 33, in which the human subject has a mutation in the gene encoding acid sphingomyelinase and the mutation is ΔR608.

45. The ASM according to any one of paragraphs 2, 17 to 29 and 34 to 37, in which the doses are administered intravenously.

46. The ASM according to any one of paragraphs 2, 17 to 29 and 34 to 37, in which the doses are administered subcutaneously and intramuscularly.

47. The ASM according to any one of paragraphs 2, 17 to 29 and 34 to 37, in which the acid sphingomyelinase deficiency is Niemann Pick Disease (NPD) type A.

48. The ASM according to any one of paragraphs 2, 17 to 29 and 34 to 37, in which the acid sphingomyelinase deficiency is NPD type B.

49. The ASM according to any one of paragraphs 2, 17 to 29 and 34 to 37, in which the human subject has a missense mutation in the gene encoding acid sphingomyelinase.

50. The ASM according to any one of paragraphs 2, 17 to 29 and 34 to 37, in which the mutation is L302P, H421Y and R496L.

51. The ASM according to any one of paragraphs 2, 17 to 29 and 34 to 37, in which the human subject has a mutation in the gene encoding acid sphingomyelinase and the mutation is ΔR608.

All references cited herein are incorporated herein by reference in their entirety and for all purposes to the same extent as if each individual publication or patent or patent application was specifically and individually indicated to be incorporated by reference in its entirety for all purposes.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

What is claimed:

1. A method for reducing sphingomyelin accumulation in one or more organs of a human subject having an acid sphingomyelinase deficiency (ASMD), comprising:
   (a) administering at least one initial dose of recombinant human acid sphingomyelinase (rhASM) to the human subject, wherein the initial dose is from 0.025 mg/kg to 0.275 mg/kg; and
   (b) subsequent to the administration of the at least one initial dose, administering a higher dose of rhASM to the human subject, wherein the higher dose is from 0.1 mg/kg to 3.0 mg/kg higher than the initial dose.

2. A method for reducing sphingomyelin accumulation in one or more organs of a human subject having an acid sphingomyelinase deficiency (ASMD), comprising:
   (a) administering at least one initial dose of recombinant human acid sphingomyelinase (rhASM) to the human subject, wherein the initial dose is from 0.025 mg/kg to 0.275 mg/kg; and
   (b) subsequent to the administration of the at least one initial dose, administering a higher dose of rhASM to the human subject, wherein the higher dose is from 0.5 mg/kg to 2 mg/kg higher than the initial dose.

3. The method of claim 1, wherein each dose is administered one, two, three, or four weeks after the previous dose.

4. The method of claim 2, wherein each dose is administered one, two, three, or four weeks after the previous dose.

5. The method of claim 1, wherein the doses are administered intravenously, intradermally, subcutaneously, or intramuscularly.

6. The method of claim 2, wherein the doses are administered intravenously, intradermally, subcutaneously, or intramuscularly.

7. The method of claim 1, wherein the ASMD is Niemann Pick Disease (NPD) type A or NPD type B.

8. The method of claim 2, wherein the ASMD is Niemann Pick Disease (NPD) type A or NPD type B.

9. The method of claim 1, wherein the human subject has a mutation in the gene encoding acid sphingomyelinase.

10. The method of claim 2, wherein the human subject has a mutation in the gene encoding acid sphingomyelinase.

11. The method of claim 1, wherein the one or more organs in which sphingomyelin is reduced is the liver, spleen, lungs, heart, kidney, skin, and/or brain of the human subject.

12. The method of claim 2, wherein the one or more organs in which sphingomyelin is reduced is the liver, spleen, lungs, heart, kidney, skin, and/or brain of the human subject.

13. The method of claim 11, wherein the one or more organs is the liver.

14. The method of claim 12, wherein the one or more organs is the liver.

15. The method of claim 13, wherein reduction of sphingomyelin in the liver is determined by biopsy or by a liver function test.

16. The method of claim 14, wherein reduction of sphingomyelin in the liver is determined by biopsy or by a liver function test.

17. The method of claim 15, wherein the liver function test assesses the concentration of alanine aminotransferase (ALT), aspartate aminotransferase (AST), alkaline phosphatase (AP), gamma-glutamyl transferase (GGT) and/or total and direct bilirubin.

18. The method of claim 16, wherein the liver function test assesses the concentration of alanine aminotransferase (ALT), aspartate aminotransferase (AST), alkaline phosphatase (AP), gamma-glutamyl transferase (GGT) and/or total and direct bilirubin.

* * * * *

SEQUENCE LISTING

```
<160> NUMBER OF SEQ ID NOS: 3

<210> SEQ ID NO 1
<211> LENGTH: 629
<212> TYPE: PRT
<213> ORGANISM: Homo sapiens
<220> FEATURE:
<223> OTHER INFORMATION: human ASM isoform 1 (ASM-1),
      UniProtKB/Swiss-Prot Accession No. P17405-1

<400> SEQUENCE: 1

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
                20                  25                  30

Met Gly Leu Val Leu Ala Leu Ala Leu Ala Leu Ala Leu Ala Leu Ser
            35                  40                  45

Asp Ser Arg Val Leu Trp Ala Pro Ala Glu Ala His Pro Leu Ser Pro
        50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
                100                 105                 110

Gly Ser Val Ala Ile Lys Leu Cys Asn Leu Leu Lys Ile Ala Pro Pro
            115                 120                 125

Ala Val Cys Gln Ser Ile Val His Leu Phe Glu Asp Asp Met Val Glu
        130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
                180                 185                 190

Ala Pro Gly Ala Pro Val Ser Arg Ile Leu Phe Leu Thr Asp Leu His
            195                 200                 205

Trp Asp His Asp Tyr Leu Glu Gly Thr Asp Pro Asp Cys Ala Asp Pro
        210                 215                 220

Leu Cys Cys Arg Arg Gly Ser Gly Leu Pro Pro Ala Ser Arg Pro Gly
225                 230                 235                 240
```

```
Ala Gly Tyr Trp Gly Glu Tyr Ser Lys Cys Asp Leu Pro Leu Arg Thr
            245                 250                 255

Leu Glu Ser Leu Leu Ser Gly Leu Gly Pro Ala Gly Pro Phe Asp Met
        260                 265                 270

Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
    290                 295                 300

Lys Phe Leu Gly Pro Val Pro Val Tyr Pro Ala Val Gly Asn His Glu
305                 310                 315                 320

Ser Thr Pro Val Asn Ser Phe Pro Pro Phe Ile Glu Gly Asn His
                325                 330                 335

Ser Ser Arg Trp Leu Tyr Glu Ala Met Ala Lys Ala Trp Glu Pro Trp
                340                 345                 350

Leu Pro Ala Glu Ala Leu Arg Thr Leu Arg Ile Gly Gly Phe Tyr Ala
            355                 360                 365

Leu Ser Pro Tyr Pro Gly Leu Arg Leu Ile Ser Leu Asn Met Asn Phe
        370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
                405                 410                 415

Gly Asp Lys Val His Ile Ile Gly His Ile Pro Pro Gly His Cys Leu
                420                 425                 430

Lys Ser Trp Ser Trp Asn Tyr Tyr Arg Ile Val Ala Arg Tyr Glu Asn
            435                 440                 445

Thr Leu Ala Ala Gln Phe Phe Gly His Thr His Val Asp Glu Phe Glu
    450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
                485                 490                 495

Val Tyr Gln Ile Asp Gly Asn Tyr Ser Gly Ser Ser His Val Val Leu
                500                 505                 510

Asp His Glu Thr Tyr Ile Leu Asn Leu Thr Gln Ala Asn Ile Pro Gly
            515                 520                 525

Ala Ile Pro His Trp Gln Leu Leu Tyr Arg Ala Arg Glu Thr Tyr Gly
    530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
                565                 570                 575

Gly His Pro Pro Ser Glu Pro Cys Gly Thr Pro Cys Arg Leu Ala Thr
                580                 585                 590

Leu Cys Ala Gln Leu Ser Ala Arg Ala Asp Ser Pro Ala Leu Cys Arg
            595                 600                 605

His Leu Met Pro Asp Gly Ser Leu Pro Glu Ala Gln Ser Leu Trp Pro
    610                 615                 620

Arg Pro Leu Phe Cys
625

<210> SEQ ID NO 2
<211> LENGTH: 12
```

```
<212> TYPE: PRT
<213> ORGANISM: Homo sapiens
<220> FEATURE:
<223> OTHER INFORMATION: amino acid residues 363 to 374 of ASM-1

<400> SEQUENCE: 2

Ile Gly Gly Phe Tyr Ala Leu Ser Pro Tyr Pro Gly
 1               5                  10

<210> SEQ ID NO 3
<211> LENGTH: 12
<212> TYPE: PRT
<213> ORGANISM: Homo sapiens
<220> FEATURE:
<223> OTHER INFORMATION: amino acid residues 363 to 374 of ASM-2 (see
      UniProtKB/Swiss-Prot Accession No. P17405-2)

<400> SEQUENCE: 3

Tyr Leu Ser Ser Val Glu Thr Gln Glu Gly Lys Arg
 1               5                  10
```